(12) United States Patent
Fujisawa et al.

(10) Patent No.: US 6,284,914 B1
(45) Date of Patent: Sep. 4, 2001

(54) HIGHLY WATER-SOLUBLE METALLOPROTEINASE INHIBITORS

(75) Inventors: Junko Fujisawa; Eiko Suda; Katsuhiro Igeta; Tadanori Morikawa; Tetsunori Fujisawa; Shinjiro Odake; Yasuo Morita; Tomoko Hongo; Hajime Ito, all of Takaoka (JP)

(73) Assignee: Fuji Yakuhin Kogyo Kabushiki Kaisha, Toyama (JP)

( * ) Notice: Subject to any disclaimer, the term of this patent is extended or adjusted under 35 U.S.C. 154(b) by 0 days.

(21) Appl. No.: 09/492,149

(22) Filed: Jan. 27, 2000

Related U.S. Application Data

(62) Division of application No. 08/945,356, filed as application No. PCT/JP96/01135 on Apr. 25, 1996, now Pat. No. 6,147,114.

(30) Foreign Application Priority Data

Apr. 25, 1995 (JP) .................................................... 7-123045

(51) Int. Cl.[7] .......................... C07C 237/04; C07C 229/28
(52) U.S. Cl. ................................. 560/13; 560/16; 560/34; 560/39; 560/41; 562/426; 562/430; 562/434; 562/437; 562/439; 562/448; 562/564; 562/15; 562/164; 562/165
(58) Field of Search ............................. 564/164, 15, 165; 560/13, 16, 34, 39, 41; 562/426, 430, 434, 437, 439, 448

(56) References Cited

U.S. PATENT DOCUMENTS

| | | |
|---|---|---|
| 4,599,361 | 7/1986 | Dickens et al. . |
| 5,183,900 | 2/1993 | Galardy et al. . |
| 5,300,674 | 4/1994 | Crimmin et al. . |
| 5,412,145 | 5/1995 | Crimmin et al. . |
| 5,442,110 | 8/1995 | Isomura et al. . |
| 5,514,716 | 5/1996 | Gowravaram et al. . |

FOREIGN PATENT DOCUMENTS

| | | |
|---|---|---|
| 0606046A1 | 7/1994 | (EP) . |
| 57844A2 | 12/1997 | (EP) . |
| 2268933A | 1/1994 | (GB) . |
| 6-87813 | 3/1994 | (JP) . |
| 6-506445 | 7/1994 | (JP) . |
| 92 13831 | 8/1992 | (WO) . |
| 94 02446 | 2/1994 | (WO) . |
| 94 02447 | 2/1994 | (WO) . |
| 95 19956 | 7/1995 | (WO) . |
| 95 22966 | 8/1995 | (WO) . |

OTHER PUBLICATIONS

Database CAPLUS on STN, Acc. No. 1994:457993, Broadhurst et al., 'Preparation of N–(N–hydroxysuccinamoyl) amino acid derivatives as matrix metalloproteinase inhibitors,' EP 575844 A2 (abstract), 1994.

Database CAPLUS on STN, Acc. No. 1993:39408, Beckett et al., 'Preparation of amino acid hydroxanates as collagenase inhibitors.' EP 498665 A1 (abstract), 1993.

Database CAPLUS on STN, Acc. No. 1967:179, Prescott et al., 'Aeromonas aminopeptidase: purification and some general properties.' Arch. Biochem. Biophys. (1966), 117(2), p. 328–36 (abstract), 1967.

Database CAPLUS on STN, Acc. No. 1986:532163, Kitahata et al., 'Alpha amino acid amides.' JP 60244296 A2 (abstract), 1986.*

Database CAPLUS on STN, Acc. No. 1993:39408, Beckett et al., 'Preparation of amino acid amide hydroxanates as collagenase inhibitors.' EP 498665 A1 (abstract), 1993.*

D. Brown, et al, Current Eye Research vol. 12 No. 6 1993, 571–581, Keratoconus corneas: increased gelatinolytic activity appears affter modifications of inhibitors.

(List continued on next page.)

Primary Examiner—Johann Richter
Assistant Examiner—Brian J. Davis
(74) Attorney, Agent, or Firm—Birch, Stewart, Kolasch & Birch, LLP

(57) ABSTRACT

New compounds of general formulae (III), (IV) and (V).

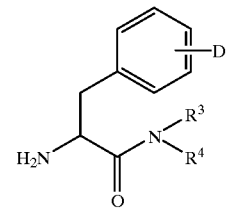

III

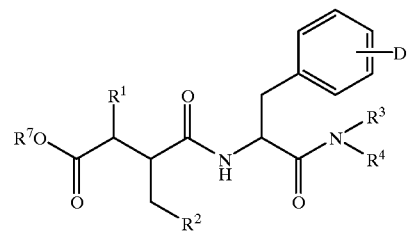

IV

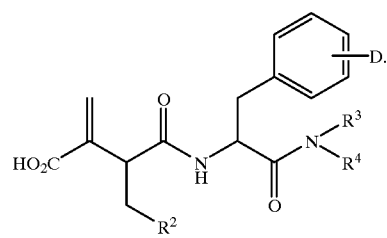

V

3 Claims, No Drawings

OTHER PUBLICATIONS

Cancer and Metastasis Reviews 9:289–303, 1990, 1990 Kluwer Academic Publishers Printed in the Netherlands, Type IV collagenases in tumor invasion and metastasis, William G. Stetler–Stevenson Laboratory of Pathology, National Cancer Institute, NAtional Institutes of HEalth, Bethesda, MD, USA.

Critical Reviews in Oral Biology and Medinine, 4(2) : 197–240 (1993) Matrix Metalloproteinases: A Review*, H. Birkedal–Hansen et al, Department of Oral Biology, REsearch Center in Oral Biology.

Matrix Metalloproteinases and Processing of Pro–TNF–, A.J.H. Gearing et al, Neures Limited and British Biotech, Oxford, United Kingdom, Journal of LEukocyte Biology vol. 57, May 1995, pp. 774–777.

Letter To Nature, Protection against a lethal dose of endotoxin by an inhibitor of tumor necrosis factor processing, Kendal M. Mohler, et al, Immunex Research and Development Corp. pp. 218–220.

Letters To Nature, Regulation of tumor necrosis factor–processing by a metalloproteinase inhibitor, Gerard M. McGeehan et al, Glaxco Inc. Research Institute, Research Triangle Park, North Carolina 27709, USA, pp. 558–561.

J. Org. Chem. 1982, 47, 4928–4933, Enantioselective Syntheses of 3–Substituted 4–(Alkoxycarbonyl)–2–azetidinones from Malic Acid, MArvin J. Miller, et al, Department of Chemistry, University of Notre Dame, Notre Dame, Indians 46558.

Helvetica Chimica Acta–vol. 66, Fasc. 5(1093)–Nr. 128, 128, Angiotensin II Analogues, Part II, Synthesis and Incorporation of the SUlfur–Containing Aromatic Amino Acids, by Emanuel Escher, et al.

Journal of Hepatology, 1993; 18: 328–334, 1993 Elseview Scientific Publishers Ireland Ltd., Serum collagenase activity in patients with chronic liver disease, Yoshikazu Murawaki et al.

Analytical Biochemistry 143 30–34, (1984), Fluorescein Isothiocyanate–Labeled Casein Assay for Proteolytic Enzymes, Sally S. Twining, Department of Biochemistry and Ophthalmology, Medical College of Wisconsin, Milwaukee, Wisconsin 53226.

Virchows Archiv B Cell Pathol (1990) 59–305–312, Virchows Archiv B Cell Pathology Including Molecular Pathology Springer–Verlag 1990, Immumohistochemical demonstration of collagenase and tissue inhibitor of metalloproteinases (TIMP) in synovial lining cells of rheumatoid synovium, Yasumori Okada et al.

Database CAPLUS on STN, Acc. No. 1993:39408, Beckett et al., "Preparation of amino acid amide hydroxanates as collagenase inhibitors." EP 498665 Al, abstract (1993).

* cited by examiner

HIGHLY WATER-SOLUBLE METALLOPROTEINASE INHIBITORS

This application is a divisional of application Ser. No. 08/945,356, filed on Oct. 24, 1997 now U.S. Pat. No. 6,147,114. Application Ser. No. 08/945,356 is the national phase of PCT International Application No. PCT/JP96/01135 filed on Apr. 25, 1996 under 35 U.S.C. § 371. The entire contents of each of the above-identified applications are hereby incorporated by reference.

SPECIFICATION

1. Field of Industrial Application

The invention relates to new highly water-soluble compounds, which inhibit matrix metalloproteinases (MMPs) derived from vertebrates and/or tumor necrosis factor-α (TNF-α) converting enzyme, preparation intermediates thereof and a process for the preparation thereof.

2. Background Art

MMPs which belong to endo proteinases containing zink are involved in the decomposition of an extra-cellular matrix in a connective tissue. Up to now, it is known that there exist ten-odd MMPs, and the expression of these enzymes are strictly controlled in healthy volunteers. However, an abnormal aggravation of MMPs is observed in cases such as chronic rheumatoid arthritis, osteoarthritis, periodental disease, corneal ulcer, various kinds of bullosis (epidermolisis bullosa hereditaria, epidermolisis bullosa acquisita, porphylia cutanea tarda, bullos penphigoid, pemphigus vulgaris), intractable skin ulcer (bedsore, skin ulcer in radiotherapy, skin ulcer in diabetes mellitus, skin ulcer in arteriosclerotic obliteration), wound (external injury or burn), osteoporosis, cancer metasis and the like, and these are considered to participate in the destruction of the extra-cellular matrix. [D. Brown et al., *Current Eye Research*, 12, 571(1993)/Y. Okada et al., *Virchows Archiv. B, Cell Pathol.*, 59, 305(1990)/W. G. Stetler-Stevenson, *Cancer Metastasis Reviews*, 9,289(1990)/H. Birkedal-Hansen et al., *Critical Reviews in Oral Biology and Medicine*, 4(2),197(1993)] On the contrary, TNF-α is produced as a membrane-bound type precursor of molecular weight 26K, and in case of the excess of an extra-cellular release is considered the occurrence of diseases such as sepsis, chronic rheumatoid arthritis or the like. Recently, it was reported that the enzyme (TNF-α converting enzyme) inducing the release of TNFα was a metalloproteinase whose activity was controlled by a MMPs inhibitor. [A. J. H. Gearing et al., *Journal of Leukocyte Biology*, 57, 774(1995), K. M. Mohler et al., *Nature*, 370, 218(1994), G. M. NcGeehan et al., *Nature*, 370, 558(1994)].

Accordingly, in the above diseases, inhibiting the action of these enzymes becomes an effective method of therapy. However, as the compounds having MMPs inhibitory activities are known the compounds divided into four families which are phosphonic acid derivatives, hydroxamic acid derivatives, derivatives having mercapto group and derivatives having carboxyl group. Especially, on the hydroxamic acid derivatives are proposed compounds having various skeletons (see U.S. Pat. No. 4,599,361, EP, 575844 A2, U.S. Pat. No. 5,412,145, WO, 92/13831, U.S. Pat. No. 5,183,900, WO, 94/02447, EP, 606046 A1 and GB 2268933 A), and many of these compounds have highly inhibitory activities for various kinds of MMPs. However, each of these compounds is poor in its water-solubility and their administration methods are limited. For example, in case of applying these compounds as injections (aqueous solution), medicaments of high concentration cannot be prepared.

Furthermore, in case of administering injections into joint, if there is a particle not less than 50 μm, the occurrence of a synovial inflammation is known, therefore, it becomes a necessary condition for a compound to be completely dissolved state. In the known compounds, such an administration is impossible, and it is a present situation that they are not effectively utilized as therapeutic agents.

DISCLOSURE OF THE INVENTION

The inventors gave attention to the hydroxamic acid derivatives having highly inhibitory activities, and as the result of making an extensive studies to enhance the availability, we accomplished the invention by finding out new hydroxamic acid derivatives whose water-solubility was dramatically increased compared with that of the above compounds' group.

Accordingly, the invention provides compounds of general formula (I)

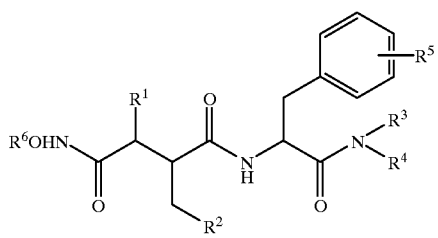

I (wherein $R^1$ is a hydrogen atom, or a hydroxyl, aryl $(C_1-C_6)$alkylene or —A—SOn—B group (A is a $(C_1-C_6)$ alkylene group; B is a $(C_1-C_6)$ alkyl, $(C_1-C_6)$ acyl, aryl or heterocyclyl groups; n is 0, 1 or 2), $R^2$ is a hydrogen atom, or a $(C_1-C_6)$ alkyl, $(C_1-C_6)$ alkyloxy or $(C_1-C_6)$ alkylthio groups, $R^3$ and $R^4$ are identical or different, representing a hydrogen atom, or a $(C_1-C_6)$ alkyl, aryl or aryl$(C_1-C_6)$alkylene groups, $R^5$ is a Y—C" or C" group (Y is a $(C_1-C_6)$ alkylene group, an oxygen atom, an imino or $(C_1-C_6)$ alkyleneimino groups, C" is a sulfonic acid, phosphonic acid, amidino, $(C_1-C_6)$ acyl, acylimidoyl, diphosphonomethine or dicarboxymethine groups), and $R^6$ is a hydrogen atom, or a nonsubstituted or substituted benzyl, trialkylsilyl, tert-butyldiphenylsilyl, tetrahydropyranyl or tert-butyl groups) or stereoisomers thereof, and pharmaceutically acceptable salts thereof and solvates thereof, and metalloproteinase inhibitors which comprise one or more compounds selected from those compounds as effective ingredients and inhibit matrix metalloproteinases (MMPs) and/or TNF-α converting enzyme. Further, the invention provides preparation intermediates to obtain the compounds of the above formula (I) and process for the preparation.

In the following, the invention will be explained in detail.

In the compounds represented by the general formula (I) according to the invention are included compounds described below.

The sulfonic acid group indicates —SO₃H, and the sulfuric acid group is —OSO₃H. The phosphonic acid group indicates —PO₃H₂, and phosphate is —OPO₃H₂. The amidino group indicates —C(=NH)NH₂, and the guanido group does —NH—C(=NH)NH₂. The aminomethylene group indicates —CH₂NH₂ and the guanidomethylene group —CH₂—NH—C(=NH)NH₂. The acetamidomethylene group indicates —CH₂NH—COCH₃, the acetimidoyliminomethylene group —CH$_2$—NH—C(=NH)CH$_3$, the propionimidoyliminomethylene group —CH$_2$—NH—C(=NH)CH$_2$CH$_3$, the benzimidoyliminomethylene group —CH$_2$—NH—C(=NH)C$_6$H$_5$, the diphosphonomethine group —CH[PO(OH)$_2$]$_2$ and the dicarboxymethine group —CH(CO$_2$H)$_2$, respectively.

The (C$_1$–C$_6$) alkyl group indicates an alkyl group of straight chain or branched chain containing 1–6 carbon atoms, including methyl, ethyl, n-propyl, iso-propyl, n-butyl, sec-butyl, tert-butyl, pentyl and hexyl groups, etc. The (C$_1$–C$_6$) alkylene group indicates —(CH$_2$)$_n$—(n=1–6). The imino group indicates —NH—.

The (C$_1$–C$_6$) alkyleneimino group indicates —(CH$_2$)$_n$—NH—(n=1–6), which is preferably (C$_1$–C$_3$) alkyleneimino group and more preferably —CH$_2$—NH—.

The (C$_1$–C$_6$) acyl group indicates a alkylacyl group of straight chain or branched chain containing 1–6 carbon atoms, including formyl, acetyl, n-propanoyl and n-butanoyl groups, etc.

The acylimidoyl group indicates —C(=NH)—[(C$_1$–C$_6$) alkyl] or —C(=NH)-(aryl).

The heterocyclyl group indicates a cyclic skeleton saturated or unsaturated, having at least one of hetero atoms such as sulfur, oxygen or nitrogen atoms, etc. Illustrative of the preferable heterocyclyl group are, for example, thienyl, thiazolyl, imidazolyl or pyridyl groups, etc.

The aryl group indicates aromatic rings such as phenyl, naphthyl or anthracenyl groups, etc., which can be substitued.

The substituents on the aryl group include (C$_1$–C$_6$) alkyl, (C$_1$–C$_6$) acyl, hydroxyl, amino and carboxyl groups, a halogen atom, etc., and in case having two or more substituents, can be a combination of these.

The halogen atom indicates fluorine, chlorine, bromine or iodine atoms.

Additionally, as the salts of compounds of the general formula (I) are included inorganic salts consisting of alkaline metals such as sodium and potassium, etc., alkaline earth metals such as magnesium and calcium, etc., or mineral acids such as hydrochloric acid and hydrobromic acid, etc., and ammonia consisting of organic salts, morpholine, piperidine, dimethylamine, diethylamine, acetic acid, citric acid, oxalic acid, etc. Further, the solvate is, for example, a hydrate.

Since there exist three asymmetric carbon atoms in the compounds represented by the above general formula (I), all the diasteromers of the general formula (I) and the racemates which are a mixture thereof are included.

In the following are explained in detail showing the synthesis-route scheme of compounds of the above general formula (I) according to the invention and of preparation intermediates thereof. In the following description, the compounds are added with number one by one according to the method used conventionally in chemical literature, and the compounds are represented by their numbers. First, the process of preparing the intermediate (II) is explained.

Synthetic route of intermediate (II)

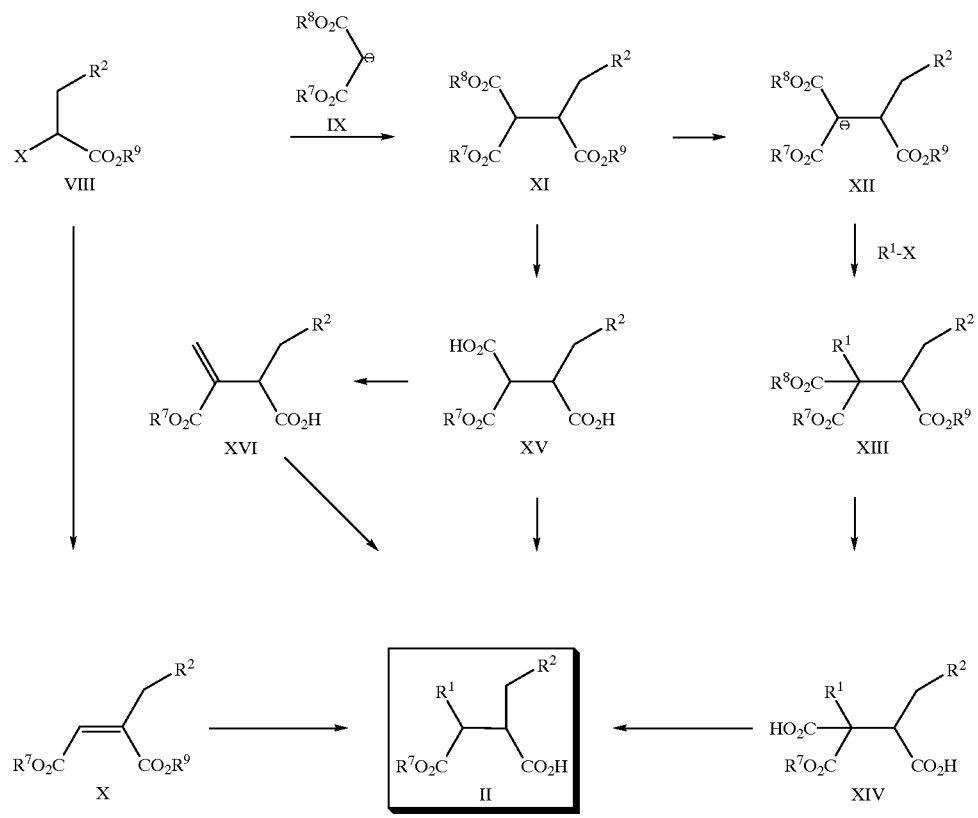

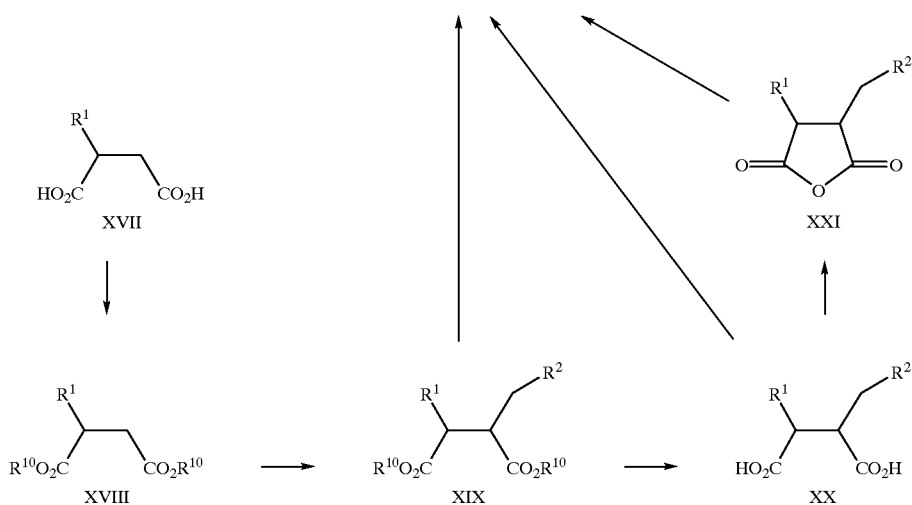

(In the above synthetic route, $R^1$ and $R^2$ have the same meaning described above, and $R^7$, $R^8$, $R^9$ and $R^{10}$ are identical or different, representing ($C_1$–$C_6$) alkyl, benzyl, substituted benzyl, phenacyl or 2,2,2-trichloroethyl groups, and X represents halogen atom or oxo group.)

The route, in which the preparation intermediate (II) is synthesized from the general formula (VIII) as a starting material, is preferable in the case that $R^1$ is hydrogen atom, —A—$SO_n$—B— (A is the ($C_1$–$C_6$) alkylene group; B is ($C_1$–$C_6$) alkyl, ($C_1$–$C_6$) acyl, aryl or heterocyclyl groups; n is 0, 1 or 2.) or aryl ($C_1$–$C_6$)alkylene group.

The general formula (XI) can be obtained by reacting α-halogenocarboxylate (VIII), in which X is a halogen atom, and the formula (IX), being the anionized malonic acid diester ($R^2$ has the same meaning described above, and is preferably the ($C_1$–$C_5$) alkyl group, more preferably isopropyl group. The halogen atom is fluorine, chlorine, bromine or iodine atoms, though, preferably a bromine atom.

As a base used in the anionization of malonic acid diester can be used potassium tert-butoxide, sodium hydride, lithium diisopropylamide (LDA), lithium bis(trimethylsilyl) amide, alcholate or the like, though, preferably sodium hydride or potassium tert-butoxide.

As an inactive organic-solvent for the reaction solvent can be used n-hexane, tetrahydrofuran (THF), benzene, toluene, dimethylformamide (DMF), dimethylacetamide (DMAc), dichloromethane, chloroform, or the like, though, preferably DMF.

The reaction temperature is usually from –78 to 50° C., preferably from 0 to 20° C. The reaction time is different depending on a starting material, solvent, reaction temperature, etc., though, from 30 min. to 4 hours, usually from 1 to 2 hours.

Subsequently, for the reaction with α-halogenocarboxylate (VIII), as the reaction solvent is used an inactive organic-solvent such as n-hexane, THF, benzene, toluene, DMF, DMAc, dichloromethane, chloroform, or the like, though, preferably DMF. The reaction temperature is usually from –10 to 50° C., preferably from –5 to 0° C.

The reaction time is different depending on a starting material, solvent, reaction temperature, etc., though, usually from 2 to 24 hours, preferably from 10 to 20 hours.

The compound of the general formula (XIII) can be prepared by letting the general formula (XI) to the anionized substance (XII) and reacting it with halogenated aryl-($C_1$–$C_6$) alkylene or halogenated alkenyl, if desired, followed by hydrogenation (as aryl-($C_1$–$C_6$) is alkylene preferably phenyl($C_1$–$C_5$)alkylene group, more preferably phenyltrimethylene group. As alkenyl group preferable cinnamyl group ($C_6H_5$—CH=CH—$CH_2$—). As the halogen atom can be cited fluorine, chlorine, bromine or iodine atoms, preferably bromine atom.

As the base used in the synthesis of the formula (XII) can be usedpotassium tert-butoxide, LDA, lithiumbis (trimethylsilyl)amide, sodium hydride, alcholate or the like, which are conventionally used in this kind of reaction, though, preferably sodium hydride.

As the reaction solvent are used an inactive organic-solvent such as n-hexane, THF, benzene, toluene, DMF, DMAc, dichloromethane, chloroform, or the like, though, preferably DMF. The reaction temperature is usually from –10 to 50° C., preferably from 10 to 30° C.

The reaction time is different depending on a starting material, solvent, reaction temperature, etc., though, usually from 30 min. to 4 hours, preferably from 1 to 2 hours.

Following to this, in order to let it react with halogenated aryl-($C_1$–$C_6$)alkylene or halogenated alkenyl, as the reaction solvent is used an inactive organic-solvent such as n-hexane, THF, benzene, toluene, DMF, DMAc, dichloromethane, chloroform, or the like, though, preferably DMF. The reaction temperature is usually from –10 to 50° C., preferably from –5 to 10° C. The reaction time is different depending on a starting material, solvent, reaction temperature, etc., though, usually from 2 to 48 hours, preferably from 10 to 20 hours. Further, if desired, to get the general formula (XIII) by hydrogenation can be used catalysts such as palladium-carbon, platinum or the like as a hydrogenation catalyst, though, preferably palladium-carbon. As the reaction solvent can be used an inactive organic-solvent such as alcohols (methanol, ethanol, etc.), DMF, DMAc or acetic acid, which are not catalytic poison, or water, preferably methanol or ethanol. The reaction temperature is usually from 0 to 50° C., preferably from 10 to 30° C.

The reaction time is different depending on a starting material, solvent, reaction temperature, etc., though, usually from 1 to 24 hours, preferably from 1 to 6 hours.

The compound of the general formula (XIV) can be prepared by the deesterification of the general formula (XIII). $R^7$, $R^8$ and $R^9$ have the same meaning described above, though, in order to get the general formula (XIV), preferably, $R^7$ is tert-butyl group and $R^8$ and $R^9$ are benzyl group. For example, in the case that $R^8$ and $R^9$ are benzyl group can be deesterfied by hydrogenation.

As the hydrogenation catalyst can be used catalysts such as palladium-carbon, platinum, or the like, though, preferably palladium-carbon. As the reaction solvent can be used an inactive organic-solvent such as alcohol (methanol, ethanol, etc.), DMF, DMAc or acetic acid, which are not catalytic poison, or water, preferably methanol or ethanol. The reaction temperature is usually from 0 to 50° C., preferably from 10 to 30° C.

The reaction time is different depending on a starting material, solvent, reaction temperature, etc., though, usually from 1 to 24 hours, preferably from 1 to 7 hours.

The general formula (XV) can be prepared by deesterifying the general formula (XI). $R^7$, $R^8$ and $R^9$ have the same meaning described above, though, in order to get the general formula (XV), preferably, $R^7$ is tert-butyl group and $R^8$ and $R^9$ are benzyl group. For example, in the case that $R^8$ and $R^9$ are benzyl group can be deesterfied by hydrogenation. As the hydrogenation catalyst can be used catalysts such as palladium-carbon, platinum, or the like, though, preferably palladium-carbon. As the reaction solvent can be used an inactive organic-solvent such as alcohols (methanol, ethanol, etc.), DMF, DMAc or acetic acid, which are not catalytic poison, or water, preferably methanol. The reaction temperature is usually from 0 to 50° C., preferably from 10 to 30° C. The reaction time is different depending on a starting material, solvent, reaction temperature, etc., though, usually from 1 to 24 hours, preferably from 1 to 6 hours.

The compound of the general formula (XVI) can be prepared by reacting the Schiff base, which results from formaline and a secondary amine such as piperidine, diethylamine, morpholine or the like, with the general formula (XV), followed by decarboxylation and a simultaneous double bond formation. As the reaction solvent, there is no special restriction if it does not hinder the proceeding of the reaction and dissolve the starting material, though, alcohols, DMF, DMAc or the like can be cited, preferably methanol.

The reaction temperature is usually from 0 to 150° C., preferably from 10 to 100° C.

The reaction time is different depending on a starting material, solvent, reaction temperature, etc., though, usually from 5 to 24 hours, preferably from 10 to 15 hours.

The general formula (X) can be prepared by reacting the Wittig reaction of α-oxocarboxylate (VIII), in which X is a halogen atom, with a phosphorane derivative ($R^7O_2CCH=PE_3$; $R^7$ has the same meaning described above, E is phenyl or alkyl groups.).

As the reaction solvent, there is no special restriction if it does not hinder the proceeding of the reaction and dissolve the starting material, though, it is diethyl ether, dioxane, THF, toluene, benzene, dichloromethane, chloroform, DMF or the like, preferably THF, dichloromethane or benzene.

The reaction temperature is usually from −70 to 120° C., preferably from −20 to 30° C.

The reaction time is different depending on a starting material, solvent, reaction temperature, etc., though, usually from 30 min. to 24 hours, preferably from 1 to 15 hours.

The synthetic route of the preparation intermediate (II) using the general formula (XVII) as a starting material is preferable in the case that $R^1$ is a hydrogen atom or a hydroxyl group.

The general formula (XVIII) can be prepared by reacting the succinic acid derivative with (a) alcohols in the presence of a condensation reagent such as N,N′-dicyclohexylcarbodiimide (DCC), 1-ethyl-3-(3-dimethylaminopropyl)-carbodiimide hydrochloride (EDC-HCl) or the like, and of N,N-dimethylaminopyridine, or (b) halogenated alkyl or halogenated benzyl after converting the formula (XVIII) into salts of sodium, potassium, cesium or the like, or (c) a complex of thionyl chloride and alcohol.

For example, in case of reacting the formula (XVII) with the thionyl chloride-alcohol complex (c), alcohols used have no special restriction, which are methanol, ethanol, n-propyl alcohol, isopropyl alcohol, tert-butyl alcohol, phenol, benzyl alcohol, phenacyl alcohol, 2,2,2-trichloroethanol or the like (preferably, methanol, ethanol, iso-propyl alcohol, tert-butyl alcohol, and more preferably, iso-propyl alcohol), and are used accompanying the reaction solvent.

The reaction temperature is usually from −30 to 10° C., preferably from −10 to 0° C. The reaction time is different depending on a starting material, solvent, reaction temperature, etc., though, usually from 5 to 24 hours, preferably from 10 to 15 hours.

The compound of the general formula (XIX) can be prepared by anionizing the general formula (XVIII) and reacting with halogenated ($C_1$–$C_6$)alkyl or halogenated ($C_1$–$C_6$)alkenyl, if desired, followed by hydrogenation. (As ($C_1$–$C_6$) alkyl group preferable is ($C_1$–$C_5$) alkyl group, especially preferably iso-butyl group. As ($C_1$–$C_6$) alkenyl group preferable is ($C_1$–$C_5$) alkenyl group, especially preferably 2-methylpropene group (—$CH_2$—C($=CH_2$)$CH_3$). As the halogen atom can be cited fluorine, chlorine, bromine or iodine atoms, preferably bromine atom.)

As the base used in the anionization of succinic acid diester (XVIII) can be used potassium tert-butoxide, sodium hydride, LDA, lithium bis(trimethylsilyl)amide, alcholate or the like, which are used in a conventional reaction, though, preferably LDA.

As the reaction solvent are used an inactive organic-solvent such as n-hexane, THF, benzene, toluene, DMF, DMAc, dichloromethane, chloroform, or the like, though, preferably THF. The reaction temperature is usually from −78 to 0° C., preferably from −70 to −10° C.

The reaction time is different depending on a startingmaterial, solvent, reaction temperature, etc., though, from 30 min. to 24 hours, usually from 4 to 12 hours.

Following to this reaction, in order to let it react with halogenated ($C_1$–$C_6$)alkyl or halogenated ($C_1$–$C_6$)alkenyl, as the reaction solvent is used an inactive organic-solvent such as n-hexane, THF, benzene, toluene, DMF, DMAc, dichloromethane, chloroform, or the like, though, preferably THF.

The reaction temperature is usually from −78 to 0° C., preferably from −70 to −10° C. The reaction time is different depending on a starting material, solvent, reaction temperature, etc., though, usually from 2 to 48 hours, preferably from 10 to 20 hours. Further, if desired, to get the general formula (XIX) by hydrogenation can be used catalysts such as palladium-carbon, platinum or the like as a hydrogenation catalyst, though, preferably palladium-carbon. As the reaction solvent can be used an inactive organic-solvent such as alcohol (methanol, ethanol, etc.), DMF, DMAc or acetic acid, which are not catalytic poison, or water, preferably methanol. The reaction temperature is usually from 0 to 50° C., preferably from 10 to 30° C.

The reaction time is different depending on a starting material, solvent, reaction temperature, etc., though, usually from 1 to 24 hours, preferably from 1 to 6 hours.

The compound of the general formula (XX) can be prepared by the deestrification of the general formula (XIX). For example, in the case that $R^{10}$ is iso-propyl group, the deesterification can be done by an alkaline hydrolysis.

As the base used in the hydrolysis, there is no special restriction if it is used as a base in a usual reaction, though, examples are sodium carbonate, potassium carbonate, sodium hydroxide, potassium hydroxide, sodium bicarbonate, lithium hydride, sodium hydride or the like, preferably sodium hydroxide or potassium hydroxide.

As the reaction solvent, there is no special restriction if it does not hinder the proceeding of the reaction and dissolve the starting material, though, it is DMF, DMAc, alcohols, diethyl ether, tetrahydrofuran, dioxane, water, acetone or the like, preferably alcohols, water, dioxane, acetone or a mixed solvent thereof. The reaction temperature is usually from −20 to 150° C., preferably from −10 to 100° C. The reaction time is usually from 5 min. to 36 hours, preferably from 10 min. to 24 hours.

The synthetic intermediate (II) can be prepared by (a) decarboxylating the general formula (XIV), (b) adding the thiol derivative (HS-B, B has the same meaning as described above) to the butenoic acid derivative of the general formula (XVI)), (c) hydrolyzing the diester of the general formula (XIV) partially or (d) reacting the acid anhydride (XXI) from the dicarboxylic acid (XX) with alcohols or the direct half-esterification. Additionally, it can be prepared by (e) decarboxylating the formula (XV) in the case that $R^1$ is a hydrogen atom or (f) hydrogenating the formula (X).

(a), (e) In order to decarboxylate the general formula (XIV) or (XV), the reaction is carried out in the presence of a tertiary amine such as triethylamin, N-methylmorpholine, N-ethylmorpholine or the like. As the reaction solvent can be cited an inactive organic-solvent such as n-hexane, toluene, benzene or the like, preferably toluene.

The reaction temperature is usually from 70 to 150° C., preferably from 100 to 120° C. The reaction time is different depending on a starting material, solvent, reaction temperature, etc., though, usually from 1 to 5 hours, preferably from 2 to 3 hours.

(b) In adding the thiol derivative to the general formula (XVI), there is no special restriction for the reaction solvent if it does not hinder the proceeding of the reaction and dissolves a starting material, though, examples cited are alcohols, DMF, DMAc, dichloromethane, chloroform, or the like, preferably methanol. The reaction can be carried out without solvent.

The reaction temperature is usually from 0 to 100° C., preferably from 0 to 60° C. The reaction time is different depending on a starting material, solvent, reaction temperature, etc., though, usually from 10 hours to 1 month, preferably from 10 hours to 2 weeks.

(c) The partial hydrolysis of the diester (XIX) is carried out using a base in an equivalent mole. The base used has no special restriction if it is used in a usual reaction, though, it is an inorganic base such as sodium hydroxide, potassium hydroxide, sodium carbonate or the like. The reaction solvent has no special restriction if it does not hinder the proceeding of the reaction and dissolves a starting material, though, examples cited are alcohols, DMF, DMAc, dichloromethane, chloroform, or the like, preferably methanol. The reaction temperature is usually from −20 to 50° C., preferably from −5 to 5° C. The reaction time is different depending on a starting material, solvent, reaction temperature, etc., though, usually from 10 min. to 24 hours, preferably from 30 min. to 5 hours.

(d) The reaction for the preparation of the preparation intermediate (II), for example, via the acid anhydride (XXI) from the dicarboxylic acid (XX) can be carried out [J. Org. Chem., 47, 4928 (1982)]. Alcohols reacting with the acid anhydride (XXI) has no special restriction, though, they are methanol, ethanol, n-propyl alcohol, iso-propyl alcohol, tert-butyl alcohol, phenol, benzyl alcohol, phenacyl alcohol, 2,2,2-trichloroethanol or the like, preferably, methanol, ethanol, benzyl alcohol or 2,2,2-trichloroethanol.

(f) For preparing the preparation intermediate (II) by hydrogenating the propene acid derivative (X) preferable is the compound (X) in which $R^7$ is tert-butyl group and $R^9$ is benzyl group.

As the hydrogenation catalyst can be used catalysts such as palladium-carbon, platinum, or the like, though, preferably palladium-carbon. As the reaction solvent can be used an inactive organic-solvent such as alcohols (methanol, ethanol, etc.), DMF, DMAc or acetic acid, which are not catalytic poison, or water, preferably methanol or acetic acid. The reaction temperature is usually from 0 to 50° C., preferably from 10 to 30° C. The reaction time is different depending on a starting material, solvent, reaction temperature, etc., though, usually from 1 to 24 hours, preferably from 1 to 6 hours.

In the following, the preparation process of the preparation intermediate (III) is explained.

Synthetic route of intermediate (III)

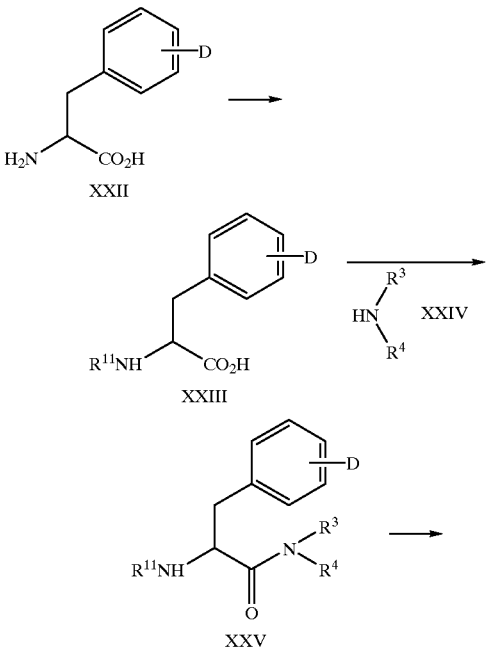

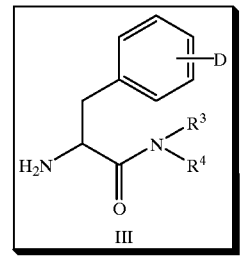

(In the above synthetic route, $R^3$ and $R^4$ have the same meaning described above, $R^{11}$ is an aminoprotecting group such as tert-butyloxycarbonyl (Boc), benzyloxycarbonyl (Z) or substituted Z groups, etc., and D has the same meaning as that of $R^5$ or is a hydrogen atom, or hydroxyl, protected phosphoric acid, protected diphosphonomethine, protected dicarboxymethine, nitro, amino, protected guanido, protected guanidomethylene, cyano, aminomethylene or protected amidino groups.)

In the above each intermediate, the timing of converting the compounds whose D is a hydrogen atom, or hydroxyl, nitro or cyano groups into the compound having a desirable functional group such as sulfuric acid, sulfonic acid, phosphoric acid, phosphonic acid, protected or non-protected guanido, amino, aminomethylene, acylimidoylaminomethylene, ($C_1$–$C_6$) acylamidoaminomethylene or protected or non-protected amidino groups, etc., is different depending on the characteristics of each functional group. For example, (a) in case of sulfonic acid group, it can be prepared by the sulfonation of 4' position of phenylalanine [see Helv. *Chim. Acta*, 66, 1335 (1983)]. (b) Thecase of sulfuric acid group canbeprepared by reacting the hydroxyl group of tyrosine with pyridine-sulfur trioxide complex. Further, (c) the case in which D is the protected guanido group can be prepared by hydrogenizing the general formula (XXV) having nitro group, converting to amino group, and then by reacting with 1H-pyrazole-N,N'-bisbenzyloxycarbonyl-1-carboxamidine.

(b) As the reaction solvent of the sulfurization, there is no special restriction if it does not hinder the proceeding of the reaction and dissolve the starting material, though, examples cited are alcohols, DMF, DMAc, ethyl acetate, diethyl ether, pyridine or the like, preferably DMF, DMAc or pyridine. The reaction temperature is usually from −10 to 40° C., preferably from −5 to 20° C. The reaction time is different depending on solvent, reaction temperature, etc., though, usually from 30 min. to 24 hours, preferably from 1 to 4 hours.

(c) In the case of the conversion into a protected guanido group, as the hydrogenation catalyst hydrogenizing nitro group can be used catalyst such as palladium-carbon, platinum or the like, preferably palladium-carbon. As the reaction solvent can be used an inactive organic-solvent such as alcohols (methanol, ethanol, etc.), DMF, DMAc or acetic acid, which are not catalytic poison, or water, preferably methanol. The reaction temperature is usually from 0 to 50° C., preferably from 10 to 30° C. The reaction time is different depending on a starting material, solvent, reaction temperature, etc., though, usually from 1 to 24 hours, preferably from 1 to 6 hours. Subsequently, for reacting with 1H-pyrazole-N,N'-bis-benzyloxycarbonyl-1-carboxamidine as the reaction solvent is used an inactive organic-solvent such as n-hexane, benzene, toluene, DMF, DMAc, dichloromethane, chloroform, or the like, though, preferably dichloromethane. The reaction temperature is usually from −10 to 50° C., preferably from 0 to 30° C. The reaction time is different depending on a starting material, solvent, reaction temperature, etc., though, usually from 10 min. to 12 hours, preferably from 30 min. to 6 hours.

The general formula (XXIII) can be prepared by introducing a protecting group such as Boc, Z or substituted Z groups or the like to the amino group of the general formula (XXII) by a conventional method.

For example, the case of Z group can be introduced by reacting chlorobenzyl formate in the presence of a base used conventionally (sodium carbonate, potassium carbonate, sodium bicarbonate, sodium hydroxide, potassium hydroxide).

As the reaction solvent can be cited dioxane, acetone, water or a mixed solvent thereof. The reaction temperature is usually from −20 to 30° C., preferably from −5 to 5° C. The reaction time is usually from 2 to 24 hours, preferably from 6 to 15 hours.

The general formula (XXV) can be prepared by reacting the general formula (XXIII) with the amine of the general formula (XXIV) according to a conventional coupling technology ($R^3$ has the same meaning described above, though, preferably hydrogen atom. $R^4$ has the same meaning described above, though, preferably a ($C_1$–$C_4$) alkyl group or an aryl group which can be substituted, more preferably methyl, phenyl, p-methoxyphenyl or 1-naphthyl.).

As the condensation agent can be used DCC, EDC.HCl, N-ethoxycarbonyl-2-ethoxy-1,2-dihydroquinoline (EEDQ), 1-hydroxybenzotriazole (HOBt) derivative, N-hydroxy-5-norbornene-2,3-dicarboximide (HONB) derivative, N-hydroxysuccinimide (HOSu) derivative, iso-butyloxycarbonyl chloride, monoalkylcarbonate derivative produced by reacting with ethyloxycarbonyl chloride, diphenylphosphoryl azide (DPPA) or the like, though, preferably EDC.HCl. As the reaction solvent, there is no special restriction if it does not hinder the proceeding of the reaction and dissolve the starting material, though, examples cited are DMF, DMAc, ethyl acetate, diethyl ether, dichloromethane, chloroform, dioxane or the like, preferably DMF.

The reaction temperatureisusually from −20 to 20° C., preferably from −15 to 0° C.

The reaction time is usually from 1 to 24 hours, preferably from 2 to 15 hours.

The intermediate (III) can be prepared by removing the amino-protecting group of the general formula (XXV). A conventional method is applied corresponding to a removing method and its type. For example, in the case that the protecting group is Z group, the hydrogenation method is a preferable one. As a hydrogenation catalyst can be used catalysts such as palladium-carbon, platinum or the like as a hydrogenation catalyst, though, preferably palladium-carbon. As the reaction solvent can be used an inactive organic-solvent such as alcohols (methanol, ethanol, etc.), DMF, DMAc or acetic acid, which are not catalytic poison, or water, preferably methanol. The reaction temperature is usually from 0 to 50° C., preferably from 10 to 30° C.

The reaction time is different depending on a starting material, solvent, reaction temperature, etc., though, usually from 1 to 24 hours, preferably from 1 to 6 hours.

In the following, the preparation process of the preparation intermediates (IV), (V), (VI), (VII) and the target compounds (I) is explained.

Synthetic routes of intermediates (IV), (V), (VI), (VII) and the target compounds (I)

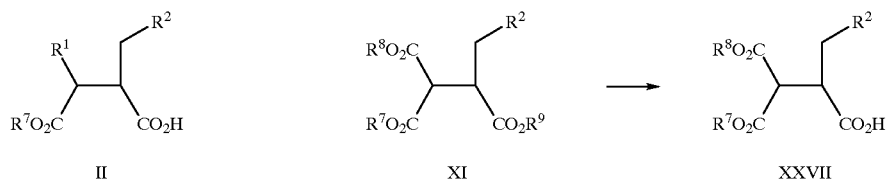

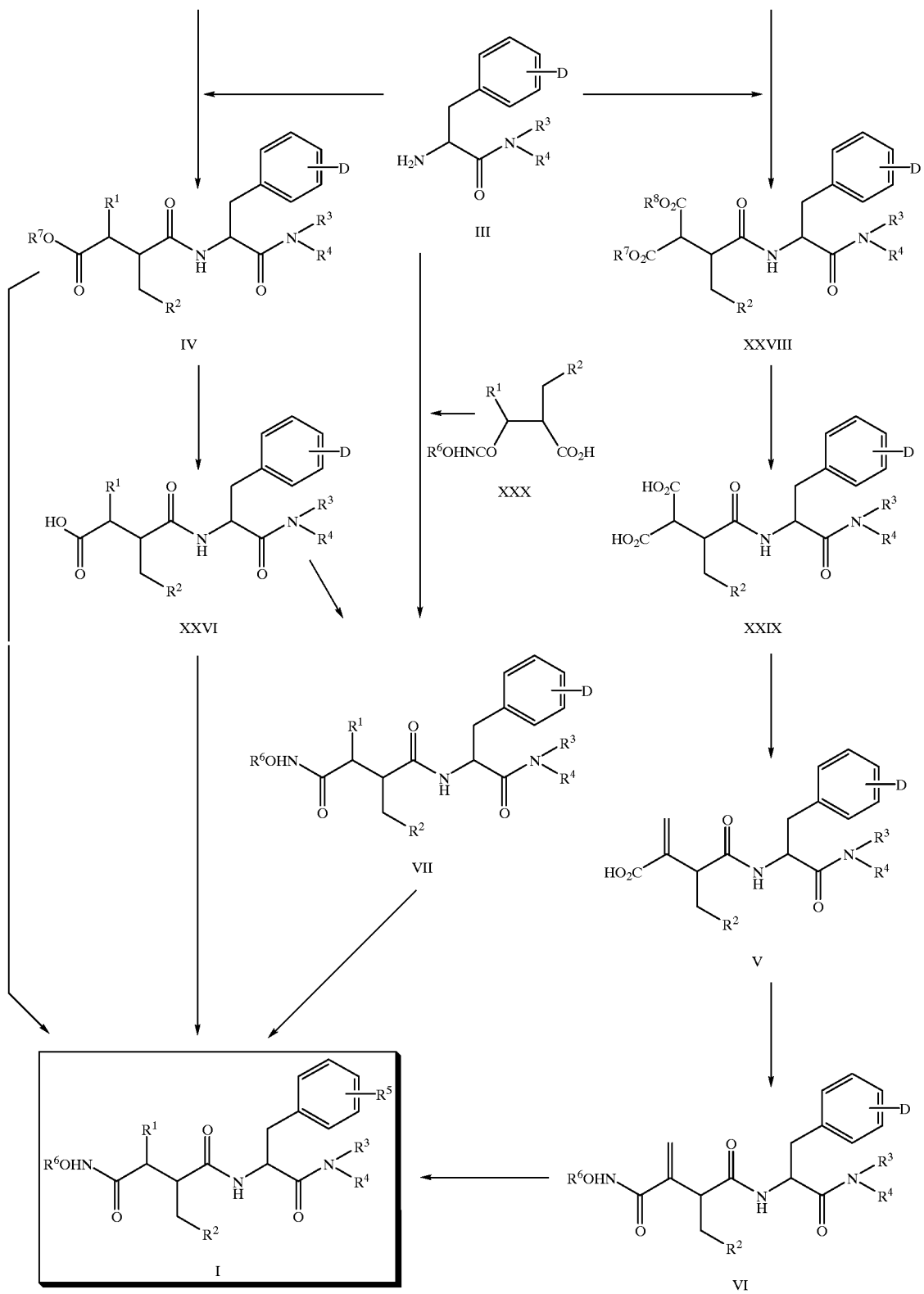

(In the above synthetic route, $R^1$, $R^2$, $R^3$, $R^4$, $R^5$, $R^6$, $R^7$, $R^8$, $R^9$ and D have the same meaning described above.)

The compound of the general formula (IV) can be prepared by reacting the preparation intermediate (II) with the preparation intermediate (III) according to a conventional coupling technology ($R^7$ has the same meaning described above, though, preferably tert-butyl, benzyl, substituted benzyl, phenacyl or 2,2,2-trichloroethyl groups, especially tert-butyl or benzyl groups.).

As the condensation agent used in this reaction can be cited DCC, EDC.HCl, EEDQ, HOBt derivative, HONB derivative, HOSu derivative, iso-butyloxycarbonyl chloride, monoalkylcarbonate derivative produced by reacting with ethyloxycarbonyl chloride, DPPA or the like, though, preferably EDC.HCl.

As the reaction solvent, there is no special restriction if it does not hinder the proceeding of the reaction and dissolve the starting material, though, examples cited are DMF, DMAc, ethyl acetate, diethyl ether, dichloromethane, chloroform, dioxane or the like.

The reaction temperature is usually from −20 to 20° C., preferably from −15 to 0° C. The reaction time is usually from 1 to 24 hours, preferably from 2 to 15 hours.

The compound of the general formula (XXVI) can be prepared by the deesterification of the compound of the general formula (IV). For example, in case of the tert-butyl ester, the deesterification can be carried out by the treatment with trifluoroacetic acid (TFA) or a solution, whereby hydrogen chloride is dissolved in ethyl acetate or dioxane.

The reaction temperature is usually from −10 to 20° C., preferably from −5 to 50° C. The reaction time is different depending on a startingmaterial, acid, reaction temperature, etc., though, usually from 1 to 24 hours, preferably from 1 to 15 hours.

The compound of the general formula (XXVII) can be prepared by deesterifying the compound of the formula (XI). In order to obtain the compound of the general formula (XXVII), it is preferable that $R^7$ and $R^8$ are benzyl groups and $R^9$ is tert-butyl group.

For example, the deesterification of tert-butyl ester group can be carried out by the treatment with TFA or a solution, whereby hydrogen chloride is dissolved in ethyl acetate or dioxane.

The reaction temperature is usually from −10 to 20° C., preferably from −5 to 5° C. The reaction time is different depending on a starting material, acid, reaction temperature, etc., though, usually from 1 to 24 hours, preferably from 1 to 15 hours.

The compound of the general formula (XXVIII) can be prepared by reacting the compound of the formula (XXIII) with the preparation intermediate (III) according to a conventional coupling technology.

As the condensation agent used can be cited DCC, EDC.HCl, EEDQ, HOBt derivative, HONB derivative, HOSu derivative, iso-butyloxycarbonyl chloride, monoalkylcarbonate derivative produced by reacting with ethyloxycarbonyl chloride, DPPA or the like, though, preferably EDC.HCl.

As the reaction solvent, there is no special restriction if it does not hinder the proceeding of the reaction and dissolve the starting material, though, examples cited are DMF, DMAc, ethyl acetate, diethyl ether, dichloromethane, chloroform, dioxane or the like, preferably DMF.

The reaction temperature is usually from −20 to 20° C., preferably from −15 to 0° C. The reaction time is usually from 1 to 24 hours, preferably from 2 to 15 hours.

The general formula (XXIX) can be prepared by deesterifying two ester groups of the formula (XXVIII).

In order to obtain the compound of the general formula (XXIX), it is preferable that $R^7$ and $R^8$ of the formula (XXVIII) are benzyl groups. In the case that $R^7$ and $R^8$ are benzyl groups, the debenzylation can be carried out easily by a hydrogenation method. As a hydrogenation catalyst can be used catalysts such as palladium-carbon, platinum or the like as a hydrogenation catalyst, though, preferably palladium-carbon.

As the reaction solvent can be used an inactive organic-solvent such as alcohols (methanol, ethanol, etc.), DMF, DMAc or acetic acid, which are not catalytic poison, or water, preferably methanol.

The reaction temperature is usually from 0 to 50° C., preferably from 10 to 30° C.

The reaction time is different depending on a starting material, solvent, reaction temperature, etc., though, usually from 1 to 24 hours, preferably from 1 to 6 hours.

The compound of the synthetic intermediate (V) can be prepared by reacting the Schiff base, resulting from formaline and a secondary amine such as piperidine, diethylamine, morpholine or the like (preferably piperidine), with the general formula (XXIX), followed by the decarboxylation and the simultaneous double-bond formation.

As the reaction solvent, there is no special restriction if it does not hinder the proceeding of the reaction and dissolve the starting material, though, examples cited are alcohols, DMF, DMAc or the like, preferably methanol or ethanol.

The reaction temperature is usually from 0 to 150° C., preferably from 10 to 100° C. The reaction time is different depending on a starting material, solvent, reaction temperature, etc., though, usually from 1 to 24 hours, preferably from 1 to 15 hours.

The general formula (VI) can be prepared by reacting the hydroxylamine, in which carboxyl and hydroxyl groups in the preparation intermediate (V) are protected, using a conventional coupling technology (as a hydroxyl-protecting group can be cited nonsubstituted or substituted benzyl, trialkylsilyl, tert-butyldiphenylsilyl, tetrahydropyranyl or tert-butyl groups, or the like, preferably benzyl group.).

As the condensation agent used can be cited DCC, EDC.HCl, EEDQ, HOBt derivative, HONB derivative, HOSu derivative, iso-butyloxycarbonyl chloride, monoalkylcarbonate derivative produced by reacting with ethyloxycarbonyl chloride, DPPA or the like, though, preferably EDC.HCl.

As the reaction solvent, there is no special restriction if it does not hinder the proceeding of the reaction and dissolve the starting material, though, examples cited are DMF, DMAc, ethyl acetate, diethyl ether, dichloromethane, chloroform, dioxane or the like, preferably DMF.

The reaction temperature is usually from −20 to 20° C., preferably from −15 to 0° C. The reaction time is usually from 1 to 72 hours, preferably from 2 to 48 hours.

The general formula (VII) can be prepared by (a) reacting the preparation intermediate (III) and the formula (XXX) by a conventional coupling technology, or (b) reacting the carboxylic acid of the formula (XXVI) with the hydroxylamine, in which the hydroxyl group is protected, by a conventional coupling technology (As a hydroxyl-protecting group can be cited nonsubstituted or substituted benzyl, trialkylsilyl, tert-butyldiphenylsilyl, tetrahydropyranyl or tert-butyl groups, or the like, preferably benzyl group.).

(a), (b) As the condensation agent used can be cited DCC, EDC.HCl, EEDQ, HOBt derivative, HONB derivative, HOSu derivative, iso-butyloxycarbonyl chloride, monoalkylcarbonate derivative produced by reacting with ethyloxycarbonyl chloride, DPPA or the like, though, preferably EDC.HCl.

As the reaction solvent, there is no special restriction if it does not hinder the proceeding of the reaction and dissolve the starting material, though, examples cited are DMF, DMAc, ethyl acetate, diethyl ether, dichloromethane, chloroform, dioxane or the like, preferably DMF. The reaction temperature is usually from −20 to 20° C., preferably from −15 to 0° C. The reaction time is usually from 1 to 72 hours, preferably from 2 to 48 hours.

The general formula (XXX) can be prepared by the addition reaction of the hydroxylamine, in which the hydroxyl group is protected, to the acid anhydride (XXI).

As the reaction solvent, there is no special restriction if it does not hinder the proceeding of the reaction and dissolve the starting material, though, examples cited are DMF, DMAc, ethyl acetate, diethyl ether, benzene, toluene, dichloromethane, chloroform, dioxane or the like, preferably DMF. The reaction temperature is usually from −20 to 20° C., preferably from −10 to 10° C. The reaction time is usually from 1 to 24 hours, preferably from 2 to 15 hours.

The compound of the general formula (I) can be prepared by (a) removing the protecting group of the general formula (VII), (b) removing the hydroxyl-protecting group after adding a thiol derivative to the general formula (VI), (c) reacting the carboxylic acid of the general formula (XXVI) with hydroxylamine or its salt by a conventional coupling technology or (d) the aminolysis of the ester of the general formula (IV) by hydroxylamine.

(a) As a method to remove the hydroxyl-protecting group, in the case that the protecting group is benzyl group, whereby it can be removed by a conventional hydrogenation method, however, in the case that sulfur atom is present in the molecule, whereby hydrofluoric acid is preferably used for the debenzylation.

In case of removing benzyl group by the hydrogenation method, as a hydrogenation catalyst can be used catalysts such as palladium-carbon, platinum or the like as a hydrogenation catalyst, though, preferably palladium-carbon.

As the reaction solvent can be used an inactive organic-solvent such as alcohol (methanol, ethanol, etc.), DMF, DMAc or acetic acid, which are not catalytic poison, or water, preferably methanol or acetic acid.

The reaction temperature is usually from 0 to 50° C., preferably from 10 to 30° C.

The reaction time is different depending on the starting material, solvent, reaction temperature, etc., though, usually from 1 to 24 hours, preferably from 1 to 6 hours.

In case of treating with hydrofluoric acid, as a scavenger is added anisole, dimethyl sulfide, ethanedithliol, methionine or the like.

The reaction temperature is usually from −40 to 30° C., preferably from −5 to 5° C. The reaction time is different depending on a starting material, reaction temperature, etc., though, usually from 10 min. to 3 hours, preferably from 30 min. to 1 hour.

(b) In the method in which a thiol derivative is added to the general formula (VI), there is no special restriction for the reaction solvent if it does not hinder the proceeding of the reaction and dissolve the starting material, though, examples cited are alcohols, DMF, DMAc, dichloromethane, chloroform or the like, preferably methanol. Further, the reaction can be done without solvent.

The reaction temperature is usually from 0 to 100° C., preferably from 0 to 60° C. The reaction time is largely different depending on the starting material, solvent, reaction temperature, etc., though, usually from 10 hours to 1 month, preferably from 10 hours to 2 weeks.

Next, in the method to remove a hydroxyl-protecting group is applied the method to treat with hydrofluoric acid when the protecting group is benzyl group. In case of treating with hydrof luoric acid, as a scavenger is added anisole, dimethyl sulfide, ethanedithiol, methionine or the like.

The reaction temperature is usually from −40 to 30° C., preferably from −5 to 5° C. The reaction time is different depending on a starting material, reaction temperature, etc., though, usually from 10 min. to 3 hours, preferably from 30 min. to 1 hour.

(c) In the method that the carboxylic acid of the formula (XXVI) and hydroxylamine and salts thereof are reacted according to a conventional coupling technology, as the condensation agent used can be cited DCC, EDC.HCl, EEDQ, HOBt derivative, HONB derivative, HOSu derivative, iso-butyloxycarbonyl chloride, monoalkylcarbonate derivative produced by reacting with ethyloxycarbonyl chloride, DPPA or the like, though, preferably EDC.HCl.

As the above reaction solvent, there is no special restriction if it does not hinder the proceeding of the reaction and dissolve the starting material, though, examples cited are DMF, DMAc, ethyl acetate, diethyl ether, dichloromethane, chloroform, dioxane or the like, preferably DMF. The reaction temperature is usually from −20 to 20° C., preferably from −15 to 0° C. The reaction time is usually from 1 to 24 hours, preferably from 2 to 15 hours.

(d) In the aminolysis of the ester of the formula (IV) by hydroxylamine, there is no special restriction for the reaction solvent if it does not hinder the proceeding of the reaction and dissolve the starting material, though, examples used are alcohols (methanol, ethanol, etc.), DMF, DMAc, ethyl acetate, diethyl ether, dichloromethane, chloroform, dioxane or the like, preferably alcohols.

The reaction temperature is usually from −30 to 200° C., preferably from −10 to 30° C. The reaction time is different depending on the starting material, reaction temperature, etc., though, usually from 10 min. to 24 hours, preferably from 30 min. to 10 hours. Further, if the reaction does not proceed easily, it is possible to let it proceed by the pressurization.

Diseases concerned with a tissue destruction to which the compounds obtained by the invention are applied, mean chronic rheumatoid arthritis, osteoarthritis, periodental disease, corneal ulcer, various kinds of bullosis (epidermolisis bullosahereditaria, epidermolisis bullosa acquisita, porphylia cutanea tarda, bullos penphigoid, pemphigus vulgaris), intractable skin ulcer (bedsore, skin ulcer in radiotherapy, skin ulcer in diabetes mellitus, skin ulcer in arteriosclerotic obliteration), wound (external injury or burn), osteoporosis, cancer metasis and the like. The compounds obtained by the invention are, for example, N-[4-(N-Hydroxyamino)-2(R or S)-isobutylsuccinyl]-O-sulfo-L-tyrosine-N-methylamide, monosodium salt;

N-[4-(N-Hydroxyamino)-2(RS)-isobutylsuccinyl]-L-4'-sulfophenylalanine-N-methylamide, monosodium salt;

N-[4-(N-Hydroxyamino)-2(R)-isobutyl-3(R or S)-(3-phenyltrimethylene)succinyl]-O-sulfo-L-tyrosine-N-methylamide, monosodium salt;

N-[4-(N-Hydroxyamino)-2(R)-isobutyl-3(RS)-(3-phenyltrimethylene)succinyl]-L-4'-sulfophenylalanine-N-methylamide, monosodium salt;

N-[4-(N-Hydroxyamino)-2(R)-isobutyl-3(R or S)-(thienylthiomethylene)succinyl]-L-4'-sulfophenylalanine-N-methylamide, monosodium salt;

N-[4-(N-Hydroxyamino)-2(R)-n-propyloxymethlene-3(RS)-isopropylthiomethylenesuccinyl]-L-4'-sulfophenylalanine-N-methylamide, monosodium salt;

N-[4-(N-Hydroxyamino)-2(R)-isobutyl-3(RS)-(3-phenyltrimethylene)succinyl]-O-sulfo-L-tyrosine-N-p-methoxyphenylamide, monosodium salt;

N-[4-(N-Hydroxyamino)-2(R)-isobutyl-3(R or S)-(3-phenyltrimethylene)succinyl]-L-4'-guanidophenyl-alanine-N-methylamide monoacetate;

N-[4-(N-Hydroxyamino)-2(R)-isobutylsuccinyl]-O-phospho-L-tyrosine-N-methylamide, disodium salt;

N-[4-(N-Hydroxyamino)-2(R)-isobutyl-3(R or S)-(3-phenyltrimethylene)succinyl]-L-4'-acetimidoyl-iminomethylenephenylalanine-N-methylamide monoacetate;

N-[4-(N-Hydroxyamino)-2(R)-isobutyl-3(R or S)-(3-phenyltrimethylene)succinyl]-L-4'-propionimidoyl-iminomethylenephenylalanine-N-methylamide monoacetate;

N-[4-(N-Hydroxyamino)-2(R)-isobutyl-3(RS)-(3-phenyltrimethylene)succinyl]-L-4'-benzimidoyl-iminomethylenephenylalanine-N-methylamide monoacetate;

N-[4-(N-Hydroxyamino)-2(R)-isobutyl-3(RS)-(3-phenyltrimethylene)succinyl]-L-4'-acetamido-methylenephenylalanine-N-methylamide;

N-[4-(N-Hydroxyamino)-2(R)-isobutyl-3(RS)-(3-phenyltrimethylene)succinyl]-L-4'-guanido-methylenephenylalanine-N-methylamide monoacetate;

N-[4-(N-Hydroxyamino)-2(R)-isobutyl-3(R or S)-(3-phenyltrimethylene)succinyl]-O-sulfo-L-meta-tyrosine-N-methylamide, monosodium salt;

N-[4-(N-Hydroxyamino)-2(R)-isobutyl-3(S)-hydroxysuccinyl]-L-4'-guanidophenylalanine-N-methylamide monoacetate;

N-[4-(N-Hydroxyamino)-2(R)-isobutyl-3(R or S)-(3-phenyltrimethylene)succinyl]-L-4'-amidino-phenylalanine-N-methylamide monoacetate;

N-[4-(N-Hydroxyamino)-2(R)-isobutyl-3(RS)-(3-phenyltrimethylene)succinyl]-O-sulfo-L-tyrosine-N-1-naphthylamide, monosodium salt;

N-[4-(N-Hydroxyamino)-2(R)-isobutyl-3(RS)-(3-phenyltrimethylene)succinyl]-L-4'-guanido-phenylalanine-N-phenylamide monoacetate, etc.

These compounds have excellent inhibitory activities for MMPs and/or TNF-α converting enzyme, and additionally, the water-solubility thereof was conspicuously increased compared with the compounds known previously. Consequently, these compounds are not only easy for the application to the diseases concerned with the tissue destruction, but also are useful compounds by which the treatment and/or a preventive effect can be expected.

In the following are explained assay methods for biological activities of the compounds according to the inventions, their pharmaceutical preparations, dose, etc.

Inhibitory activities of the compounds represented by the general formula (I) according to the invention for collagenase (metalloproteinase concerned with a tissue destruction) derived from human fibroblast were tested by the method of Y. Murawaki et al., [*Journal of Hepatology*, 18, p. 328–334 (1993)], and their inhibitory activities for stromelysin derived from human fibroblast were measured by the method of S. S. Twining et al., [*Anal. Biochem.*, 143, p. 30 (1984)]. The test results are described below as test examples.

The compounds of the general formula (I) can be administered by any of dosage forms such as oral, topical, parenteral administration or the like. As those corresponding to these dosage forms, they are provided in forms such as tablets, capsules, powders, granules, fluids or gel preparation. In the tablets or the capsules for oral administration, the dosage unit is in a written form, and they can be let include usual additives shown below by using a conventional method. The tablets can be coated according to the well-known method in a conventional pharmaceutical operation.

(1) Binders such as liquid glucose, acacia, gelatin, methyl cellulose, povidone or the like;

(2) Excipients such as lactose, starch, calcium phosphate, sorbitol or the like;

(3) Lubricants, for example, such as magnesium stearate, talc, polyethylene glycol or the like;

(4) Disintegraters such as starch and wetting agents such as sodium laurylsulfate.

Oral liquid preparations are composed in forms, for example, such as suspensions, solutions, emulsions, syrups or elixirs, containing water or oil portions, or are provided as a dry product to be converted to a liquid state by adding water or the other excipients.

These liquid preparations can include suspension agents, for example, such as tragacanth, polyvinyl alcohol, methyl cellulose or gelatin; emulsifiers, for example, such as lecithin, sorbitan ester or acacia; plasticizers, for example, such as glycerin, propylene glycol, antimicrobial preservatives or sterilizing preservatives, for example, such as methylparaben or propylparaben, or usual additives like sorbic acid and, if necessary, also usual sweeteners or colorings.

The dosage unit of oral administration is about 0.1–500 mg, and preferably, it contains about 1–250 mg of a compound of the general formula (I) The appropriate daily dose is largely different depending on the state of a patient, though, appropriate doses of a compound of the general formula (I) are 0.001–300 mg/Kg body weight, especially 0.01–100 mg/Kg body weight.

Pharmaceutical substances for topical application to skin can be prepared as solutions or suspension liquids by sterile water or nonaqueous excipients. As additives are cited, for example, buffer substances such as citric acid, sodium citrate (dihydrate or anhydride) or edetate salts; preservatives containing antiseptic agents or antimicrobial agents such as phenylmercuric nitrate, benzalkonium chloride or chlorhexidine, and tackifiers like hydroxypropyl methyl cellulose. The dosage for topical administration is different depending on the size of a part treated, though, the dosage unit for eye (one eye) is in a range of 0.1–100 mg of a compound of the general formula (I). An active ingredient can be administered parenterally by using sterile vehicles.

Pharmaceutical substances can be suspended or dissolved in excipients according to the excipients used and the concentration thereof. Auxiliaries such as local anesthetic agents, preservatives and buffer substances are soluble in exicipients. Concerning the use for the treatment of arthritis such as osteoarthritis and chronic rheumatoid arthritis, compounds of the invention can be administered orally or by injecting into diseased joint intraarticularly. The daily dosage for mammal of body weight, 70 Kg, is in a range of 0.1–10 g of a compound of the general formula (I).

In the following, the invention will be explained in more detail by showing examples, test examples and preparations' example, but the invention is not limited thereby in any way. The abbreviations described below are used in the examples as they are understood to mean the followings. Further, specific rotation was measured at 25° C.

DMF; N,N-dimethylformamide, DMSO; dimethylsufoxide, EDC; 1-(3-dimethylaminopropyl)-3-ethylcarbodiimide hydrochloride, HOBT; 1-hydroxybenzotriazole, TEA; triethylamine, THF; tetrahydrofuran.

EXAMPLE 1

N-[4-(N-Hydroxyamino)-2(R or S)-isobutylsuccinyl]-O-sulfo-L-tyrosine-N-methylamide, Monosodium Salt (a) Benzyl 2-isobutyl-3-tert-butoxycarbonylpropenoate To a suspension of 60% NaH (3.60 g, 90.0 mmol) in anhydrous THF (100 ml), which was stirred under ice-cooling and nitrogen atmosphere, was dropped (tert-butoxycarbonylmethylene) triphenylphosphrane (22.8 g, 90.4 mmol). After stirring under ice-cooling for 30 min., the mixture was added with benzyl 4-methyl-2-oxopentanoate (13.0 g, 59.0 mmol) and stirred at room temperature overnight. The reaction mixture was added with Et$_2$O (300 ml) and washed with water and then with a saturated aqueous solution of NaCl two times respectively. The organic layer was dried over anhydrous MgSO$_4$, evaporated under reduced pressure and purified by column chromatography (silica gel; 500 g, elution with the mixed solvent; n-hexane: AcOEt=20:1), giving the title compound (15.3 g, 81%) of a colorless oil.

Rf value; 0.37 (AcOEt:n-hexane=1:10).

$^1$H-NMR(CDCl$_3$) δ ppm; 0.88 (6H, d, J=6.5 Hz, CH (CH$_3$)$_2$), 1.43 (9H, s, (CH$_3$)$_3$C), 1.5–1.9 (1H, m, (CH$_3$)$_2$ CH—CH$_2$), 2.22 (2H, bd, J=7.2 Hz, (CH$_3$)$_2$CH—CH$_2$), 5.22 (2H, s, O—CH$_2$), 7.37 (5H, s, aromatic-H).

(b) 2(RS)-Isobutyl-3-tert-butoxycarbonylpropanoic Acid

The compound (15.0 g, 47.1 mmol) of Example 1-a was dissolved in AcOH (200 ml). The solution was added with 10% Pd-C (50%, 10.0 g) and then stirred vigorously in a stream of hydrogen at room temperature for 5 hours. After the catalyst was filtered off, the solvent was removed under reduced pressure to give the title compound (10.8 g, in quantitative yield) of a colorless oil.

$^1$H-NMR(CDCl$_3$) δ ppm; 0.7–1.0 (6H, m, CH(CH$_3$)$_2$), 1.1–1.8 (12H, m, (CH$_3$)$_2$CH—CH$_2$+C(CH$_3$)$_3$), 2.44 (2H, dd, J=10, 8 Hz, CH$_2$—COOC(CH$_3$)$_3$), 2.8 (1H, m, CH—CO), 8.4 (1H, brs, COOH).

(c) N-[4-tert-Butoxy-2(R or S)-isobutylsuccinyl]-L-tyrosine-N-methylamide

The compound (4.60 g, 20.0 mmol) of Example 1-b, L-tyrosine-N-methylamide hydrochloride (4.90 g, 21.4 mmol), HOBT (5.40 g, 40.0 mmol) were dissolved in DMF (30 ml) and CH$_2$Cl$_2$ (10 ml), and the solution was added with TEA (3.10 ml, 22.1 mmol) and EDC (5.00 g, 26.1 mmol) under stirring at −15° C. The mixture was stirred at −15° C. for 1 hour and further at room temperature overnight and evaporated under reduced pressure. The residue was added with AcOEt (300 ml) and washed with a saturated aqueous solution of NaCl, 1N-HCl, a saturated aqueous solution of NaHCO$_3$ and then the saturated aqueous solution of NaCl two times respectively. The organic layer was dried over anhydrous MgSO$_4$ and evaporated under reduced pressure. The residue was added with Et$_2$O (150 ml), giving crystals (2.55 g, 32%, one isomer of the title compounds: designating isomer A). The filtrate was evaporated under reduced pressure and purified by column chromatography separation (silica gel; 250 g, elution with the mixed solvent; n-hexane: AcOEt1:2), giving the title compound (3.70 g, 46%, the other isomer of the title compounds: designating isomer B) of a pale yellow solid.

Isomer A m.p.; 211° C., specific rotation[α]$_D$=−18.2° (c=1.0, MeOH), Rf value; 0.63 (CHCl$_3$:MeOH:AcOH=95:5:3).

$^1$H-NMR(CDCl$_3$) δ ppm; 0.75 (6H, d, J=4.6 Hz, CH (CH$_3$)$_2$), 0.8–1.7 (12H, s+m, (CH$_3$)$_2$CH—CH$_2$+C(CH$_3$)$_3$), 2.0–3.5 (8H, d+m, J=4.6 Hz, N—CH$_3$+CO—CH$_2$CH—CO+ CH$_2$—C$_6$H$_4$), 4.7 (1H, m, NH—CH—CO), 6.6, 7.4 (1H×2, m, NH×2), 6.87 (4H, AA'BB', aromatic-H).

Isomer B m.p.; 62° C., specific rotation[α]$_D$=−4.0° (c=1.1, MeOH), Rf value; 0.63 (CHCl$_3$:MeOH:AcOH=95:5:3).

$^1$H-NMR(CDCl$_3$) δ ppm; 0.85 (6H, m, CH(CH$_3$)$_2$), 1.0–1.8 (12H, s+m, (CH$_3$)$_2$CH—CH$_2$+C(CH$_3$)$_3$), 2.3–2.8 (7H, d+m, J=4.6 Hz, N—CH$_3$+CH$_2$COO+CH$_2$—C$_6$H$_4$), 3.0 (1H, m, CH—CO), 4.5 (1H, m, NH—CH—CO), 5.9, 6.3 (1H×2, m, NH×2), 6.90 (4H, AA'BB', aromatic-H).

(d) N-[4-(N-Hydroxy)-2(R or S)-isobutylsuccinyl]-L-tyrosine-N-methylamide

The compound (isomer B, 3.50 g, 8.60 mmol) of Example 1-c was added with ice-cooled 95% aqueous trifluoroacetic acid (10 ml). The reaction mixture was stirred at 5° C. overnight and evaporated under reduced pressure. The residue was added with Et$_2$O. After stirring at room temperature for 1 hour, the crystallized solid was filtered to give the title compound (isomer B, 1.85 g, 61%) of a white solid upon drying.

Also from the compound (isomer A, 2.44 g, 6.00 mmol) of Example 1-c, the title compound (isomer A, 2.00 g, 95%) of a white solid was obtained by the similar procedure.

Isomer B m.p.; 214° C., specific rotation[α]$_D$=−0.2° (c=1.0, MeOH), Rf value; 0.17 (CHCl$_3$:MeOH:AcOH=95:5:3).

$^1$H-NMR(MeOH-d$_4$) δ ppm; 0.82 (6H, m, CH(CH$_3$)$_2$), 1.0–1.6 (3H, m, (CH$_3$)$_2$CH—CH$_2$), 2.1–3.5 (m, N—CH$_3$+CO—CH$_2$CH—CO+CH$_2$—C$_6$H$_4$), 4.43 (1H, m, NH—CH—CO), 6.85 (4H, AA'BB', aromatic-H).

Isomer A m.p.; 102° C., specific rotation[α]$_D$=−21.7° (c=1.1, MeOH), Rf value; 0.12 (CHCl$_3$:MeOH:AcOH=95:5:3).

$^1$H-NMR(MeOH-d$_4$) δ ppm; 0.5–1.5 (9H, m, (CH$_3$)$_2$CH—CH$_2$), 2.0–3.7 (m, N—CH$_3$+CO—CH$_2$CH—CO+CH—CO+CH$_2$—C$_6$H$_4$), 4.65 (1H, dd, J=5.3, 9.3 Hz, NH—CH—CO), 6.88 (4H, AA'BB', aromatic-H).

(e) N-[4-(N-Benzyloxyamino)-2(R or S)-isobutylsuccinyl]-L-tyrosine-N-methylamide The compound (isomer B, 3.51 g, 10.0 mmol) of Example 1-d, O-benzylhydroxylamine hydrochloride (3.20 g, 20.0 mmol) and HOBT (2.70 g, 20.0 mmol) were suspended in DMF (20 ml) and added with TEA (2.80 ml, 20.0 mmol) and EDC (3.80 g, 20.0 mmol) at −15° C. under stirring. The suspension was stirred at −15° C. for 1 hour and further at room temperature overnight and evaporated under reduced pressure. The residue was added with AcOEt (250 ml) and washed quickly with a saturated aqueous solution of NaCl, 1N-HCl, a saturated aqueous solution of NaHCO$_3$ and then the saturated aqueous solution of NaCl two times respectively. The organic layer was dried over anhydrous MgSO$_4$ and evaporated under reduced pressure. The residue was added with Et$_2$O and stirred at room temperature for 1 hour. The crystallized solid was filtered to give the title compound (isomer B, 3.90 g, 86%) of a white solid upon drying in a desiccator under reduced pressure.

Also from the compound (isomer A, 2.44 g, 6.95 mmol) of Example 1-d, the title compound (isomer A, 2.40 g, 84%) of a white solid was obtained by the similar procedure.

Isomer B m.p.; 198° C., specific rotation[α]$_D$=−18.8° (c=1.1, MeOH), Rf value; 0.31 (CHCl$_3$:MeOH:AcOH=95:5:3).

$^1$H-NMR(MeOH-d$_4$+CDCl$_3$) δ ppm; 0.6–1.7 (9H, m, (CH$_3$)$_2$CH—CH$_2$), 2.08 (2H, bd, J=4.6 Hz, CH$_2$CO), 2.5–3.1 (6H, m, N—CH$_3$+CH—CO+CH$_2$—C$_6$H$_4$), 4.45 (1H, m, NH—CH—CO), 4.83 (2H, s, O—CH$_2$), 6.87 (4H, AA'BB', tyrosin(aromatic-H)), 7.31 (5H, s, aromatic-H).

Isomer A m.p.; 97° C., specific rotation[α]$_D$=−20.0° (c=1.0, MeOH), Rf value; 0.31 (CHCl$_3$:MeOH:AcOH=95:5:3).

$^1$H-NMR(MeOH-d$_4$+CDCl$_3$) δ ppm; 0.5–1.7 (9H, m, (CH$_3$)$_2$CH—CH$_2$), 1.9–3.5 (8H, m, N—CH$_3$+CO—CH$_2$CH—CO+CH$_2$—C$_6$H$_4$), 4.45–4.95 (3H, m, NH—CH—CO+O—CH$_2$), 6.9 (4H, AA'BB', tyrosine (aromatic-H)), 1.35 (5H, s, aromatic-H).

(f) N-[4-(N-Benzyloxyamino)-2(R or S)-isobutylsuccinyl]-O-sulfo-L-tyrosine-N-methylamide, Monosodium Salt The compound (isomer B, 1.50 g, 3.30 mmol) of Example 1-e was suspended in DMF (3.3 ml). The suspension was added with sulfur trioxide pyridine complex (1.60 g, 9.90 mmol) and stirred at room temperature for 1.5 hours. The reaction liquid was added with 1N-NaHCO$_3$ (80 ml), stirred at room temperature for 40 min. and then purified by a reverse-phase column chromatography (Fuji Silysia Chemical Ltd., Chromatorex ODS DM-1020T; 75 g, elution with a MeOH-water solution containing 0–50% MeOH) to give the title compound (isomer B, 1.60 g, 87%) of white amorphous powder upon freeze-drying.

Also from the compound (isomer A, 1.80 g, 3.95 mmol) of Example 1-e, the title compound (isomer A, 1.85 g, 84%) of white amorphous powder was obtained by the similar procedure.

Isomer B

Specific rotation[$\alpha$]$_D$=−14.7° (c=0.4, MeOH), Rf value; 0.87 (CHCl$_3$:MeOH:AcOH=5:2:1), 0.81 (n-BuOH:AcOH:water=4:1:1).

$^1$H-NMR(MeOH-d$_4$) $\delta$ ppm; 0.5–1.5 (9H, m, (CH$_3$)$_2$CH—CH$_2$), 1.9–3.0 (8H, m, N—CH$_3$+CO—CH$_2$CH—CO+CH$_2$—C$_6$H$_4$), 4.50 (m, NH—CH—CO), 7.20 (4H, s, tyrosine (aromatic-H)), 7.35 (5H, m, aromatic-H).

Isomer A

Specific rotation[$\alpha$]$_D$=−15.3° (c=1.0, MeOH), Rf value; 0.87 (CHCl$_3$:MeOH:AcOH=5:2:1), 0.81 (n-BuOH:AcOH:water=4:1:1).

$^1$H-NMR(MeOH-d$_4$) $\delta$ ppm; 0.82 (6H, m, (CH$_3$)$_2$CH—CH$_2$), 0.9–1.6 (3H, m, (CH$_3$)$_2$CH—CH$_2$), 2.0–3.0 (8H, m, CO—CH$_2$CH—CO+N—CH$_3$+CH$_2$—C$_6$H$_4$), 4.50 (1H, m, NH—CH—CO), 7.20 (4H, brs, tyrosine (aromatic-H)), 7.37 (5H, m, aromatic-H).

(g) N-[4-(N-Hydroxyamino)-2(R or S)-isobutylsuccinyl]-O-sulfo-L-tyrosine-N-methylamide, Monosodium Salt The compound (isomer B, 1.60 g, 2.87 mmol) of Example 1-f was dissolved in MeOH (100 ml). The solution was added with 10% Pd-C (50% wet, 0.50 g) and then stirred vigorously in a stream of hydrogen at room temperature for 1 hour. After the catalyst was filtered off, MeOH of the filtrate was removed under reduced pressure. The residue was added with water (50 ml) and lyophilized to give the title compound (isomer B, 1.22 g, 90%) of white amorphous powder.

Also from the compound (isomer A, 0.50 g, 0.90 mmol) of Example 1-f, the title compound (isomer A, 0.39 g, 92%) of white amorphous powder was obtained by the similar procedure.

Isomer B

Specific rotation[$\alpha$]$_D$=−7.5° (c=0.51, MeOH), Rf value; 0.58 (CHCl$_3$:MeOH:AcOH=5:2:1), 0.61 (n-BuOH:AcOH:water=4:1:1). Analytical value calculated for C$_{18}$H$_{26}$N$_3$O$_8$SNa. Theoretical value:C, 46.25; H, 5.61; N, 8.99. Found:C, 46.0; H, 5.83; N, 8.77.

$^1$H-NMR(MeOH-d$_4$) $\delta$ ppm; 0.83 (6H, m, (CH$_3$)$_2$CH—CH$_2$), 1.0–2.0 (3H, m, (CH$_3$)$_2$CH—CH$_2$), 2.08 (2H, m, CH$_2$CO), 2.5–3.1 (6H, m, CH—CO+N—CH$_3$+CH$_2$—C$_6$H$_4$), 4.50 (1H, m, NH—CH—CO), 7.70 (4H, s, aromatic-H).

Isomer A

Specific rotations[$\alpha$]$_D$=−8.1° (c=1.0, MeOH), Rf value; 0.55 (CHCl$_3$:MeOH:AcOH=5:2:1), 0.60 (n-BuOH:AcOH:water=4:1:1). Analytical value calculated for C$_{18}$H$_{26}$N$_3$O$_8$SNaH$_2$O. Theoretical value:C, 44.53; H, 5.81; N, 8.66. Found:C, 44.41; H, 5.88; N, 8.65.

$^1$H-NMR(MeOH-d$_4$+CDCl$_3$) $\delta$ ppm; 0.6–1.7 (9H, m, (CH$_3$)$_2$CH—CH$_2$), 1.9–3.5 (8H, m, N—CH$_3$+CO—CH$_2$CH—CO+CH$_2$—C$_6$H$_4$), 7.70 (4H, s, aromatic-H).

EXAMPLE 2

N-[4-(N-Hydroxyamino)-2(RS)-isobutylsuccinyl]-L-4'-sulfophenylalanine-N-methylamide, Monosodium Salt (a) N-Benzyloxycarbonyl-L-4'-sulfophenylalanine, Monosodium Salt L-4'-sulfophenylalanine [HELVETICA CHIMICA ACTA, 66, P. 1355 (1983), 18.0 g, 73.4 mmol] and NaHCO$_3$ (24.7 g, 294 mmol) were dissolved in water (180 ml). The solution was added with benzyloxycarbonyl chloride (14.0 ml, 88.1 mmol) and Et$_2$O (20 ml) under ice-cooling and stirring and stirred at room temperature for 5 hours. The reaction liquid was washed two times with AcOEt (200 ml), made pH 1–2 with 6N-HCl and extracted three times with THF (200 ml) under the saturation of NaCl. The organic layer was washed with a saturated aqueous NaCl solution (200 ml), dried over anhydrous MgSO$_4$ and evaporated under reduced pressure to give the title compound (29.5 g, in quantitative yield) as white crystals by evaporating the solvent under reduced pressure.

m.p.; 260° C. (dec.). Specific rotation[$\alpha$]$_D$=−0.81° (c=1.0, MeOH). Rf value; 0.48 (CHCl$_3$:MeOH:AcOH=5:2:1), 0.50 (n-BuOH:AcOH:water=4:1:1).

$^1$H-NMR(MeOH-d$_4$) $\delta$ ppm; 2.8–3.3 (2H, m, C$_6$H$_4$—CH$_2$), 4.3–4.55 (1H, m, NH—CH—CO), 5.03 (2H, s, PhCH$_2$), 7.15–7.9 (10H, NH+aromatic-H).

(b) L-4'-Sulfophenylalanine-N-methylamide, Monosodium Salt

The compound (29.5 g, 73.5 mmol) of Example 2-a and HOBT (10.4 g, 77.2 mmol) were dissolved in DMF (240 ml) and stirred at −15° C. The solution was dropped with an aqueous solution of methylamine hydrochloride (60 ml, 5.96 g, 88.3 mmol), followed by the addition of EDC (16.2 g, 84.5 mmol) and TEA (12.2 ml, 88.4 mmol) and stirred at 5° overnight. The reaction liquid was concentrated under reduced pressure and then purified by column chromatography (silica gel; 1.5 Kg, elution with the mixed solvent; CHCl$_3$:MeOH=9:1–4:1).

The obtained pale yellow oily product (36.5 g) was dissolved in MeOH (300 ml) and hydrogenated by catalyst at room temperature for 7 hours in the presence of 10% Pd-C (50% wet, 2.3 g). After the catalyst was filtered off, the filtrate was evaporated under reduced pressure to remove MeOH and crystallized from MeOH-AcOEt, giving the title compound (16.2 g, 81%) as white crystals.

m.p.; ≧300° C. Specific rotation[$\alpha$]$_D$=+43.3° (c=1.0, H$_2$O). Rf value; 0.19 (n-BuOH:AcOH:water=4:1:1).

$^1$H-NMR(DMSO-d$_6$) $\delta$ ppm; 2.60 (NHCH$_3$), 2.7–3.0 (2H, m, C$_6$H$_4$CH$_2$), 3.4–3.7 (1H, m, H$_2$N—CH—CO), 3.9 (2H, brm, H$_2$N), 7.35 (4H, AA'BB', aromatic-H), 7.9–8.2 (1H, m, CO—NH).

(c) N-[4-tert-Butoxy-2(RS)-isobutylsuccinyl]-L-4'-sulfophenylalanine-N-methylamide, Monosodium Salt The compound (8.32 g, 29.7 mmol) of Example 2-b, the compound (5.70 g, 24.8 mmol) of Example 1-b, and HOBT (3.51 g, 26.0 mmol) were dissolved in DMF (140 ml). The solution was added with EDC (5.69 g, 29.7 mmol) at −15° C. under stirring and stirred at room temperature overnight. The reaction mixture was concentrated under reduced pressure, followed by dissolving the concentrate in THF (200 ml). The solution was washed with 1N-HCl, a saturated aqueous solution of NaHCO$_3$ and then the saturated aqueous solution of NaCl two times respectively. The organic layer was dried over anhydrous MgSO$_4$, evaporated under reduced pressure to remove the solvent and purified by column chromatography (silica gel; 500 g, elution with the mixed solvent; CHCl$_3$:MeOH=9:1–4:1) to give the title compound (6.10 g, 50%) of a colorless oil.

m.p.; ≧300° C. Specific rotation[α]$_D$=−11.1° (c=1.0, MeOH). Rf value; 0.56 (CHCl$_3$:MeOH:AcOH=5:2:1).

$^1$H-NMR(MeOH-d$_4$) δ ppm; 0.6–0.95 (6H, m, CH(CH$_3$)$_2$), 0.9–1.8 (12H, m, C(CH$_3$)$_3$+CH$_2$CH(CH$_3$)$_2$), 2.1–3.2 (7H, m, C$_6$H$_4$CH$_2$+(CH$_3$)$_3$CO$_2$C—CH$_2$+NHCH$_3$), 3.4–3.7 (1H, m, CO—CHCH$_2$), 4.3 (2H, brm, 2×NH), 4.4–4.7 (1H, m, NH—CH—CO), 7.54 (4H, AA'BB', aromatic-H).

(d) N-[4-(N-Benzyloxyamino)-2(RS)-isobutylsuccinyl]-L-4'-sulfophenylalanine-N-methylamide, Monosodium Salt The compound (0.29 g, 0.59 mmol) of Example 1-c was added to ice-cooled 95% aqueous trifluoroacetic acid (3 ml) and stirred at 5° C. for 4 hours. The reaction mixture was concentrated under reduced pressure. The obtained colorless oil (0.25 g, 100%), O-benzylhydroxylamine hydrochloride (0.11 g, 0.71 mmol), HOBT (0.08 g, 0.62 mmol) and TEA (0.10 ml, 0.71 mmol) were dissolved in DMF (5 ml), added with EDC (0.13 g, 0.68 mmol) at −15° C. under stirring and stirred at room temperature overnight. The mixture was evaporated under reduced pressure to remove the solvent and purified by column chromatography (silica gel; 15 g, elution with the mixed solvent; CHCl$_3$:MeOH=9:1–4:1) to give the title compound (0.14 g, 43%) of a white solid.

m.p.; 111° C. Specific rotation[α]$_D$=−16.4° (c=1.0, MeOH). Rf value; 0.62 (CHCl$_3$:MeOH:AcOH=5:2:1), 0.59 (n-BuOH:AcOH:water=4:1:1).

$^1$H-NMR(MeOH-d$_4$) δ ppm; 0.5–1.6 (9H, m, CH$_2$CH(CH$_3$)$_2$), 1.8–3.7 (8H, m, C$_6$H$_4$CH$_2$+CO—CH$_2$CH—CO+NHCH$_3$), 4.58 (1H, m, NH—CH—CO), 7.1–7.9 (9H, AA'BB', aromatic-H).

(e) N-[4-(N-Hydroxyamino)-2(RS)-isobutylsuccinyl]-L-4'-sulfophenylalanine-N-methylamide, Monosodium Salt The compound (0.12 g, 0.22 mmol) of Example 1-d was dissolved in MeOH (5 ml), added with 10% Pd-C (50% wet, 0.12 g), and then stirred vigorously in a stream of hydrogen at room temperature for 5 hours. After the catalyst was filtered off, MeOH of the filtrate was removed under reduced pressure. The residue was purified by column chromatography (silica gel; 10 g, elution with the mixed solvent; CHCl$_3$:MeOH=4:1–2:1) to give the title compound (0.06 g, 60%) of pale yellow crystals.

m.p.; 200–202° C., Specific rotation[α]$_D$=−12.2° (c=1.0, MeOH), Rf value; 0.33 (CHCl$_3$:MeOH:AcOH=5:2:1), 0.39 (n-BuOH:AcOH:water=4:1:1). A analytical value calculated for C$_{18}$H$_{26}$N$_3$O$_7$SNa. Theoretical value:C, 47.89; H, 5.8; N, 9.31. Found:C, 47.66; H, 5.97; N, 9.15.

$^1$H-NMR(MeOH-d$_4$) δ ppm; 0.6–1.0 (6H, m, CH(CH$_3$)$_2$), 1.0–1.7 (3H, m, CH$_2$CH(CH$_3$)$_2$), 1.9–3.6 (8H, m, C$_6$H$_4$CH$_2$+CO—CH$_2$CH—CO+NHCH$_3$), 4.4–5.0 (1H, m, NH—CH—CO), 4.85 (3H, brm, 3×NH), 7.53 (4H, AA'BB', aromatic-H).

EXAMPLE 3

N-[4-(N-Hydroxyamino)-2(R)-isobutyl-3(R or S)-(3-phenyltrimethylene) succinyl]-O-sulfo-L-tyrosine-N-methylamide, Monosodium Salt (a) Benzyl 2(R)-bromo-4-metylpentanoate 2(R)-Bromo-4-metylpentanoic acid (28.5 g, 146 mmol), benzyl alcohol (18.1 ml, 175 mmol) and 4-dimethylaminopyridine (1.90 g, 14.6 mmol) were dissolved in CH$_2$Cl$_2$ (140 ml), and added with EDC (35.6 g, 175 mmol) under ice-cooling and stirring The mixture was stirred under ice-cooling for 1 hour and further at room temperature overnight and washed for separation with water, a saturated aqueous solution of NaHCO$_3$ and then a saturated aqueous solution of NaCl two times respectively. The organic layer was dried over an hydrous MgSO$_4$, evaporated under reduced pressure and purified by column chromatography (silica gel; 700 g, elution with the mixed solvent; n-hexane:AcOEt=40:1), giving the title compound (32.0 g, 77%) of a colorless oil.

Specific rotation[α]$_D$=+31.8° (c=1.0, MeOH), Rf value; 0.48 (AcOEt:n-hexane=1:5).

$^1$H-NMR(CDCl$_3$) δ ppm; 0.9 (6H, 2×d, J=6.5 Hz, CH(CH$_3$)$_2$), 1.67 (1H, m, (CH$_3$)$_2$CH) 1.90 (2H, m, (CH$_3$)$_2$CH—CH$_2$), 4.30 (1H, t, J=7 Hz, —CH—Br), 5.2 (2H, s, CH$_2$—Ph), 7.32 (5H, s, aromatic-H).

(b) Dibenzyl 3(RS)-tert-butoxycarbonyl-2(R)-isobutylsuccinate

Benzyl tert-butyl malonate (24.9 g, 99.6 mmol) was dissolved in DMF (60 ml) and added portion wise with potassium tert-butoxide (13.4 g, 120 mmol) at 0° C. under stirring. The mixture was stirred at room temperature for 1 hour, then cooled to 0° C., and dropped in 1 hour with the solution of the Example 3-a compound (28.4 g, 99.6 mmol) dissolved in DMF (60 ml). After the reaction mixture was stirred at 5° C. overnight, it was added with AcOEt (2 l) and washed with a saturated aqueous solution of NaCl, 1N-HCl, a saturated aqueous solution of NaHCO$_3$ and then the saturated aqueous solution of NaCl two times respectively. The organic layer was dried over anhydrous MgSO$_4$, evaporated under reduced pressure and purified by column chromatography (silica gel; 750 g, elution with the mixed solvent; n-hexane:AcOEt=20:1), giving the title compound (40.0 g, 89%) of a colorless oil.

Specific rotation[α]$_D$=+16.7° (c=1.0, MeOH), Rf value; 0.56 (AcOEt:n-hexane=1:5).

$^1$H-NMR(CDCl$_3$) δ ppm; 0.82 (6H, 2×xd, J=10 Hz, CH(CH$_3$)$_2$), 1.15–1.8 (12H, 2×s+m, (CH$_3$)$_2$CH—CH$_2$+C(CH$_3$)$_3$), 3.2 (1H, m, CH$_2$—CH—CO), 3.7 (1H, m, CO—CH—CO), 5.1 (4H, m, CH$_2$—Ph×2), 7.32 (10H, s, aromatic-H).

(c) Dibenzyl 3(RS)-tert-butoxycarbonyl-3-cinnamyl-2(R)-isobutylsuccinate

The compound (9.49 g, 20.9 mmol) of Example 3-b was dissolved in DMF (100 ml), and added portion wise with 60% NaH (1.0 g, 25.1 mmol) at room temperature under stirring. The mixture was stirred at room temperature for 2 hours, cooled to 0° C., added portion wise with cinnamyl bromide (5.35 g, 27.2 mmol) and stirred at 5° C. for 15 hours. After removing the solvent under reduced pressure, the residue was added with AcOEt (500 ml), and washed with a saturated aqueous solution of NaCl, 1N-HCl, a saturated aqueous solution of NaHCO$_3$ and then the saturated aqueous solution of NaCl two times respectively. The organic layer was dried over anhydrous MgSO$_4$, evaporated under reduced pressure and purified by column chromatography (silica gel; 700 g, elution with the mixed solvent; n-hexane:AcOEt=20:1), giving the title compound (10.9 g, 91%) of a colorless oil.

Rf value; 0.34 (AcOEt:n-hexane=1:9).

$^1$H-NMR(CDCl$_3$) δ ppm; 0.7–1.0 (6H, m, CH(CH$_3$)$_2$), 1.1–2.1 (12H, m, (CH$_3$)$_2$CH—CH$_2$,+C(CH$_3$)$_3$), 2.8 (2H, bd, J=5.4 Hz, CH$_2$—CH═CH), 3.0–3.3 (1H, m, CH$_2$—CH—CO), 5.0–5.2 (4H, m, CH$_2$—O×2), 6.1–6.4 (2H, m, CH$_2$—CH═CH), 7.1–7.5 (15H, m, aromatic-H).

(d) 3(RS)-tert-butoxycarbonyl-6-phenyl-2(R)-isobutylhexanoic Acid

The compound (4.2 g, 7.36 mmol) of Example 3-c was dissolved in ethanol (35 ml), added with 10% Pd-C (50% wet, 1.3 g), and then stirred vigorously in a stream of hydrogen at room temperature for 7 hours. After the catalyst was filtered off, ethanol of the filtrate was removed under reduced pressure. The residue was added with N-methylmorpholine (0.81 ml, 7.36 mmol) and toluene (50 ml), and refluxed for 2 hours. The reaction liquid was washed with 1N-HCl and then a saturated aqueous solution of NaCl two times respectively, dried over anhydrous $MgSO_4$, evaporated under reduced pressure and purified by column chromatography (silica gel; 150 g, elution with the mixed solvent; $CHCl_3$:MeOH=200:1), giving the title compound (1.1 g, 43%) of a colorless oil.

Rf value; 0.60 ($CHCl_3$:MeOH:AcOH=95:5:3).

$^1$H-NMR($CDCl_3$) δ ppm; 0.88 (6H, bd, J=5.7 Hz, $CH(CH_3)_2$), 1.0–2.0 (16H, m, $(CH_3)_2CH$—$CH_2$, +C$(CH)_3)_3$+$CH_2$—$CH_2$—$CH_2$—Ph), 2.4–2.8 (4H, m, $\underline{CH}$—COx2+$CH_2$—Ph), 7.0–7.4 (5H, m, aromatic-H).

(e) N-[4-tert-Butoxy-2(R)-isobutyl-3(R or S)-(3-phenyltrimethylene)succinyl]-L-tyrosine-N-methylamide The compound (4.0 g, 11.5 mmol) of Example 3-d, L-tyrosine-N-methylamide hydrochloride (4.0 g, 17.3 mmol) and HOBT (1.60 g, 11.8 mmol) were dissolved in DMF (25 ml) and $CH_2Cl_2$ (25 ml) and added with TEA (2.50 ml, 17.9 mmol) and EDC (2.65 g, 13.8 mmol) at −15° C. under stirring. The mixture was stirred at −15° C. for 1 hour and further at room temperature overnight and then evaporated under reduced pressure. The residue was added with AcOEt (100 ml), washed with a saturated aqueous solution of NaCl, 1N-HCl, a saturated aqueous solution of $NaHCO_3$ and then the saturated aqueous solution of NaCl two times respectively, dried over anhydrous $MgSO_4$, evaporated under reduced pressure and purified by column chromatography (silica gel; 150 g, elution with the mixed solvent; n-hexane:AcOEt=10:9), giving two isomers of the title compounds as pale yellow oils.

Isomer A

The pale yellow oil (30%), Specific rotation$[α]_D$=−8.2° (c=0.5, MeOH), Rf value; 0.30 (AcOEt:n-hexane=1:1).

$^1$H-NMR($CDCl_3$) δ ppm; 0.80 (6H, m, $CH(CH_3)_2$), 0.9–1.9 (16H, s+m, $(CH_3)_2CH$—$CH_2$, +$\underline{C(CH_3)_3}$+$CH_2$—$CH_2$—$CH_2$—Ph), 2.2–3.1 (9H, m, N—$CH_3$+—$\underline{CH}$—COx2+$CH_2$—Ph+$C_6H_4\underline{CH_2}$), 4.54 (1H, m, NH—$\underline{CH}$—CO), 6.0 (1H, m, $\underline{NH}$), 6.4–7.4 (9H, m, aromatic-H).

Isomer B

The pale yellow oil (38%), specific rotation$[α]_D$=+9.0° (c=0.5, MeOH), Rf value; 0.29 (AcOEt:n-hexane=1:1).

$^1$H-NMR($CDCl_3$) δ ppm; 0.75 (6H, d, J=4.6 Hz, CH$(CH_3)_2$) 0.8–1.7 (16H, s+m, $(CH_3)_2CH$—$CH_2$+$C(CH_3)_3$+$\underline{CH_2}$—$CH_2$—$CH_2$—Ph), 2.1–3.1 (9H, d+m, J=4.6 Hz, N—$CH_3$+—$\underline{CH}$—COx2+$CH_2$—Ph+$C_6H_4\underline{CH_2}$), 4.65 (1H, m, $\overline{NH}$—$\underline{CH}$—CO), 6.3–7.4 (11H, m, $\underline{NH}$x2+aromatic-H).

The following compounds were synthesized in the same methods as used in d–g of Example 1.

(f) N-[4-Hydroxy-2(R)-isobutyl-3(R or S)-(3-phenyltrimethylene)succinyl]-L-tyrosine-N-methylamide Isomer B White solid (89%), m.p.; 222° C., specific rotation$[α]_D$=−7.2° (c=0.5, MeOH), Rf value; 0.38 ($CHCl_3$:MeOH=95:5:3).

$^1$H-NMR (MeOH-$d_4$) δ ppm; 0.78 (6H, m, $CH(CH_3)_2$), 0.9–1.6 (7H, m, $(CH_3)_2CH$—$CH_2$+$CH_2$—$CH_2$—$\underline{CH_2}$—Ph), 2.1–3.0 (9H, m, N—$CH_3$+—$\underline{CH}$—COx2+$CH_2$—Ph+$C_6H_4$ $\underline{CH_2}$), 4.60 (1H, m, $\overline{NH}$—$\underline{CH}$—CO), 6.3–7.4 (9H, m, aromatic-H).

Isomer A

White solid (85%), m.p.; 173–177° C., specific rotation $[α]_D$=+8.1° (c=1.0, MeOH), Rf value; 0.39 ($CHCl_3$:MeOH:AcOH=95:5:3).

$^1$H-NMR (MeOH-$d_4$) δ ppm; 0.85 (6H, m, $CH(CH_3)_2$), 0.9–1.8 (7H, m, $(CH_3)_2CH$—$CH_2$+$CH_2$—$CH_2$—$\underline{CH_2}$—Ph), 2.2–3.2 (9H, m, N—$CH_3$+—$\underline{CH}$—COx2+$CH_2$—Ph+$C_6H_4$ $\underline{CH_2}$), 4.50 (1H, m, $\overline{NH}$—$\underline{CH}$—CO), 6.4–7.5 (9H, m, aromatic-H).

(g) N-[4-(N-Benzyloxyamino)-2(R)-isobutyl-3(R or S)-(3-phenyltrimethylene)succinyl]-L-tyrosine-N-methylamide Isomer B (yield 60%)

m.p.; 220° C., specific rotation$[α]_D$=+5.60° (c=1.0, DMF), Rf value; 0.51 ($CHCl_3$:MeOH:AcOH=95:5:3).

$^1$H-NMR(MeOH-$d_4$) δ ppm; 0.8 (6H, m, $CH(CH_3)_2$), 0.9–1.6 (7H, m, $(CH_3)_2CH$—$CH_2$+$CH_2$—$CH_2$—$\underline{CH_2}$—Ph), 2.0–3.0 (9H, m, N—$CH_3$+—$\underline{CH}$—COx2+$CH_2$—Ph+$C_6H_4$ $\underline{CH_2}$), 4.60 (1H, m, $\overline{NH}$—$\underline{CH}$—CO), 6.3–7.5 (14H, m, aromatic-H).

Isomer A (yield 50%)

m.p.; 185–190° C., specific rotation$[α]_D$=+8.2° (c=0.5, MeOH), Rf value; 0.51 ($CHCl_3$:MeOH:AcOH=95:5:3).

$^1$H-NMR(MeOH-$d_4$) δ ppm; 0.8–1.8 (13H, m, $(CH_3)_2CH$—$CH_2$+$CH_2$—$CH_2$—$CH_2$—Ph), 2.2–3.2 (9H, m, N—$CH_3$+—$\underline{CH}$—COx2+$CH_2$—Ph+$C_6H_4\underline{CH_2}$), 4.5 (1H, m, NH—$\underline{CH}$—CO), 6.5–7.5 (14H, m, aromatic-H).

(h) N-[4-(N-Benzyloxyamino)-2(R)-isobutyl-3(R or S)-(3-phenyltrimethylene)succinyl]-O-sulfo-L-tyrosine-N-methylamide, Monosodium Salt Isomer B White amorphous powder (92%), specific rotation$[α]_D$=+10.0° (c=0.9, MeOH), Rf value; 0.86 ($CHCl_3$:MeOH:AcOH=5:2:1), 0.82 (n-BuOH:AcOH:water=4:1:1).

$^1$H-NMR(MeOH-$d_4$) δ ppm; 0.5–1.7 (13H, m, J=4.6 Hz, $(CH_3)_2CH$—$CH_2$+$CH_2$—$CH_2$—$CH_2$—Ph), 1.9–3.0 (9H, m, N—$CH_3$+—$\underline{CH}$—COx2+$CH_2$—Ph+$C_6H_4\underline{CH_2}$), 4.50 (1H, m, NH—$\underline{CH}$—CO), 7.1–7.5 (14H, m, aromatic-H).

Isomer A

White amorphous powder (95%), specific rotation$[α]_D$=+13.5° (c=1.0, MeOH), Rf value; 0.86 ($CHCl_3$:MeOH:AcOH=5:2:1), 0.82 (n-BuOH:AcOH:water=4:1:1).

$^1$H-NMR(MeOH-$d_4$) δ ppm; 0.6–1.8 (13H, m, $(CH_3)_2CH$—$CH_2$+$CH_2$—$CH_2$—$CH_2$—Ph), 2.0–3.0 (9H, m, N—$CH_3$+—$\underline{CH}$—COx2+$\underline{CH}$—Ph+$C_6H_4\underline{CH_2}$), 4.47 (1H, m, NH—$\underline{CH}$—CO), 7.0–7.5 (14H, m, aromatic-H).

(i) N-[4-(N-Hydroxyamino)-2(R)-isobutyl-3(R or S)-(3-phenyltrimethylene)succinyl]-O-sulfo-L-tyrosine-N-methylamide, Monosodium Salt Isomer B White amorphous powder (98%), specific rotation$[α]_D$=−41.0° (c=1.0, MeOH), Rf value; 0.69 ($CHCl_3$:MeOH:AcOH=5:2:1), 0.76 (n-BuOH:AcOH:water=4:1:1). Analytical value calculated for $C_{27}H_{36}N_3O_8SNa$. Theoretical value:C, 55.37; H, 6.20; N, 7.17. Found:C, 55.37; H, 6.39; N, 7.24.

$^1$H-NMR(MeOH-$d_4$) δ ppm; 0.6–1.7 (13H, m, $(CH_3)_2CH$—$CH_2$+$CH_2$—$CH_2$—$CH_2$—PH), 1.8–3.1 (9H, m, N—$CH_3$+—$\underline{CH}$—COx2+$CH_2$—Ph+$C_6H_4\underline{CH_2}$), 4.50 (1H, m, NH—$\underline{CH}$—CO), 7.22 (9H, m, aromatic-H).

Isomer A

White amorphous powder (100%), specific rotation$[α]_D$=−11.9° (c=1.0, MeOH), Rf value; 0.69 ($CHCl_3$:MeOH:AcOH=5:2:1), 0.77 (n-BuOH:AcOH:water=4:1:1). Analytical value calculated for $C_{27}H_{36}N_3O_8SNa$. Theoretical value:C, 55.37; H, 6.20; N, 7.17. Found:C, 55.45; H, 6.29; N, 7.36.

¹H-NMR(MeOH-d₄) δ ppm; 0.6–1.8 (13H, m, (CH₃)₂CH—CH₂+CH₂—CH₂—CH₂—Ph), 2.0–3.4 (9H, m, N—CH₃+—CH—CO×2+CH₂—Ph+C₆H₄CH₂), 4.60 (1H, m, NH—CH—CO), 7.2 (9H, m, aromatic-H).

EXAMPLE 4

N-[4-(N-Hydroxyamino)-2(R)-isobutyl-3(RS)-(3-phenyltrimethylene)succinyl]-L-4'-sulfophenylalanine-N-methylamide, Monosodium Salt (a) N-[4-tert-Butoxy-2(R)-isobutyl-3(RS)-(3-phenyltrimethylene)succinyl]-L-4'-sulfophenylalanine-N-methylamide, Monosodium Salt By the same method as that of Example 2-c, the title compound (3.69 g, 60%) of a white solid was obtained from the compound (3.49 g, 10.0 mmol) of Example 3-d and the compound (3.64 g, 13.0 mmol) of Example 2-b.

m.p.; 235–240° C., specific rotation[α]$_D$=−6.97° (c=1.0, MeOH), Rf value; 0.66 (CHCl₃:MeOH:AcOH=5:2:1), 0.71 (n-BuOH:AcOH:water=4:1:1).

¹H-NMR(MeOH-d₄) δ ppm; 0.55–1.06 (6H, m, CH—(CH₃)₂), 1.1–1.8 (16H, m, C(CH₃)₃+CH₂CH(CH₃)₂+PhCH₂(CH₂)₂), 2.2–2.8 (7H, m, PhCH₂+NHCH₃+CO—CH×2), 2.81–3.2 (2H, m, C₆H₄—CH₂), 4.58 (1H, m, NH—CH—CO), 6.8–7.9 (9H, m, aromatic-H).

(b) N-[4-Hydroxy-2(R)-isobutyl-3(RS)-(3-phenyltrimethylene)succinyl]-L-4'-sulfophenylalanine-N-methylamide, Monosodium Salt To the compound (3.84 g, 6.29 mmol) of Example 4-a was added ice-cooled 95% aqueous trifluoroacetic acid (45 ml). The reaction mixture was stirred at 50° C. overnight and concentrated under reduced pressure. The residue was added with Et₂O and stirred at room temperature for 1 hour. The precipitating solid was filtered and dried in a desiccator under reduced pressure.

m.p.; 243–256° C., specific rotation[α]$_D$=−4.95° (c=1.0, MeOH), Rf value; 0.53 (CHCl₃:MeOH:AcOH=5:2:1), 0.67 (n-BuOH:AcOH:water=4:1:1).

¹H-NMR(MeOH-d₄) δ ppm; 0.5–1.0 (6H, m, CH—(CH₃)₂), 1.2–1.8 (7H, m, CH₂CH(CH₃)₂+PhCH₂(CH₂)₂), 2.2–2.7 (7H, m, PhCH₂+NHCH₃+CO—CH×2), 2.8–3.2 (2H, m, C₆H₄—CH₂) 4.56 (1H, brm, NH—CH—CO), 6.8–7.9 (9H, m, aromatic-H).

(c) N-[4-(N-Hydroxyamino)-2(R)-isobutyl-3(RS)-(3-phenyltrimethylene)succinyl]-L-4'-sulfophenylalanine-N-methylamide, Monosodium Salt The compound (3.53 g, 6.37 mmol) of Example 4-b and HOBT (1.29 g, 9.56 mmol) were dissolved in DMF (180 ml), added with EDC (1.83 g, 9.56 mmol) at an ice-cooling temperature under stirring and stirred at an ice-cooling temperature for 1 hour. The mixture was added with hydroxylamine hydrochloride (664 mg, 9.56 mmol) and dropped with triethylamine (1.33 ml, 9.56 mmol), stirred under ice-cooling for 3 hours and evaporated under reduced pressure. The residue was purified by a reverse-phase column chromatography (Fuji Silysia Chemical Ltd., Chromatorex ODS DM-1020T; 250 g, elution with a MeOH-water solution containing 5–20% MeOH) to give the title compound (1.57 g, 43%) of white amorphous powder upon freeze-drying.

Specific rotation[α]$_D$=−3.73° (c=1.0, MeOH), Rf value; 0.42 (CHCl₃:MeOH:AcOH=5:2:1), 0.66 (n-BuOH:AcOH:water 4:1:1), Analytical value calculated for C₂₇H₃₆N₃O₇SNa. Theoretical value:C, 56.93; H, 6.37; N, 7.38. Found:C, 56.69; H, 6.58; N, 7.1.

¹H-NMR(MeOH-d₄) δ ppm; 0.8–0.95 (6H, m, CH—(CH₃)₂), 0.96–1.82 (7H, m, CH₂CH(CH₃)₂+PhCH₂(CH₂)₂), 1.82–2.74 (7H, m, PhCH₂+NHCH₃+2×CO—CH), 2.75–3.5 (2H, m, C₆H₄—CH₂), 4.56 (1H, brm, NH—CH—CO), 6.95–7.40 (9H, m, aromatic-H).

EXAMPLE 5

N-[4-(N-Hydroxyamino)-2(R)-isobutyl-3(R or S)-(thienylthiomethylene)succinyl]-L-4'-sulfophenylalanine-N-methylamide, Monosodium Salt (a) N-[4-Benzyloxy-3-benzyloxycarbonyl-2(R)-isobutyl-succinyl]-L-4'-sulfophenylalanine-N-methylamide, Monosodium Salt By the same method as that of Example 2-c, the title compound (12.6 g, 65%) of white crystals was obtained from the compound (8.18 g, 29.2 mmol) of Example 2-b and 2(R)-isobutyl-3,3-dibenzyloxycarbonyl-n-propionic acid (11.6 g, 29.2 mmol).

m.p.; 237–245° C., specific rotation[α]$_D$=−14.0° (c=1.0, MeOH), Rf value; 0.79 (CHCl₃:MeOH:AcOH=5:2:1), 0.60 (n-BuOH:AcOH:water=4:1:1).

¹H-NMR(MeOH-d₄) δ ppm; 0.6–0.9 (6H, m, CH(CH₃)₂), 0.95–1.7 (3H, m, CH₂CH(CH₃)₂), 2.5–3.8 (m, C₆H₄CH₂+NHCH₃+CO—CHCH—CO), 4.3–4.8 (1H, m, NH—CH—CO), 5.0–5.2 (4H, m, PhCH₂×2), 7.2–7.9 (14H, m, aromatic-H).

(b) N-[4-Hydroxy-3-hydroxycarbonyl-2(R)-isobutylsuccinyl]-L-4'-sulfophenylalanine-N-methylamide, Monosodium Salt The compound (12.6 g, 19.1 mmol) of Example 5-a was dissolved in MeOH (250 ml), added with 10% Pd-C (50% wet, 12.6 g), and then stirred vigorously in a stream of hydrogen at room temperature for 5 hours. After the catalyst was filtered off, MeOH of the filtrate was removed under reduced pressure. The concentrate was lyophilized, whereby the title compound (8.92 g, 97%) of white amorphous powder was obtained.

Specific rotation[α]$_D$=+21.0° (c=1.0, MeOH), Rf value; 0.16 (CHCl₃:MeOH:AcOH=5:2:1), 0.29 (n-BuOH:AcOH:water=4:1:1).

¹H-NMR(MeOH-d₄) δ ppm; 0.75–0.95 (6H, m, CH(CH₃)₂), 0.95–1.7 (3H, m, CH₂CH(CH₃)₂), 2.8–3.2 (6H, m, C₆H₄CH₂+NHCH₃+(HO₂C)₂CH—CH), 3.55 (1H, d, (HO₂C)₂CH), 4.53 (1H, m, NH—CH—CO), 4.97 (2H, brm, 2×NH), 7.2–8.9 (4H, AA'BB', aromatic-H).

(c) N-[4-Hydroxy-2(R)-isobutyl-3-ethenylsuccinyl]-L-4'-sulfophenylalanine-N-methylamide, Monosodium Salt The compound (8.72 g, 18.2 mmol) of Example 5-b and piperidine (3.40 g, 39.9 mmol) were dissolved in ethanol (90 ml), stirred at room temperature for 30 min. and added with 36% formalin solution (14.9 ml, 181 mmol). The reaction mixture was stirred at room temperature for 1 hour and further at 80° C. for 1 hour and concentrated under reduced pressure. The residue was dissolved in 1N-HCl (200 ml) and extracted two times with THF (200 ml). The THF solution was washed with a saturated aqueous solution of NaCl, dried over anhydrous MgSO₄ and evaporated under reduced pressure to give the title compound (7.90 g, 97%) of a pale yellow solid.

¹H-NMR(MeOH-d₄+CDCl₃) δ ppm; 0.75–1.0 (6H, m, CH(CH₃)₂), 1.1–2.0 (3H, m, CH₂CH(CH₃)₂), 2.70 (3H, s, NHCH₃), 2.9–3.2 (2H, m, C₆H₄CH₂), 3.4–3.8 (1H, m, HO₂C—C—CH), 4.45–4.7 (1H, m, NH—CH—CO), 5.12 (2H, brm, 2×NH), 5.63, 6.25 (2×1H, 2×s, C=CH₂), 7.15–7.85 (4H, AA'BB', aromatic-H).

(d) N-[4-(N-Benzyloxyamino)-2(R)-isobutyl-3-ethenylsuccinyl]-L-4'-sulfophenylalanine-N-methylamide, Monosodium Salt The compound (7.90 g, 17.6 mmol) of Example 5-c, O-benzylhydroxylamine hydrochloride (11.3 g, 70.5 mmol) and HOBT (5.24 g, 38.8 mmol) were suspended in DMF (320 ml). The suspension was added with TEA (7.13 ml, 70.5 mmol) and EDC (10.1 g, 52.8 mmol) at −15° C. under stirring and stirred at room temperature overnight. The reaction mixture was concentrated under reduced pressure and purified by a reverse-phase column chromatography (Fuji Silysia Chemical Ltd., Chromatorex ODS-1020T; 200 g, elution with 30–36% MeOH water) to give the title compound (4.10 g, 42%) of white amorphous powder upon freeze-drying.

m.p.; 102–106° C., specific rotation$[\alpha]_D$=−13.8° (c=1.0, MeOH), Rf value; 0.71 ($CHCl_3$:MeOH:AcOH=5:2:1), 0.60 (n-BuOH:AcOH:water=4:1:1).

$^1$H-NMR(MeOH-$d_4$) δ ppm; 0.75–0.95 (6H, m, CH($CH_3$)$_2$), 1.0–2.0 (3H, m, $CH_2CH(CH_3)_2$), 2.6–3.2 (6H, m, $NHCH_3$+$C_6H_4CH_2$+CO—$\overline{C}$—$\underline{CH}$), 4.5–4.75 (1H, m, NH—$\underline{CH}$—CO), 4.85 (3H, brm, 3×$\underline{NH}$), 4.90 (2H, s, Ph$\underline{CH_2}$), 5.23, 5.48 (2×1H, 2×s, C=$\underline{CH_2}$), 7.1–7.8 (4H, AA'BB', aromatic-H).

(e) N-[4-(N-Benzyloxyamino)-2(R)-isobutyl-3(RS)-(thienylthiomethylene)succinyl]-L-4'-sulfophenylalanine-N-methylamide, Monosodium Salt The compound (4.10 g, 7.41 mmol) of Example 5-d was dissolved in thiophenethiol (23.7 g, 204 mmol), and stirred in a dark and nitrogen atmosphere at 60° C. overnight. The reaction mixture was added with $Et_2O$. The resulting crystals were filtered and washed with $Et_2O$ to give the title compound (4.23 g, 86%) of yellow crystals upon drying.

m.p.; 221–226° C. (dec.), specific rotation$[\alpha]_D$=−35.0° (c=1.0, MeOH), Rf value; 0.71 ($CHCl_3$:MeOH:AcOH= 5:2:1), 0.69 (n-BuOH:AcOH:water=4:1:1).

$^1$H-NMR(MeOH-$d_4$+$CDCl_3$) δ ppm; 0.5–1.7 (9H, m, ($CH_3$)$_2$CH—$CH_2$), 1.8–3.6 (9H, m, N—$CH_3$+S—$CH_2CHCH$—CO+$C_6H_4CH_2$), 4.4–4.7 (3H, m, Ph$CH_2$+N—$\underline{CH}$—$\overline{CO}$), 6.85–7.9 (12H, m, aromatic-H).

(f) N-[4-(N-Hydroxyamino)-2(R)-isobutyl-3(R or S)-(thienylthiomethylene)succinyl]-L-4'-sulfophenylalanine-N-methylamide, Monosodium Salt The compound (4.23 g, 6.34 mmol) of Example 5-e was added with anisole (5 ml) and hydrofluoric acid (50 ml) and stirred at 0° C. for 30 min. The hydrofluoric acid was evaporated under reduced pressure. The residue was added with $Et_2O$. The resulting crystals were purified by a reverse-phase column chromatography (Fuji Silysia Chemical Ltd., Chromatorex ODS-1020T; 200 g, elution with a MeOH-water solution containing 9–13% MeOH) to give the title compound (1.33 g, 36.4%) of two kinds as white amorphous powder upon freeze-drying.

Isomer A (1.33 g, 36%)

m.p.; 142–148° C., specific rotation$[\alpha]_D$=−44.9° (c=1.0, MeOH), Rf value; 0.44 ($CHCl_3$:MeOH:AcOH=5:2:1), 0.51 (n-BuOH:AcOH:water=4:1:1). Analytical value calculated for $C_{23}H_{30}N_3O_7S_3Na$. Theoretical value:C, 47.66; H, 5.22; N, 7.25. Found:C, 47.4; H, 5.44; N, 7.03.

$^1$H-NMR(MeOH-$d_4$) δ ppm; 0.7–0.95 (6H, m, ($CH_3$)$_2$CH—$CH_2$), 1.0–1.7 (3H, m, $CH_2$—CH($CH_3$)$_2$), 1.8–3.6 (9H, m, N—$CH_3$+S—$CH_2CHCH$—$\overline{CO}$+$C_6H_4CH_2$), 4.4–4.7 (1H, m, NH—$\underline{CH}$—CO), 4.85 (3H, brm, 3×$\underline{NH}$), 6.9–7.9 (7H, m, aromatic-H).

Isomer B (0.40 g, 11%)

m.p.; 132–137° C., specific rotation$[\alpha]_D$=+43.2° (c=1.0, MeOH), Rf value; 0.57 ($CHCl_3$:MeOH:AcOH=5:2:1), 0.56 (n-BuOH:AcOH:water=4:1:1). Analytical value calculated for $C_{23}H_{30}N_3O_7S_3Na$. Theoretical value:C, 47.66; H, 5.22; N, 7.25. Found:C, 47.39; H, 5.5; N, 7.11.

$^1$H-NMR(MeOH-$d_4$) δ ppm; 0.7–0.95 (6H, m, ($CH_3$)$_2$CH—$CH_2$), 1.0–1.7 (3H, m, $CH_2$—CH($CH_3$)$_2$), 1.8–3.6 (9H, m, N—$CH_3$+S—$CH_2CHCH$—$\overline{CO}$+$C_6H_4CH_2$), 4.4–4.7 (1H, m, NH—$\underline{CH}$—CO), 4.85 (3H, brm, 3×$\underline{NH}$), 6.9–7.9 (7H, m, aromatic-H).

EXAMPLE 6

N-[4-(N-Hydroxyamino)-2(R)-n-propyloxymethylene-3(RS)-isopropylthiomethylenesuccinyl]-L-4'-sulfophenylalanine-N-methylamide, Monosodium Salt (a) Benzyl 2(R)-bromo-3-n-propyloxypropionic Acid By the same method as that of Example 3-a, the title compound (1.11 g, 67%) of a colorless oil was obtained from 2(R)-bromo-3-n-propyloxypropionic acid (1.16 g, 5.52 mmol).

Specific rotation$[\alpha]_D$=+0.89° (c=1.2, MeOH), Rf value; 0.61 (n-hexane:AcOEt=5:1).

$^1$H-NMR($CDCl_3$) δ ppm; 0.88 (3H, t, J=7.7 Hz, $CH_3$), 1.3–1.8 (2H, m, $CH_3CH_2$), 3.42 (2H, t, J=6.2 Hz, O—$\overline{CH_2}$), 3.82 (2H, m, $CH_2$—O), 4.35 (1H, m, $\underline{CH}$), 5.22 (2H, s, $CH_2$Ph), 7.38 ($\overline{5H}$, s, aromatic-H).

(b) Dibenzyl 3(RS)-tert-butoxycarbonyl-2(R)-n-propyloxymethylenesuccinate

By the same method as that of Example 3-b, the title compound (22.9 g, 71%) of colorless crystals was obtained from the compound (20.4 g, 67.9 mmol) of Example 6-a.

m.p.; 31–33° C., specific rotation$[\alpha]_D$=+3.22° (c=1.1, MeOH), Rf value; 0.45 (n-hexane:AcOEt=5:1).

$^1$H-NMR($CDCl_3$) δ ppm; 0.82 (3H, 2×t, J=7.7 Hz, $CH_3$), 1.1–1.7 (11H, 2×s+m, $CH_3CH_2$+($CH_3$)$_3$C), 3.1–3.8 ($\overline{5H}$, m, $CH_2$—O—$CH_2$, $CH_2$—$\underline{CH}$—$\overline{CO}$), 3.91 (1H, d, CO—CH—$\overline{CO}$), 5.05–5.22 (4H, m, 2×$CH_2$Ph), 7.35 (10H, s, aromatic-H).

(c) 3-tert-Butoxycarbonyl-2(R)-n-propyloxymethylene-3-butenoic Acid

The compound (3.00 g, 6.38 mmol) of Example 6-b was dissolved in MeOH (100 ml), added with 10% Pd-C (50% wet, 1.5 g) and then stirred vigorously in a stream of hydrogen at room temperature for 6 hours. After the catalyst was filtered off, the filtrate was added with piperidine (694 μl, 7.02 mmol) and stirred at room temperature 15 min. The reaction liquid was added with 36% formalin solution (3.86 ml, 47.5 mmol) at room temperature and stirred at room temperature overnight and further at 80° C. 1 hour. After the solvent was removed under reduced pressure, the residue was dissolved in AcOEt and washed with 5% aqueous citric acid and then a saturated aqueous solution of NaCl two times respectively. The organic layer was dried over anhydrous $MgSO_4$, evaporated under reduced pressure to remove the solvent and purified by column chromatography (silica gel; 50 g, elution with the mixed solvent; $CH_2Cl_2$:AcOEt=7:1) to give the title compound (1.09 g, 66%) of a colorless oil.

$^1$H-NMR($CDCl_3$) δ ppm; 0.89 (3H, t, J=7.7 Hz, $CH_2CH_3$), 1.1–1.75 (11H, s+m, $CH_3CH_2$+($CH_3$)$_3$C), 3.41 (2H, t, J=6.3 Hz, O—$CH_2$—$CH_2$), 3.57–3.98 (3H, m, CO—CHCH$_2$—O), 5.77, 6.34 (2×1H, 2×s, C=$\underline{CH_2}$), 9.2 (1H, brs, OH).

(d) 4-Acetylthio-3(RS)-tert-butoxycarbonyl-2(R)-n-propyloxymethylenebutanoic Acid The compound (700 mg, 2.71 mmol) of Example 6-c and thioacetic acid (5 ml, 70.6 mmol) were mixed and stirred at room temperature overnight. The reaction mixture was purified by column chromatography (silica gel; 100 g, elution with the mixed solvent; $CH_2Cl_2$:MeOH=50:1) to give the title compound (823 mg, 91%) of a colorless oil.

Specific rotation$[\alpha]_D$=−1.74° (c=0.60, MeOH), Rf value; 0.56 ($CHCl_3$:MeOH=10:1).

$^1$H-NMR($CDCl_3$) δ ppm; 0.90 (3H, t, J=7.8 Hz, $CH_2$ $\underline{CH_3}$), 1.1–1.75 (11H, s+m, $CH_3\underline{CH_2}$+$(\underline{CH_3})_3$C), 2.22 (3H, s, $\underline{CH_3}$CO), 2.80–3.55 (6H, m, $\underline{SCH_2}$+$\underline{CH_2}$—O—$\underline{CH_2}$), 3.55–3.90 (2 H, m, 2×CO—$\underline{CH}$).

(e) 3(RS)-tert-Butoxycarbonyl-4-isopropylthio-2(R)-n-propyloxymethylenebutanoic Acid The compound (823 mg, 2.46 mmol) of Example 6-d was dissolved in MeOH (14 ml) under nitrogen atmosphere and dropped with 1N-NaOH (12.3 ml) at room temperature under stirring. After 25 min., the mixture was added with isopropyl iodide (982 μl, 9.84 mmol) and stirred vigorously at room temperature. The reaction mixture was neutralized with 1N-HCl, evaporated under reduced pressure to remove MeOH and acidified by 1N-HCl to pH=2. The organic substances were extracted with AcOEt and washed with a saturated aqueous solution of NaCl two times. The organic layer was dried over anhydrous $MgSO_4$, evaporated under reduced pressure and purified by column chromatography (silica gel; 50 g, elution with the mixed solvent; $CHCl_3$:MeOH=60:1) to give the title compound (653 mg, 80%) of a colorless oil.

Specific rotation$[\alpha]_D$=+0.94° (c=1.1, MeOH), Rf value; 0.46 ($CHCl_3$:MeOH=10:1).

$^1$H-NMR($CDCl_3$) δ ppm; 0.89 (3H, t, J=7.7 Hz, $CH_2$ $\underline{CH_3}$), 1.24 (6H, 2xd, J=7.7 Hz, CH—$(\underline{CH_3})_2$), 1.1–1.80 (11H, s+m, $CH_3\underline{CH_2}$+$(\underline{CH_3})_3$C), 2.60–3.27 (5H, m, O—$\underline{CH_2}$—CH+$\underline{CH}$—S—$\underline{CH_2}$), 3.40 (2H, t, J=6.3 Hz, O—$\underline{CH_2}$—$CH_2$), 3.55–3.80 (2 H, m, 2×CO—$\underline{CH}$).

(f) N-[4-tert-Butoxy-3(RS)-isopropylthiomethylene-2(R)-n-propyloxymethylenesuccinyl]-L-4'-sulfophenylalanine-N-methylamide, Monosodium Salt By the same method as that of Example 2-c, the title compound (653 mg, 80%) of colorless crystals was obtained from the compound of Example 6-e.

m.p.; 254° C. (dec.), specific rotation$[\alpha]_D$=+3.26° (c=0.70, MeOH), Rf value; 0.64 ($CHCl_3$:MeOH:AcOH= 5:2:1), 0.65 (n-BuOH:AcOH:water=4:1:1).

$^1$H-NMR (MeOH-$d_4$) δ ppm; 0.70–1.02 (3H, m, $CH_2$ $\underline{CH_3}$), 1.24 (6H, 2xd, J=7.7 Hz, CH—$(\underline{CH_3})_2$), 1.1–1.8 (11H, s+m, $CH_3\underline{CH_2}$+$(\underline{CH_3})_3$C), 2.5–3.8 (14H, m, NH $\underline{CH_3}$+$C_6H_4$—$\underline{CH_2}$+$\underline{CH_2}$—O—$\underline{CH_2}$+$\underline{CH}$—S— $\underline{CH_2}$+2×CO—$\underline{CH}$), 4.5 (1H, m, NH—$\underline{CH}$—CO), 7.53 (4H, AA'BB', aromatic-H).

(g) N-[4-Hydroxy-3(RS)-isopropylthiomethylene-2(R)-n-propyloxymethylenesuccinyl]-L-4'-sulfophenylalanine-N-methylamide, Monosodium Salt To the compound (1.32 g, 2.22 mmol) of Example 6-f was added ice-cooled 95% aqueous trifluoroacetic acid (40 ml). The reaction mixture was stirred at 5° C.for 2 hours and concentrated under reduced pressure. The residue was added with $Et_2O$ and stirred at room temperature for 1 hour. The precipitating solid was purified by a reverse-phase column chromatography (Fuji Silysia Chemical Ltd., Chromatorex ODS DM-1020T; 90 g, elution with a MeOH-water solution containing 5–15% MeOH) to give the title compound (389 mg, 32%) of colorless powder.

m.p.; 127–137° C., specific rotation$[\alpha]_D$=−8.49° (c=0.99, MeOH), Rf value; 0.48 ($CHCl_3$:MeOH:AcOH=5:2:1), 0.59 (n-BuOH:AcOH:water=4:1:1).

$^1$H-NMR(MeOH-$d_4$) δ ppm; 0.9 (3H, m, $CH_2\underline{CH_3}$), 1.22 (6H, 2xd, J=7.8 Hz, CH—$(\underline{CH_3})_2$), 1.4–1.75 (2H, m, $CH_3$ $\underline{CH_2}$), 2.6–3.8 (14H, m, NH$\underline{CH_3}$+$C_6H_4$—$\underline{CH_2}$+$\underline{CH_2}$—O— $\underline{CH_2}$+$\underline{CH}$—S—$\underline{CH_2}$+2×CO—$\underline{CH}$), 4.55 (1H, m, NH— $\underline{CH}$—CO), 7.53 (4H, AA'BB', aromatic-H).

(h) N-[4-(N-Hydroxyamino)-3(RS)-isopropyl-thiomethylene-2(R)-n-propyloxymethylenesuccinyl]-L-4'-sulfophenylalanine-N-methylamide, Monosodium Salt By the same method as that in Example 4-c, the title compound (236 mg, 62%) of a white solid was obtained from the compound (370 mg, 0.686 mmol) of Example 6-g.

m.p.; 101–107° C., specific rotation$[\alpha]_D$=−2.18° (c=0.53, MeOH), Rf value; 0.41 ($CHCl_3$:MeOH:AcOH=5:2:1), 0.56 (n-BuOH:AcOH:water=4:1:1). Analytical value calculated for $C_{22}H_{34}N_3O_7S_2Na$. Theoretical value:C, 48.97; H, 6.35; N, 7.79. Found:C, 48.79; H, 6.51; N, 7.62.

$^1$H-NMR(MeOH-$d_4$) δ ppm; 0.9 (3H, m, $CH_2\underline{CH_3}$), 1.22 (6H, 2xd, J=7.7 Hz, CH—$(\underline{CH_3})_2$), 1.4–1.75 (2H, m, $CH_3$ $\underline{CH_2}$), 2.6–3.8 (14H, m, NH$\underline{CH_3}$+$C_6H_4$—$\underline{CH_2}$+$\underline{CH_2}$—O— $\underline{CH_2}$+$\underline{CH}$—S—$\underline{CH_2}$+2×CO—$\underline{CH}$), 4.55 (1H, m, NH— $\underline{CH}$—CO), 7.53 (4H, AA'BB', aromatic-H).

EXAMPLE 7

N-[4-(N-Hydroxyamino)-2(R)-isobutyl-3(RS)-(3-phenyltrimethylene)succinyl]-O-sulfo-L-tyrosine-N-p-methoxyphenylamide, Monosodium Salt By the same methods as used in c–g of Example 1, the following compounds were synthsized from the compound of Example 3-d and L-tyrosine-N-p-methoxyphenylamide hydrochlodide.

(a) N-[4-tert-Butoxy-2(R)-isobutyl-3(RS)-(3-phenyltrimethylene)succinyl]-L-tyrosine-N-p-methoxyphenylamide White solid (86%), m.p.; 87–89° C., specific rotation$[\alpha]_D$=−27.0° (c=1.02, $CHCl_3$), Rf value; 0.56 (AcOEt:n-hexane=1:1).

$^1$H-NMR($CDCl_3$) δ ppm; 0.77 (6H, m, CH$(CH_3)_2$), 0.9–1.8 (16H, s+m, $(CH_3)_2$CH—$CH_2$+C$(\underline{CH_3})_3$+ $\underline{CH_2}$—$\underline{CH_2}$—$\underline{CH_2}$—Ph), 2.1–2.7 (4H, m, —$\underline{CH}$—CO×2+ $\underline{CH_2}$—Ph), 2.8–3.2 (2H, m, $C_6H_4\underline{CH_2}$), 3.74 (3H, s, O$\underline{CH_3}$), 4.78 (1H, m, NH—$\underline{CH}$—CO), 6.3–7.6 (13H, m, aromatic-H).

(b) N-[4-(N-Benzyloxyamino)-2(R)-isobutyl-3(RS)-(3-phenyltrimethylene)succinyl]-L-tyrosine-N-p-methoxyphenylamide White powder (41%), m.p.; 241–244° C., specific rotation $[\alpha]_D$=+9.39° (c=1.0, DMF), Rf value; 0.24 ($CHCl_3$:MeOH= 20:1).

$^1$H-NMR(DMSO-$d_6$) δ ppm; 0.4–1.6(13H, m, $(CH_3)_2$CH—$CH_2$+$CH_2$—$CH_2$—$CH_2$—Ph), 1.8–2.6 (4H, m, —$\underline{CH}$—CO×2+$\underline{CH_2}$—Ph), 2.92 (2H, m, $C_6H_4\underline{CH_2}$), 3.72 (3H, s, O$\underline{CH_3}$), 4.4–4.8 (3H, s+m, O—$\underline{CH_2}$—Ph+NH— $\underline{CH}$—CO), 6.5–7.6 (18H, m, aromatic-H), 8.32 (1H, m, NH).

(c) N-[4-(N-Benzyloxyamino)-2(R)-isobutyl-3(RS)-(3-phenyltrimethylene)succinyl]-O-sulfo-L-tyrosine-N-p-methoxyphenylamide White amorphous powder (71%), specific rotation$[\alpha]_D$=− 16.8° (c=1.0, MeOH), Rf value; 0.66 ($CHCl_3$:MeOH:AcOH=5:2:1).

$^1$H-NMR(DMSO-$d_6$) δ ppm; 0.5–1.0 (6H, m, $(CH_{32})CH$—$CH_2$), 1.0–1.7 (7H, m, $(CH_3)_2$CH—$CH_2$+ $\underline{CH_2}$—$\underline{CH_2}$—$\underline{CH_2}$—Ph), 1.8–2.7 (4H, m, —$\underline{CH}$—CO×2+ $\underline{CH_2}$—Ph), 2.8–3.2 (2H, m, $C_6H_4\underline{CH_2}$), 3.74 (3H, s, O$\underline{CH_3}$), 4.5–5.1 (3H, s+m, O—$\underline{CH_2}$—Ph+NH—$\underline{CH}$—CO), 6.2–7.6 (18H, m, aromatic-H).

(d) N-[4-(N-Hydroxyamino)-2(R)-isobutyl-3(RS)-(3-phenyltrimethylene)succinyl]-O-sulfo-L-tyrosine-N-p-methoxyphonylamide, Monosodium Salt White amorphous powder (73%), specific rotation$[\alpha]_D$=−7.4° (c=1.1, DMF), Rf value; 0.45 (CHCl$_3$:MeOH:AcOH= 5:2:1). Analytical value calculated for C$_{33}$H$_{40}$N$_3$O$_9$SNa. Theoretical value:C, 58.48; H, 5.95; N, 6.2. Found:C, 58.27; H, 6.2; N, 6.01.

$^1$H-NMR(MeOH-d$_4$) δ ppm; 0.5–1.8 (13H, m, (CH$_3$)CH$_2$CH—CH$_2$+CH$_2$—CH$_2$—CH$_2$—Ph), 1.9–2.7 (4H, m, —CH—CO×2+CH$_2$—Ph), 2.8–3.2 (2H, m, C$_6$H$_4$CH$_2$), 3.73 and 3.75 (3H, s each, OCH$_3$), 4.5–5.0 (1H, m, NH—CH—CO), 6.6–7.6 (18H, m, aromatic-H).

EXAMPLE 8

N-[4-(N-Hydroxyamino)-2(R)-isobutyl-3(R or S)-(3-phenyltrimethylene)succinyl]-L-4'-guanidophenylalanine-N-methylamide Monoacetate (a) N$^\alpha$-tert-Butyloxycarbonyl-L-4'-[N,N'-bis(benzyloxycarbonyl)guanido]phenylalanine-N-methylamide N$^\alpha$-tert-Butyloxycarbonyl-L-4'-aminophenylalanine-N-methylamide (2.00 g, 6.82 mmol) was dissolved in CH$_2$Cl$_2$ (30 ml), added with 1H-pyrazole-N,N'-bis(benzyloxycarbonyl) carboxamidine (2.84 g, 7.51 mmol) and stirred at room temperature for 3 hours. The reaction mixture was concentrated under reduced pressure, dissolved in AcOEt (30 ml) and stirred for 30 min. The resulting crystals were dried to give the title compound (3.95 g, 96%) of a white solid.

m.p.; 168° C., specific rotation$[\alpha]_D$=+14.1° (c=1.0, CHCl$_3$), Rf value; 0.20 (CHCl$_3$:MeOH=50:1).

$^1$H-NMR(CDCl$_3$) δ ppm; 1.40 (9H, s, C(CH$_3$)$_3$), 2.69 (3H, d, J=4.8 Hz, N—CH$_3$), 3.00 (2H, d, J=6.8 Hz, C$_6$H$_4$CH$_2$), 4.9–5.4 (5H, m+s, OCH$_2$Ph×2+NH), 6.00 (1H, m, NH), 7.0–7.7 (16H, m, aromatic-H+NH×2).

(b) N-[4-tert-Butoxy-2(R)-isobutyl-3(R or S)-(3-phenyltrimethylene)succinyl]-L-4'-[N,N'-bis(benzyloxycarbonyl)guanido]phenylalanine-N-methylamide The compound (142 g, 235 mmol) of Example 8-a was dissolved in an AcOEt solution of HCl (4N, 1000 ml) and stirred under ice-cooling for 45 min. The reaction mixture was added with Et$_2$O (150 ml) and stirred. The precipitating crystals were filtered, washed with Et$_2$O (100 ml) five times, and dried.

The obtained crystals (127 g, 235 mmol), the compound (73.9 g, 212 mmol) of Example 3-d and HOBT (30.1 g, 223 mmol) were dissolved in DMF (50 ml) and CH$_2$Cl$_2$ (1200 ml) and added with TEA (32.8 ml, 235 mmol) and EDC (44.7 g, 233 mmol) at −15° C. under stirring. The mixture was stirred at −15° C. for 1 hour and further at room temperature overnight and evaporated under reduced pressure. The residue was purified by column chromatography (silica gel; 12 Kg, elution with the mixed solvent; CH$_2$Cl$_2$:AcOEt=6:1–2:1) to give the title compound (isomer A; 65.0 g, 37%, and isomer B; 58.0 g, 33%) of a white solid.

Isomer A m.p.; 191° C., specific rotation$[\alpha]_D$=−10.1° (c=1.0, CHCl$_3$), Rf value; 0.28 (n-hexane:AcOEt=1:1).

$^1$H-NMR(CDCl$_3$) δ ppm; 0.82 (6H, m, CH(CH$_3$)$_2$), 0.92–2.1 (16H, s+m, (CH$_3$)$_2$CH—CH$_2$, +C(CH$_3$)$_3$+CH$_2$—CH$_2$—CH$_2$—Ph), 2.1–2.6 (4H, m, —CH—CO×2+CH$_2$—Ph), 2.67 (3H, d, J=4.6 Hz, N—CH$_3$), 2.93 (2H, d, J=5.9 Hz, C$_6$H$_4$CH$_2$), 4.56 (1H, m, NH—CH—CO), 5.13 and 5.18 (4H, s each, OCH$_2$Ph×2), 5.98 (1H, m, NH), 6.50 (1H, m, NH), 6.8–7.65 (21H, m, aromatic-H+NH×2).

Isomer B m.p.; 160° C., specific rotation$[\alpha]_D$=+10.70° (c=1.0, CHCl$_3$), Rf value; 0.37 (n-hexane:AcOEt=1:1).

$^1$H-NMR(CDCl$_3$) δ ppm; 0.80 (6H, m, CH(CH$_3$)$_2$), 0.9–1.95 (16H, s+m, (CH$_3$)$_2$CH—CH$_2$, +C(CH$_3$)$_3$+CH$_2$—CH$_2$—CH$_2$—Ph), 2.0–2.6 (4H, m, —CH—CO×2+CH$_2$—Ph), 2.68 (3H, d, J=4.6 Hz, N—CH$_3$), 3.01 (2H, d, J=5.9 Hz, C$_6$H$_4$CH$_2$), 4.61 (1H, m, NH—CH—CO), 5.15 and 5.23 (4H, s each, OCH$_2$Ph×2), 5.8–6.3 (2H, m, NH×2), 6.95–7.75 (21H, m, aromatic-H+NH×2).

(c) N-[4-(N-Benzyloxyamino)-2(R)-isobutyl-3(R or S)-(3-phenyltrimethylene)succinyl]-L-4'-[N,N'-bis(benzyloxycarbonyl)guanido]phenylalanine-N-methylamide To the compound (isomer A, 56.0 g, 67.1 mmol) of Example 8-b was added ice-cooled 95% aqueous trifluoroacetic acid (420 ml). The reaction mixture was stirred at 5° C. overnight and concentrated under reduced pressure. The residue was added with Et$_2$O and stirred at room temperature for 1 hour. The precipitating solid was filtered and dried to give a white solid (54.7 g).

The obtained white solid, O-benzylhydroxylamine hydrochloride (16.8 g, 105 mmol) and HOBT (10.5 g, 77.3 mmol) were suspended in DMF (1400 ml). The suspension was added with TEA (15.2 ml, 109 mmol) and EDC (20.1 g, 105 mmol) at −15° C. under stirring. The mixture was stirred at −15° C. for 1 hour and further at room temperature overnight and dropped with ice-water (3000 ml). The precipitating solid was filtered, suspended in MeOH (3000 ml) and stirred at room temperature for 1 hour. The insoluble material was filtered and dried in a desiccator under reduced pressure to give the title compound (47.0 g, 76%) of a white solid.

m.p.; 220° C. (dec.), Rf value; 0.58 (CHCl$_3$:MeOH= 10:1).

(d) N-[4-(N-Hydroxyamino)-2(R)-isobutyl-3(R or S)-(3-phenyltrimethylene)succinyl]-L-4'-guanidophenylalanine-N-methylamide Monoacetate The compound (7.00 g, 7.90 mmol) of Example 8-c was suspended in AcOH (200 ml), added with 5% Pd-C (50% wet, 4.0 g) and then stirred vigorously in a stream of hydrogen at room temperature for 3 hours. After the catalyst was filtered off, AcOH of the filtrate was removed under reduced pressure. The residue was suspended in AcOEt (300 ml) and stirred for 30 min. The insoluble material was filtered, dried in a desiccator under reduced pressure, added with water (370 ml) and lyophilized, whereby the title compound (4.30 g, 93%) of white amorphous powder was obtained.

Specific rotation$[\alpha]_D$=−10.2° (c=1.0, MeOH), Rf value; 0.48 (CHCl$_3$:MeOH:AcOH=95:5:3). Analytical value calculated for C$_{30}$H$_{44}$N$_6$O$_6$, Theoretical value:C, 61.62; H, 7.58; N, 14.37. Found:C, 61.72; H, 7.5; N, 14.12.

$^1$H-NMR(MeOH-d$_4$) δ ppm; 0.5–1.8 (13H, m, (CH$_3$)$_2$CH—CH$_2$, +CH$_2$—CH$_2$—CH$_2$—Ph), 1.89(3H, s, CH$_3$COOH), 2.0–2.8 (7H, m, N—CH$_3$+—CH—CO×2+CH$_2$—Ph), 2.96 (2H, m, C$_6$H$_4$CH$_2$), 4.4–5.0 (1H, m, NH—CH—CO), 6.8–7.5 (9H, m, aromatic-H).

EXAMPLE 9

N-[4-(N-Hydroxyamino)-2(R or S)-isobutylsuccinyl]-O-phospho-L-tyrosine-N-methylamide, Disodium Salt (a) N-[4-(N-Benzyloxyamino)-2 (R or S)-isobutylsuccinyl]-O-di-tert-butylphospho-L-tyrosine-N-methylamide The isomer B (2.56 g, 5.62 mmol) of Example 1-e and 1H-tetrazole (1.18 g, 16.8 mmol) were dissolved in DMF (25 ml) at room temperature, added with di-tert-butyl N,N-diethylphosphoramidite (93% purity, 1.88 g, 7.01 mmol) and stirred at room temperature for 2 hours. The reaction mixture was cooled to −78° C. and dropped with a solution of m-chloroperbenzoic acid (1.80 g, 7.34 mmol) in $CH_2Cl_2$ (25 ml). The mixture was warmed to room temperature, stirred for 1 hour, diluted with chloroform (200 ml) and washed with 0.05N-HCl and a saturated aqueous solution of $NaHCO_3$ two times respectively. The organic layer was dried over anhydrous $MgSO_4$, removed under reduced pressure, added with $Et_2O$ and stirred at room temperature for 1 hour. The precipitating solid was filtered and dried in a desiccator under reduced pressure to give the tile compound (2.84 g, 80%) of a white solid.

m.p.; 175–177° C., specific rotation$[\alpha]_D$=−17.7° (c=1.0, MeOH), Rf value; 0.76 ($CHCl_3$:MeOH:AcOH=5:2:1), 0.52 ($CHCl_3$:MeOH=10:1).

$^1$H-NMR ($CDCl_3$) δ ppm; 0.82 (6H, m, $CH(CH_3)_2$), 1.49 (9H, s, $C(CH_3)_3$), 1.0–2.0(3H, m, $(CH_3)_2\overline{CH}$—$\overline{CH_2}$), 2.2 (2H, m, $\overline{CH_2CO}$), 2.5–3.5 (6H, m, N—$\overline{CH_3}$+CO—$\overline{CH_2}$ $\overline{CH}$—CO+$\overline{CH_2}$—$C_6H_4$), 4.5–5.1 (3H, m, $\overline{NH}$—$\overline{CH}$—CO+$\overline{O}$ $\overline{CH_2}Ph$), 6.7–7.6 (14H, m, aromatic-H+NH×3).

(b) N-[4-(N-Benzyloxyamino)-2(R or S)-isobutylsuccinyl]-O-phospho-L-tyrosine-N-methylamide, Disodium Salt To the compound (2.72 g, 4.20 mmol) of Example 9-a was added ice-cooled 90% aqueous trifluoroacetic acid (42 ml). The reaction mixture was stirred at 5° C. for 1 hour and concentrated under reduced pressure. The residue was added with $Et_2O$ and stirred at room temperature for 1 hour. The precipitating solid was filtered and dried to give a white solid (1.74 g). The obtained white solid was dissolved in aqueous 1N-$NaHCO_3$ (13 ml) and purified by a reverse-phase column chromatography (Fuji Silysia Chemical Ltd., Chromatorex ODS DM-1020T; 100 g, elution with a MeOH-water solution containing 0–20% MeOH) to give the title compound (1.39 g, 57%) of white amorphous powder upon freeze-drying.

Specific rotation$[\alpha]_D$=−11.2° (c=1.0, MeOH), Rf value; 0.08 ($CHCl_3$:MeOH:AcOH=5:2:1), 0.47 (n-BuOH:AcOH:water=4:1:1).

$^1$H-NMR(MeOH-$d_4$) δ ppm; 0.5–1.8 (9H, m, $(CH_3)_2CH$—$CH_2$), 2.1 (2H, m, $\overline{CH_2CO}$), 2.5–3.2 (6H, m, $\overline{N}$—$\overline{CH_3}$+CO—$\overline{CH_2CH}$—CO+$\overline{CH_2}$—$C_6H_4$), 4.3–5.2 (3H, m, $\overline{NH}$—$\overline{CH}$—CO+$\overline{OCH_2}Ph$), 6.9–7.6 (9H, m, aromatic-H).

(c) N-[4-(N-Hydroxyamino)-2(R or S)-isobutylsuccinyl]-O-phospho-L-tyrosine-N-methylamide, Disodium Salt The compound (1.26 g, 2.17 mmol) of Example 9-b was dissolved in MeOH (50 ml), added with 5% Pd-C (50% wet, 1.26 g), and then stirred vigorously in a stream of hydrogen at room temperature for 4 hours. After the catalyst was filtered off, MeOH of the filtrate was removed under reduced pressure. The residue was suspended in water (50 ml) and stirred for 30 min. The insoluble material was filtered and the filtrate was lyophilized, whereby the title compound (790 mg, 75%) of white amorphous powder was obtained.

Specific rotation$[\alpha]_D$=+10.6° (c=1.0, water), Rf value; 0.31 (n-BuOH:AcOH:water=4:1:1). Analytical value calculated for $C_{18}H_{26}N_3O_8Na_2P$. Theoretical value:C, 44.18; H, 5.36; N, 8.59. Found:C, 43.91; H, 5.48; N, 8.55.

$^1$H-NMR(MeOH-$d_4$+$D_2O$) δ ppm; 0.5–1.8 (9H, m, $(CH_3)_2CH$—$CH_2$), 2.1 (2H, m, $\overline{CH_2CO}$), 2.4–3.2 (6H, m, $\overline{N}$—$\overline{CH_3}$+CO—$\overline{CH_2CH}$—CO+$\overline{CH_2}$—$C_6H_4$), 4.3–4.8 (1H, m, $\overline{NH}$—$\overline{CH}$—CO), 7.15 (4H, s, aromatic-H).

EXAMPLE 10

N-[4-(N-Hydroxyamino)-2(R)-isobutyl-3(R or S)-(3-phenyltrimethylene)succinyl]-L-4'-acetimidoyliminomethylenephenylalanine-N-methylamide Monoacetate (a) N-[4-tert-Butoxy-2(R)-isobutyl-3(R or S)-(3-phenyltrimethylene)succinyl]-L-4'-cyanophenylalanine-N-methylamide The compound (3.62 g, 10.4 mmol) of Example 3-d, L-4'-cyanophenylalanine-N-methylamide hydrochloride (3.62 g, 10.4 mmol) and HOBT (1.55 g, 11.5 mmol) were dissolved in DMF (70 ml) and added with TEA (1.40 ml, 12.5 mmol) and EDC (2.40 g, 12.5 mmol) at −15° C. under stirring. The mixture was stirred at −15° C. for 1 hour and further at 5° C. overnight and removed under reduced pressure. The residue was dissolved in AcOEt (200 ml), and washed with a saturated aqueous solution of NaCl, 1N-HCl, a saturated aqueous solution of $NaHCO_3$ and then the saturated aqueous solution of NaCl two times respectively. The organic layer was dried over anhydrous $MgSO_{41}$ evaporated under reduced pressure to remove the solvent, purified by column chromatography (silica gel; 1 Kg, elution with the mixed solvent; $CHCl_3$MeOH=50:1) and recrystallized from AcOEt-n-hexane to give the title compound (1.71 g, 31%) of a white solid.

m.p.; 196–198° C., specific rotation$[\alpha]_D$=−13.3° (c=1.1, MeOH), Rf value; 0.65 ($CHCl_3$:MeOH=10:1), 0.52 ($CHCl_3$:MeOH:AcOH=95:5:3).

$^1$H-NMR($CDCl_3$) δ ppm; 0.81 (6H, m, $CH(CH_3)_2$), 0.9–1.8 (16H, s+m, $(CH_3)_2CH$—$CH_2$, +$\overline{C(CH_3)_3}$+ $\overline{CH_2}$—$CH_2$—$CH_2$—Ph), 2.1–2.85 (7H, d+m, J=4.6 Hz, N— $\overline{CH_3}$+—$\overline{CH}$—CO×2+$CH_2$—Ph), 3.02 (2H, m, $C_6H_4\underline{CH_2}$), $\overline{4.62}$ (1H, m, NH—$\underline{CH}$—CO), 6.10 (1H, m, NH), 6.50 (1H, m, NH), 6.9–7.7 (9H, m, aromatic-H).

(b) N-[4-Hydroxy-2(R)-isobutyl-3(R or S)-(3-phenyltrimethylene)succinyl]-L-4'-cyanophenylalanine-N-methylamide To the compound (1.73 g, 3.24 mmol) of Example 10-a was added ice-cooled 95% aqueous trifluoroacetic acid (16 ml). The reaction mixture was stirred at 5° C. for 4 hours and concentrated under reduced pressure. The concentrate was added with $Et_2O$ and stirred at room temperature for 1 hour. The precipitating solid was filtered and dried to give the title compound (1.22 g, 79%) of a white solid.

m.p.; 234–235° C., specific rotation$[\alpha]_D$=−8.7° (c=1.1, MeOH), Rf value; 0.35 ($CHCl_3$:MeOH=10:1), 0.46 ($CHCl_3$:MeOH:AcOH=95:5:3).

$^1$H-NMR(MeOH-$d_4$) δ ppm; 0.83 (6H, m, $CH(CH_3)_2$), 0.95–1.85 (7H, m, $(CH_3)_2CH$—$CH_2$, + $CH_2$—$CH_2$—$CH_2$—Ph), 2.2–3.2 (9H, m, $\overline{N}$—$\overline{CH_3}$+— $\overline{CH}$—CO×2+$CH_2$—Ph+$C_6H_4\underline{CH_2}$), 4.60 (1H, m, $\overline{NH}$— $\underline{CH}$—CO), 6.9–7.25 (9H, m, aromatic-H).

(c) N-[4-Hydroxy-2(R)-isobutyl-3(R or S)-(3-phenyltrimethylene)succinyl]-L-4'-aminomethylenephenylalanine-N-methylamide Hydrochloride The compound (1.22 g, 2.55 mmol) of Example 10-b was dissolved in ethanol (25 ml), added with conc. HCl (1 ml) and 5% Pd-C (50% wet, 600 mg) and then stirred vigorously in a stream of hydrogen at room temperature for 10 hours. After the catalyst was filtered off, ethanol of the filtrate was removed under reduced pressure. The residue was suspended in water (50 ml) and stirred for 30 min. The insoluble material was taken by filtration and dried in a desiccator under reduced pressure, added with $Et_2O$, and stirred at room temperature for 1 hour. The precipitating solid was filtered and dried in the desiccator under reduced pressure to give the title compound (1.15 g, 94%) of a white solid.

m.p.; 194–202° C., specific rotation$[\alpha]_D$=−15.1° (c=1.0, MeOH), Rf value; 0.32 ($CHCl_3$:MeOH:AcOH=5:2:1).

$^1$H-NMR(MeOH-$d_4$) δ ppm; 0.6–0.95 (6H, m, CH $(CH_3)_2$), 1.0–1.8 (7H, m, $(CH_3)_2CH$—$CH_2$, + $\overline{CH_2}$—$CH_2$—$CH_2$—Ph), 2.2–2.7 (7H, m, $\overline{N}$—$\overline{CH_3}$+— $\overline{CH}$—CO×2+$CH_2$—Ph), 2.95 (2H, m, $C_6H_4\underline{CH_2}$), $\overline{4.0}$ (2H, brs, $\underline{CH_2}$—$\overline{NH_2}$), 4.63 (1H, m, NH—$\underline{CH}$—CO), 6.9–7.6 (9H, m, aromatic-H).

(d) N-[4-Hydroxy-2(R)-isobutyl-3(R or S)-(3-phenyltrimethylene)succinyl]-L-4'-acetimidoyliminomethylenephenylalanine-N-methylamide Hydrochloride The compound (530 mg, 1.02 mmol) of Example 10-c was dissolved in DMF (10 ml), added with ethyl acetimidate hydrochloride (252 mg, 2.04 mmol) and TEA (416 μl, 3.00 mmol) under stirring in an ice bath and stirred for 1 hour. The DMF was removed under reduced pressure. The residue was added with 1N-HCl to adjust pH to 2, and then purified by DIAION HP-20 (Mitsubishi Chemicals; 100 ml, elution with a MeOH-water solution containing 10–80% MeOH), whereby water (20 ml) was added to give the title compound (511 mg, 65%) of white amorphous powder upon freeze-drying.

Specific rotation$[\alpha]_D$=−16.50° (c=1.0, MeOH), Rf value; 0.23 ($CHCl_3$:MeOH:AcOH=5:2:1).

$^1$H-NMR(MeOH-$d_4$) δ ppm; 0.5–1.0 (6H, m, CH($CH_3$)$_2$), 1.0–1.8 (7H, m, ($CH_3$)$_2$CH—$CH_2$, + $CH_2$—$CH_2$—$CH_2$—Ph), 2.17 (3H, s, C—$CH_3$), 2.26–2.77 (7H, m, N—$CH_3$+—CH—CO×2+$CH_2$—Ph), 2.8–3.2 (2H, m, $C_6H_4CH_2$), 4.38 (2H, brs, $CH_2$—NH), 4.58(1H, m, NH—CH—CO), 6.8–7.55 (9H, m, aromatic-H).

(e) N-[4-(N-Bezyloxyamino-2(R)-isobutyl-3(R or S)-(3-phenyltrimethylene)succinyl]-L-4'-acetimidoyliminomethylenephenylalanine-N-methylamide Hydrochloride The compound (465 mg, 0.832 mmol) of Example 10-d, O-benzylhydroxylamine hydrochloride (200 mg, 1.25 mmol) and HOBT (169 mg, 1.25 mmol) were suspended in DMF (10 ml). The suspension was added with TEA (288 μl, 2.08 mmol) and EDC (240 mg, 1.25 mmol) at −15° C. under stirring. The mixture was stirred at −15° C. for 1 hour and further at room temperature overnight. The DMF was removed under reduced pressure. The residue was added with 1N-HCl to adjust pH to 2 and then purified by DIAION HP-20 (Mitsubishi Chemicals; 100 ml, elution with a MeOH-water solution containing 20–80% MeOH) and column chromatography (silica gel; 50 g, elution with the mixed solvent; $CHCl_3$:MeOH=9:1–1:1, MeOH and AcOH), whereby water (20 ml) was added to give the title compound (420 mg, 76%) of white amorphous powder upon freeze-drying.

Specific rotation$[\alpha]_D$=−1.3° (c=1.0, MeOH), Rf value; 0.25 ($CHCl_3$:MeOH:AcOH=5:2:1).

$^1$H-NMR(MeOH-$d_4$) δ ppm; 0.5–1.7(13H, m, ($CH_3$)$_2$CH—$CH_2$, +$CH_2$—$CH_2$—$CH_2$—Ph), 1.90(3H, s, $CH_3$COOH), 2.0–3.1 (12H, s+m, C—$CH_3$+N—$CH_3$+—CH—CO×2+$CH_2$—Ph+$C_6H_4CH_2$), 4.36 (2H, brs, $CH_2$—NH), 4.4–5.2 (3H, s+m, NH—CH—CO+OCH$_2$Ph), 6.8–7.6 (14H, m, aromatic-H).

(f) N-[4-(N-Hydroxyamino)-2(R)-isobutyl-3(R or S)-(3-phenyltrimethylene)succinyl]-L-4'-acetimidoyliminomethylenephenylalanine-N-methylamide Monoacetate The compound (200 mg, 0.291 mmol) of Example 10-e was dissolved in AcOH (10 ml), added with 5% Pd-C (50% wet, 200 mg), and then stirred vigorously in a stream of hydrogen at room temperature for 30 hours. After the catalyst was filtered off, AcOH of the filtrate was removed under reduced pressure. The residue was added with water (10 ml) to give the title compound (159 mg, 91%) of a white amorphous powder upon freeze-drying.

Specific rotation$[\alpha]_D$=−8.9° (c=1.0, MeOH), Rf value; 0.13 ($CHCl_3$:MeOH:AcOH=5:2:1), 0.50(n-BuOH:AcOH:water=4:1:1). Analytical value calculated for $C_{32}H_{47}N_5O_6$. Theoretical value:C, 64.3; H, 7.93; N, 11.72. Found:C, 64.35; H, 8.01; N, 11.68.

$^1$H-NMR(MeOH-$d_4$) δ ppm; 0.5–1.7 (13H, m, ($CH_3$)$_2$CH—$CH_2$+$CH_2$—$CH_2$—$CH_2$—Ph), 1.90(3H, s, $CH_3$COOH), 2.0–3.1 (12H, s+m, C—$CH_3$+N—$CH_3$+—CH—CO×2+$CH_2$—Ph+$C_6H_4CH_2$), 4.36 (2H, brs, $CH_2$—NH), 4.6 (1H, m, NH—CH—CO), 6.8–7.6 (9H, m, aromatic-H).

EXAMPLE 11

N-[4-(N-Hydroxyamino)-2(R)-isobutyl-3(R or S)-(3-phenyltrimethylene)succinyl]-L-4'propionimidoyliminomethylenephenylalanine-N-methylamide Monoacetate By the same methods as used in d–f of Example 10, the following compounds were synthesized from the compound of Example 10-c and ethyl propionimidate hydrochloride.

(a) N-[4-Hydroxy-2(R)-isobutyl-3(R or S)-(3-phenyltrimethylene)succinyl]-L-4'-propionimidoyliminomethylenephenylalanine-N-methylamide Hydrochloride White amorphous powder (79%), specific rotation$[\alpha]_D$=−14.1° (c=0.2, MeOH), Rf value; 0.32 ($CHCl_3$:MeOH:AcOH=5:2:1).

$^1$H-NMR(MeOH-$d_4$) δ ppm; 0.5–1.0 (6H, m, CH($CH_3$)$_2$), 1.0–1.8 (10H, m, ($CH_3$)$_2$CH—$CH_2$, + $CH_2$—$CH_2$—$CH_2$—Ph+$CH_2$—$CH_3$), 2.2–2.75 (9H, m, N—$CH_3$+—CH—CO×2+$CH_2$—Ph+$CH_2$—$CH_3$), 2.95 (2H, m, $C_6H_4CH_2$), 4.38 (2H, brs, $CH_2$—NH), 4.59 (1H, m, NH—CH—CO), 6.9–7.5 (9H, m, aromatic-H).

(b) N-[4-(N-Bezyloxyamino-2(R)-isobutyl-3(R or S)-(3-phenyltrimethylene)succinyl]-L-4'-propionimidoyl-iminomethylenephenylalanine-N-methylamide Hydrochloride White amorphous powder (76%), specific rotation$[\alpha]_D$=−4.4° (c=1.0, MeOH), Rf value; 0.53 ($CHCl_3$:MeOH:AcOH=5:2:1).

$^1$H-NMR(MeOH-$d_4$) δ ppm; 0.55–1.0 (6H, m, CH($CH_3$)$_2$), 1.0–1.75 (10H, m, ($CH_3$)$_2$CH—$CH_2$,+ $CH_2$—$CH_2$—$CH_2$—Ph+$CH_2$—$CH_3$), 2.2–2.8 (9H, m, N—$CH_3$+—CH—CO×2+$CH_2$—Ph+$CH_2$—$CH_3$), 2.95(2H, m, $C_6H_4CH_2$), 4.4–4.75 (3H, m $CH_2$—NH+NH—CH—CO), 4.84 (2H, s, OCH$_2$Ph), 6.9–7.6 (14H, m, aromatic-H).

(c) N-[4-(N-Hydroxyamino)-2(R)-isobutyl-3(R or S)-(3-phenyltrimethylene)succinyl]-L-4'-propionimidoyliminomethylenephenylalanine-N-methylamide Monoacetate White amorphous powder (91%), specific rotation$[\alpha]_D$=−9.7° (c=0.2, MeOH), Rf value; 0.35 ($CHCl_3$:MeOH:AcOH=5:2:1). Analytical value calculated for $C_{33}H_{49}N_5O_6$. Theoretical value:C, 64.79; H, 8.07; N, 11.45. Found:C, 64.95; H, 8.12; N, 11.38.

$^1$H-NMR(MeOH-$d_4$) δ ppm; 0.5–1.75 (16H, m, ($CH_3$)$_2$CH—$CH_2$, +$CH_2$—$CH_2$—$CH_2$—Ph+$CH_2$—$CH_3$), 1.88 (3H, s, $CH_3$COOH), 2.2–3.2 (11H, m, N—$CH_3$+—CH—CO×2+$CH_2$—Ph+$C_6H_4CH_2$+$CH_2$—$CH_3$), 4.38 (2H, brs, $CH_2$—NH), 4.45–4.8 (1H, m, NH—CH—CO), 6.9–7.5 (9H, m, aromatic-H).

EXAMPLE 12

N-[4-(N-Hydroxyamino)-2(R)-isobutyl-3(RS)-(3-phenyltrimethylene)succinyl]-L-4'-benzimidoyliminomethylenephenylalanine-N-methylamide Monoacetate By the same methods as used in d–f of Example 10, the following compounds were synthesized from the compound (3-RS type) of Example 10-c and ethyl benzimidate hydrochloride.

(a) N-[4-Hydroxy-2(R)-isobutyl-3(RS)-(3-phenyltrimethylene)succinyl]-L-4'-benzimidoyl-iminomethylenephenylalanine-N-methylamide Hydrochloride White amorphous powder (71%), specific rotation$[\alpha]_D$=−9.0° (c=1.0, MeOH), Rf value; 0.34 ($CHCl_3$:MeOH:AcOH=5:2:1).

¹H-NMR(MeOH-d₄) δ ppm; 0.4–0.95 (6H, m, CH(CH₃)₂, 0.95–1.8 (7H, m, (CH₃)₂CH—CH₂, + CH₂—CH₂—CH₂—Ph), 2.1–2.8 (7H, m, N—CH₃+—CH—CO×2+CH₂—Ph), 2.95 (2H, m, C₆H₄CH₂), 3.6–4.6 (4H, m, CH₂—NH+NH—CH—CO), 6.9–8.0 (14H, m, aromatic-H).

(b) N-[4-(N-Bezyloxyamino)-2(R)-isobutyl-3(RS)-(3-phenyltrimethylene)succinyl]-L-4'-benzimidoyl-iminomethylenephenylalanine-N-methylamide Hydrochloride White amorphous powder (92%), specific rotation[α]$_D$=−4.6° (c=1.1, MeOH), Rf value; 0.41 (CHCl₃:MeOH:AcOH= 5:2:1).

¹H-NMR(MeOH-d₄) δ ppm; 0.5–1.0 (6H, m, CH(CH₃)₂), 1.0–1.8 (7H, m, (CH₃)₂CH—CH₂, + CH₂—CH₂—CH₂—Ph), 1.8–3.3 (9H, m, N—CH₃+—CH—CO×2+CH₂—Ph+C₆H₄CH₂), 4.4–5.1 (5H, m, CH₂—NH+NH—CH—CO+OCH₂Ph), 6.9–8.1 (19H, m, aromatic-H).

(c) N-[4-(N-Hydroxyamino)-2(R)-isobutyl-3(RS)-(3-phenyltrimethylene)succinyl]-L-4'-benzimidoyl-iminomethylenephenylalanine-N-methylamide Monoacetate White amorphous powder (79%), specific rotation[α]$_D$=−4.3° (c=1.1, MeOH), Rf value; 0.54 (CHCl₃:MeOH:AcOH= 5:2:1). Analytical value calculated for CH₃₇H₄N₅O₆. Theoretical value:C, 67.35; H, 1.49; N, 10.61. Found:C, 67.6; H, 7.34; N, 10.44.

¹H-NMR(MeOH-d₄) δ ppm; 0.55–1.85 (13H, m, (CH₃)₂CH—CH₂, +CH₂—CH₂—CH₂—Ph), 1.93 (3H, s, CH₃COOH), 2.0–3.4 (9H, m, N—CH₃+—CH—CO×2+CH₂—Ph+C₆H₄CH₂), 4.4–4.8 (3H, m, CH₂—NH+NH—CH—CO), 7.0–7.9 (14H, m, aromatic-H).

EXAMPLE 13

N-[4-(N-Hydroxyamino)-2(R)-isobutyl-3(RS)-(3-phenyltrimethylene)succinyl]-L-4'-acetamidomethylenephenylalanine-N-methylamide (a) N-[4-Hydroxy-2(R)-isobutyl-3(RS)-(3-phenyltrimethylene)succinyl]-L-4'-acetamidomethylenephenylalanine-N-methylamide The compound (3-RS type, 500 mg, 0.97 mmol) of Example 10-c was dissolved in DMF (10 ml), added with acetic anhydride (109 μl, 1.16 mmol) and TEA (285 μl, 2.04 mmol) under stirring in an ice bath and stirred for 1 hour. The DMF was removed under reduced pressure. The residue was added with Et₂O and stirred at room temperature for 1 hour. The precipitating solid was filtered and dried in a desiccator under reduced pressure to give the title compound (500 mg, 98%) of a white solid.

m.p.; 155–161° C., specific rotation[α]$_D$=−14.3° (c=1.04, DMF), Rf value; 0.24 (CHCl₃:MeOH=10:1).

¹H-NMR(DMSO-d₄) δ ppm; 0.3–1.65 (13H, m, (CH₃)₂CH—CH₂, +CH₂—CH₂—CH₂—Ph), 1.80+1.82 (3H, s each, CH₃—CO), 1.9–3.7 (9H, m, N—CH₃+—CH—CO×2+CH₂—Ph+C₆H₄CH₂), 4.0–4.7 (3H, m, CH₂—NH+NH—CH—CO), 6.9–8.5 (12H, m, aromatic-H+NH×3).

(b) N-[4-(N-Bezyloxyamino)-2(R)-isobutyl-3(RS)-(3-phenyltrimethylene)succinyl]-L-4'-acetamidomethylenephenylalanine-N-methylamide By the same method (however, the DIAION HP-20 treatment was not done) as that in Example 10-e, the title compound (520 mg, 96%) of a white solid was obtained from the compound (450 mg, 0.86 mmol) of

EXAMPLE 13-a m.p.; 233–239° C. Rf value; 0.36 (CHCl₃:MeOH=10:1).

¹H-NMR(DMSO-d₄) δ ppm; 0.4–1.0 (6H, m, CH(CH₃)₂), 1.0–1.6 (7H, m, (CH₃)₂CH—CH₂+CH₂—CH₂—CH₂—Ph), 1.80+1.82 (3H, s each, CH₃—CO), 1.9–3.2 (9H, m, N—CH₃+—CH—CO×2+CH₂—Ph+C₆H₄CH₂), 4.0–4.7 (3H, m, CH₂—NH+NH—CH—CO), 4.76 (2H, s, OCH₂Ph), 6.8–8.5 (18H, m, aromatic-H+NH×4).

(c) N-[4-(N-Hydroxyamino-2(R)-isobutyl-3(RS)-(3-phenyltrimethylene)succinyl]-L-4'-acetamidomethylenephenylalanine-N-methylamide By the same method as that in Example 10-f, the title compound (130 mg, 32%) of white amorphous powder was obtained from the compound (470 mg, 0.75 mmol) of Example 13-b.

Specific rotation[α]$_D$=−15.0° (c=0.32, DMF), Rf value; 0.26 (CHCl₃:MeOH=10:1), 0.34 (CHCl₃:MeOH:AcOH= 5:2:1). Analytical value calculated for C₃₀H₄₂N₄O₅. Theoretical value:C, 66.89; H, 7.86; N, 10.4. Found:C, 66.85; H, 7.87; N, 10.44.

¹H-NMR (DMSO-d₄) δ ppm; 0.3–1.65 (13H, m, (CH₃)₂CH—CH₂, +CH₂—CH₂—CH₂—Ph), 1.80+1.82 (3H, s each, CH₃—CO), 1.9–3.7 (9H, m, N—CH₃+—CH—CO×2+CH₂—Ph+C₆H₄CH₂), 4.0–4.7 (3H, m, CH₂—NH+NH—CH—CO), 6.9–8.5 (13H, m, aromatic-H+NH×4).

EXAMPLE 14

N-[4-(N-Hydroxyamino)-2(R)-isobutyl-3(RS)-(3-phenyltrimethylene)succinyl]-L-4'-guanidomethylenephenylalanine-N-methylamide Monoacetate (a) N-[4-Hydroxy-2(R)-isobutyl-3(RS)-(3-phenyltrimethylene)succinyl]-L-4'-[N,N'-bis(benzyloxycarbonyl)guanidomethylene]phenylalanine-N-methylamide Monoacetate The compound (3-RS type, 500 mg, 0.97 mmol) of Example 10-c was dissolved in DMF (8 ml), added with 1H-pyrazole-N,N'-bis(benzyloxycarbonyl) carboxamidine (470 mg, 1.16 mmol) and TEA (162 μl, 1.16 mmol) under stirring in an ice bath and stirred at room temperature overnight. The DMF was removed under reduced pressure. The residue was added with Et₂O and stirred at room temperature for 1 hour. The precipitating solid was filtered and dried in a desiccator under reduced pressure to give the title compound (650 mg, 86%) of a white solid.

m.p.; 141–145° C., specific rotation[α]$_D$=−14.0° (c=0.71, DMF), RP value; 0.41 (CHCl₃:MeOH=10:1).

¹H-NMR(DMSO-d₆) δ ppm; 0.3–0.9 (6H, m, CH(CH₃)₂), 0.9–1.8 (7H, m, (CH₃)₂CH—CH₂, + CH₂—CH₂—CH₂—Ph), 2.0–3.1 (9H, m, —CH—CO×2+ CH₂—Ph+N—CH₃+C₆H₄CH₂), 4.3–4.7 (3H, m, CH₂—NH+NH—CH—CO), 5.03 (2H, s, OCH₂Ph), 5.19 (2H, s, OCH₂Ph), 6.8–7.6 (20H, m, aromatic-H+NH), 7.8–8.7 (1H, m, NH×3).

(b) N-[4-(N-benzyloxyamino)-2(R)-isobutyl-3(RS)-(3-phenyltrimethylene)succinyl]-L-4'-[N,N'-bis(benzyloxycarbonyl)guanidomethylene]phenylalanine-N-methylamide The compound (600 mg, 0.76 mmol) of Example 14-a, O-benzylhydroxylamine hydrochloride (180 mg, 1.14 mmol) and HOBT (120 mg, 0.91 mmol) were suspended in DMF (8 ml). The suspension was added with TEA (160 μl, 1.14 mmol) and EDC (170 mg, 0.91 mmol) at −15° C. under stirring. The mixture was stirred at −15° C. for 1 hour and further at room temperature overnight. The reaction mixture was dropped into 0.5N-HCl. The precipitating crystals were filtered, washed with aqueous 10% Na₂CO₃, water and then Et₂O and dried in a desiccator under reduced pressure to give the title compound (520 mg, 76%) of a white solid.

m.p.; 233–237° C., Rf value; 0.57 (CHCl$_3$:MeOH=10:1).

$^1$H-NMR(DMSO-d$_6$) δ ppm; 0.35–0.9 (6H, m, CH(CH$_3$)$_2$), 0.9–1.8 (7H, m, (CH$_3$)$_2$CH—CH$_2$+CH$_2$—CH$_2$—CH$_2$—Ph), 1.8–3.0 (9H, m, —CH—CO×2+CH$_2$—Ph+N—CH$_3$+C$_6$H$_4$CH$_2$), 4.25–4.6 (3H, m, CH$_2$—NH+NH—CH—CO), 4.76 (2H, s, OCH$_2$Ph), 5.02 (2H, s, OCH$_2$Ph), 5.19 (2H, s, OCH$_2$Ph), 6.8–7.5 (26H, m, aromatic-H+NH×2), 7.8–8.7 (1H, m, NH×3).

(c) N-[4-(N-Hydroxyamino)-2(R)-isobutyl-3(RS)-(3-phenyltrimethylene)succinyl]-L-4'-guanidomethylenephenylalanine-N-methylamide Monoacetate The compound (400 mg, 0.45 mmol) of Example 14-b was suspended in AcOH (20 ml), added with 5% Pd-C (50% wet, 400 mg) and then stirred vigorously in a stream of hydrogen at room temperature for 4 hours. After the catalyst was filtered off, AcOH of the filtrate was removed under reduced pressure. The residue was added with water (20 ml) to give the title compound (240 mg, 90%) of white amorphous powder upon freeze-drying.

Specific rotation[α]$_D$=−9.34° (c=0.97, DMF), Rf value; 0.19 (CHCl$_3$:MeOH:AcOH=5:2:1). Analytical value calculated for C$_{31}$H$_{46}$N$_6$O$_6$. Theoretical value:C, 62.19; H, 7.74; N, 14.04. Found:C, 62.2; H, 7.67; N, 14.04.

$^1$H-NMR(DMSO-d$_6$) δ ppm; 0.4–0.9 (6H, m, CH(CH$_3$)$_2$), 1.05–1.55 (7H, m, (CH$_3$)$_2$CH—CH$_2$, + CH$_2$—CH$_2$—CH$_2$—Ph), 1.70 (3H, s, CH$_3$COOH), 2.1–3.0 (9H, m, —CH—CO×2+CH$_2$—Ph+N—CH$_3$+C$_6$H$_4$CH$_2$), 4.0–4.6 (3H, m, CH$_2$—NH+NH—CH—CO), 6.9–7.5 (9H, m, aromatic-H+NH×2), 7.7–8.4 (4H, m, NH×4).

EXAMPLE 15

N-[4-(N-Hydroxyamino)-2(R)-isobutyl-3(R or S)-(3-phenyltrimethylene)succinyl]-O-sulfo-L-meta-tyrosine-N-methylamide, Monosodium Salt By the same methods as used in e–i oi Example 3, the following compounds were synthesized from L-meta-tyrosine-N-methylamide hydrochlodide.

(a) N-[4-tert-Butoxy-2(R)-isobutyl-3(R or S)-(3-phenyltrimethylene)succinyl]-L-meta-tyrosine-N-methylamide.

White solid (26%), m.p.; 72° C., specific rotation[α]$_D$=−15.7° (c=1.0, CHCl$_3$), Rf value; 0.57 (CHCl$_3$:MeOH=10:1).

$^1$H-NMR(CDCl$_3$) δ ppm; 0.82 (6H, m, CH(CH$_3$)$_2$), 0.9–2.0 (16H, s+m, (CH$_3$)$_2$CH—CH$_2$+C(CH$_3$)$_3$+CH$_2$—CH$_2$—CH$_2$—Ph), 2.2–3.2 (9H, m, N—CH$_3$+—CH—CO×2+CH$_2$—Ph+C$_6$H$_4$CH$_2$), 4.72 (1H, m, NH—CH—CO), 6.3–7.4 (11H, m, aromatic-H+NH×2), 8.00 (1H, brs, OH).

(b) N-[4-Benzyloxyamino-2(R)-isobutyl-3(R or S)-(3-phenyltrimethylene)succinyl]-L-meta-tyrosine-N-methylamide White solid (62%), m.p.; 229° C., specific rotation[α]$_D$=−8.8° (c=1.0, MeOH), Rf value; 0.48 (CHCl$_3$:MeOH=10:1).

$^1$H-NMR (MeOH-d$_4$) δ ppm; 0.8 (6H, m, CH(CH$_3$)$_2$), 0.9–1.7 (7H, m, (CH$_3$)$_2$CH—CH$_2$+CH$_2$—CH$_2$—CH$_2$—Ph), 1.8–3.2 (9H, m, N—CH$_3$+—CH—CO×2+CH$_2$—Ph+C$_6$H$_4$CH$_2$), 4.4–4.8 (1H, m, NH—CH—CO), 4.82 (2H, s, OCH$_2$Ph), 6.5–7.6 (14H, m, aromatic-H).

(c) N-[4-(N-Benzyloxyamino)-2(R)-isobutyl-3(R or S)-(3-phenyltrimethylene)succinyl]-O-sulfo-L-meta-tyrosine-N-methylamide, Monosodium Salt White amorphous powder (71%), specific rotation[α]$_D$=+2.6° (c=1.0, MeOH), Rf value; 0.66 (CHCl$_3$:MeOH:AcOH=5:2:1).

$^1$H-NMR(MeOH-d$_4$) δ ppm; 0.6–1.0 (6H, m, CH(CH$_3$)$_2$), 1.0–1.7 (7H, m, (CH$_3$)$_2$CH—CH$_2$+CH$_2$—CH$_2$—CH$_2$—Ph), 1.8–3.2 (9H, m, N—CH$_3$+—CH—CO×2+CH$_2$—Ph+C$_6$H$_4$CH$_2$), 4.4–4.7 (1H, m, NH—CH—CO), 4.82 (s, OCH$_2$Ph), 6.9–7.6 (14H, m, aromatic-H).

(d) N-[4-(N-Hydroxyamino)-2(R)-isobutyl-3(R or S)-(3-phenyltrimethylene)succinyl]-O-sulfo-L-meta-tyrosine-N-methylamide, Monosodium Salt White amorphous powder (quantative yield), specific rotation[α]$_D$=−3.7° (c=1.0, MeOH), Rf value; 0.49 (CHCl$_3$:MeOH:AcOH=5:2:1). Analytical value calculated for C$_{27}$H$_{36}$N$_3$O$_8$NaS. Theoretical value:C, 55.37; H, 6.2; N, 7.17. Found:C, 55.22; H, 6.04; N, 7.03.

$^1$H-NMR(MeOH-d$_4$) δ ppm; 0.5–1.75 (13H, m, (CH$_3$)$_2$CH—CH$_2$+CH$_2$—CH$_2$—CH$_2$—Ph), 1.9–2.85 (7H, m, N—CH$_3$+—CH—CO×2+CH$_2$—Ph), 2.9 (2H, m, C$_6$H$_4$CH$_2$), 4.65 (1H, m, NH—CH—CO), 6.8–7.4 (9H, m, aromatic-H).

EXAMPLE 16

N-[4-(N-Hydroxyamino)-2(R)-isobutyl-3(S)-hydroxysuccinyl]-L-4'-guanidophenylalanine-N-methylamide Monoacetate (a) Methyl 3(R)-carboxy-2(S)-hydroxy-5-methylhexanoate 3(R)-Carboxy-2(S)-hydroxy-5-methylhexanoate (440 mg, 2.31 mmol) was added with trifluoroacelic anhydrode (4 ml) and stirred at 0° C. for 4 hours. The mixture was evaporated under reduced pressure. The residue was added with MeOH (4 ml), stirred at 0° C. for 2 hours, evaporated under reduced pressure to remove MeOH and purified by column chromatography (silica gel; 35 g, elution with the mixed solvent; CHCl$_3$:MeOH=20:1) to give the title compound (344 mg, 73%) of a colorless oil.

$^1$H-NMR(CDCl$_3$) δ ppm; 0.94 (6H, d, J=5.0 Hz, CH(CH$_3$)$_2$), 1.3–2.0 (3H, m, (CH$_3$)$_2$CH—CH$_2$,), 2.8–3.2 (1H, m CH—CO$_2$H), 3.82 (3H, s, OCH$_3$), 4.29 (1H, d, J=3.5 Hz, HO—CH), 6.6 (2H, brm, OH+CO$_2$H).

(b) N-[3(S)-Hydroxy-2(R)-isobutyl-4-methoxysuccinyl]-L-4'-[N,N'-bis(benzyloxycarbonyl)guanido]phenylalanine-N-methylamide The compound (270 mg, 1.80 mmol) of Example 16-a, L-4'-[N,N'-bis(benzyloxycarbonyl)guanido]phenylalanine-N-methylamide hydrochloride (1.19 g, 2.20 mmol) and HOBT (540 mg, 4.00 mmol) were dissolved in DMF (6 ml). The solution was added with TEA (620 μl, 4.40 mmol) and EDC (420 mg, 2.20 mmol) at −15° C. under stirring. The mixture was stirred at −15° C. for 1 hour and further at 5° C. overnight and evaporated under reduced pressure. The residue was added with AcOEt (30 ml) and washed with a saturated aqueous solution of NaCl, 1N-HCl, a saturated aqueous solution of NaHCO$_3$ and then the saturated aqueous solution of NaCl two times respectively. The organic layer was dried over anhydrous MgSO$_4$, evaporated under reduced pressure and purified by column chromatography (silica gel; 50 g, elution with the mixed solvent; CHCl$_3$:MeOH=50:1) followed by crystallizing from chloroform-n-hexane to give the title compound (0.40 g, 45%) of a white solid.

m.p.; 175° C., specific rotation[α]$_D$=−17.4° (c=1.03, CHCl$_3$), Rf value; 0.20 (CHCl$_3$:MeOH=50:1).

$^1$H-NMR(CDCl$_3$) δ ppm; 0.7–1.1 (6H, m, CH(CH$_3$)$_2$), 1.0–1.6 (3H, m, (CH$_3$)$_2$CHCH$_2$), 2.4–3.5 (6H, d+m, J=4.8 Hz, N—CH$_3$+CH—CO+CH$_2$—C$_6$H$_4$), 3.65 (3H, s, CO$_2$CH$_3$), 3.90 (1H, m, NH), 4.23 (1H, m, NH—CH—CO), 4.4–4.7 (1H, m, HO—CH—CO), 5.08 (2H, s, Ph—CH$_2$—O), 5.25 (2H, s, Ph—CH$_2$—O), 6.34 (1H, m, NH), 6.75 (1H, m, HO), 7.0–7.7 (16H, m, aromatic-H+NH×2).

(c) N-[4-(N-Hydroxyamino)-2(R)-isobutyl-3(S)-hydroxysuccinyl]-L-4'-guanidophenylalanine-N-methylamide Monoacetate The compound (0.32 g, 0.46 mmol) of Example 16-b was added an ice-cooled MeOH solution of alkaline hydroxylamine (0.7 M, 5.0 ml), and the mixture was stirred at room temperature for 3 hours. The reaction liquid was made pH 3–4 by 1N-HCl and evaporated under reduced pressure.

The residue was dissolved in AcOH (20 ml), added with 5% Pd-C (50% wet, 0.5 g) and then stirred vigorously in a stream of hydrogen at room temperature for 5 hours. After the catalyst was filtered off, AcOH of the filtrate was removed under reduced pressure. The residue was purified by a reverse-phase column chromatography (Fuji Silysia Chemical Ltd., Chromatorex ODS DM-1020T; 50 g, elution with a MeOH-water solution containing 0–20% MeOH) to give the title compound (0.12 g, 54%) of white amorphous powder upon freeze-drying.

Specific rotation$[\alpha]_D$=+8.27° (c=1.04, MeOH), Rf value; 0.22 (CHCl$_3$:MeOH:AcOH=5:2:1). Analytical value calculated for $C_{21}H_{34}N_6O_7$. Theoretical value:C, 52.27; H, 7.1; N, 17.42. Found:C, 52.32; H, 7.21; N, 17.35.

$^1$H-NMR(MeOH-d$_4$) δ ppm; 0.86 (6H, m, CH(CH$_3$)$_2$), 1.0–1.85 (3H, m, (CH$_3$)$_2$CHCH$_2$), 1.90 (3H, s, CH$_3$CO$_2$H), 2.5–2.85 (4H, m, N—CH$_2$+CH—CO), 2.9–3.2 (2H, m, CH$_2$—C$_6$H$_4$), 4.5–5.0 (2H, m, NH—CH—CO+HO—CH—CO), 7.0–7.55 (4H, m, aromatic-H).

EXAMPLE 17

N-[4-(N-Hydroxyamino)-2(R)-isobutyl-3(R or S)-(3-phenyltrimethylene)succinyl]-L-4'-amidinophenylalanine-N-methylamide Monoacetate By the same methods as used in b–d of Example 8, the following compounds were synthesized from N$^\alpha$-tert-butyloxycarbonyl-4'-[N-(benzyloxycarbonyl)amidino]phenylalanine-N-methylamide.

(a) N-[4-tert-Butoxy-2(R)-isobutyl-3(R or S)-(3-phenyltrimethylene)succinyl]-L-4'-[N-(benzyloxycarbonyl)amidino]phenylalanine-N-methylamide White solid (18%), m.p.; 233° C. (dec.), specific rotation $[\alpha]_D$=+0.99° (c=1.1, MeOH), Rf value; 0.48 (CHCl$_3$:MeOH=10:1).

$^1$H-NMR(CDCl$_3$) δ ppm; 0.6–1.0 (6H, m, (CH$_3$)$_2$CH—CH$_2$), 1.0–1.6 (16H, s+m, (CH$_3$)$_2$CH—CH$_2$+CH$_2$—CH$_2$—CH$_2$—Ph+C(CH$_3$)$_3$), 2.2–2.8 (7H, d+m, J=4.7 Hz, —CH—CO×2+CH—Ph+N—CH$_3$), 3.10 (2H, m, C$_6$H$_4$CH$_2$), 4.56 (1H, m, NH—CH—CO), 5.20 (2H, s, Ph—CH$_2$—O), 6.2–6.6 (2H, m, NH×2), 7.1–7.5 (14H, m, aromatic-H), 7.7–7.9 (2H, m, NH×2).

(b) N-[4-(N-Benzyloxyamino)-2(R)-isobutyl-3(R or S)-(3-phenyltrimethylene)succinyl]-L-4'-[N-(benzyloxycarbonyl)amidino]phenylalanine-N-methylamide White solid (38%), m.p.; 259–261° C., Rf value; 0.40 (CHCl$_3$:MeOH=10:1).

$^1$H-NMR(CDCl$_3$) δ ppm; 0.85 (6H, m, (CH$_3$)$_2$CH—CH$_2$), 1.2–2.1 (9H, m, (CH$_3$)$_2$CH—CH$_2$+CH$_2$—CH$_2$—CH$_2$—Ph+—CH—CO×2), 2.5–3.2 (7H, m, C$_6$H$_4$CH$_2$+CH$_2$—Ph+N—CH$_3$), 4.5–5.1 (5H, m, NH—CH—CO+Ph—CH$_2$—O×2), 6.9–7.7 (19H, m, aromatic-H).

(c) N-[4-(N-Hydroxyamino)-2(R)-isobutyl-3(R or S)-(3-phenyltrimethylene)succinyl]-L-4'-amidinophenylalanine-N-methylamide Monoacetate White amorphous powder (96%), specific rotation$[\alpha]_D$=−7.04° (c=1.0, MeOH), Rf value; 0.45 (CHCl$_3$:MeOH:AcOH=5:2:1). Analytical value calculated for $C_{30}H_{43}N_5O_6$. Theoretical value:C, 63.25; H, 7.61; N, 12.29. Found:C, 63.33; H, 7.62; N, 12.34.

$^1$H-NMR(MeOH-d$_4$) δ ppm; 0.85 (6H, m, (CH$_3$)$_2$CH—CH$_2$), 1.1–1.75 (7H, m, (CH$_3$)$_2$CH—CH$_2$+CH$_2$—CH$_2$—CH$_2$—Ph), 1.91 (3H, s, CH$_3$CO$_2$H), 2.0–2.55 (4H, m, —CH—CO×2+CH$_2$—Ph), 2.67 (3H, m, N—CH$_3$), 2.8–3.2 (2H, m, C$_6$H$_4$CH$_2$), 4.5–5.0 (1H, m, NH—CH—CO), 6.9–7.85 (9H, m, aromatic-H).

EXAMPLE 18

N-[4-(N-Hydroxyamino)-2(R)-isobutyl-3(RS)-(3-phenyltrimethylene)succinyl]-O-sulfo-L-tyrosine-N-1-naphthylamide, Monosodium Salt By the same methods as used in e–i of Example 3, the following compounds were synthesized from L-tyrosine-N-1-naphthylamide hydrochloride.

(a) N-[4-tert-Butoxy-2(R)-isobutyl-3(RS)-(3-phenyltrimethylene)succinyl]-L-tyrosine-N-1-naphthylamide m.p.; 89–93° C., specific rotation$[\alpha]_D$=−18.8° (c=0.97, CHCl$_3$), Rf value; 0.72 (n-hexane:AcOEt=1:1).

$^1$H-NMR(CDCl$_3$) δ ppm; 0.6–0.9 (6H, m, (CH$_3$)$_2$CH—CH$_2$), 0.9–1.85 (16H, m, (CH$_3$)$_2$CH—CH$_2$+CH—CH$_2$—CH$_2$—Ph+C(CH$_3$)$_3$), 2.2–2.6 (4H, m, CH—CO×2+Ph—CH$_2$), 3.1 (2H, m, CH$_2$—C$_6$H$_4$), 4.97 (1H, m, NH—CH—CO), 6.6–8.1 (16H, m, aromatic-H).

(b) N-[4-Benzyloxyamino-2(R)-isobutyl-3(RS)-(3-phenyltrimethylene)succinyl]-L-tyrosine-N-1-naphthylamide m.p.; 210–235° C., specific rotation$[\alpha]_D$=−14.2° (c=1.0, DMF), Rf value; 0.58 (CHCl$_3$:MeOH=10:1).

$^1$H-NMR(DMSO-d$_6$) δ ppm; 0.4–0.95 (6H, m, (CH$_3$)$_2$CH—CH$_2$), 1.0–1.6 (7H, m, (CH$_3$)$_2$CH—CH$_2$+CH$_2$—CH$_2$—CH$_2$—Ph), 1.8–2.6 (4H, m, CH—CO×2+Ph—CH$_2$), 2.95 (2H, m, CH$_2$—C$_6$H$_4$), 4.6–5.0 (3H, m, NH—CH—CO+Ph—CH$_2$—O), 6.4–8.1 (21H, m, aromatic-H).

(c) N-[4-(N-Benzyloxyamino)-2(R)-isobutyl-3(RS)-(3-phenyltrimethylene)succinyl]-O-sulfo-L-tyrosine-N-1-naphthylamide, Monosodium Salt White amorphous powder (87%), specific rotation$[\alpha]_D$=−15.7° (c=1.0, MeOH), Rf value; 0.62 (CHCl$_3$:MeOH:AcOH=5:2:1).

$^1$H-NMR(MeOH-d$_4$) δ ppm; 0.6–1.0 (6H, m, (CH$_3$)$_2$CH—CH$_2$), 1.0–1.8 (7H, m, (CH$_3$)$_2$CH—CH$_2$+CH$_2$—CH$_2$—CH$_2$—Ph), 1.9–2.8 (4H, m, CH—CO×2+Ph—CH$_2$), 2.9–3.2 (2H, m, CH$_2$—C$_6$H$_4$), 4.5–5.1 (3H, s+m, NH—CH—CO+Ph—CH$_2$—O), 6.75 (1H, m, NH), 6.9–8.0 (21H, m, aromatic-H).

(d) N-[4-(N-Hydroxyamino)-2(R)-isobutyl-3(RS)-(3-phenyltrimethylene)succinyl]-O-sulfo-L-tyrosine-N-1-naphthylamide, Monosodium Salt White amorphous powder (94%), Rf value; 0.24 (CHCl$_3$:MeOH:AcOH=5:2:1). Analytical value calculated for $C_{36}H_{40}N_3O_8NaS$. Theoretical value:C, 61.97; H, 5.78; N, 6.02. Found:C, 61.74; H, 5.66; N, 5.97.

$^1$H-NMR(MeOH-d$_4$) δ ppm; 0.5–1.0 (6H, m, (CH$_3$)$_2$CH—CH$_2$), 1.0–1.8 (7H, m, (CH$_3$)$_2$CH—CH$_2$+CH$_2$—CH$_2$—CH$_2$—Ph), 1.8–2.8 (4H, m, CH—CO×2+Ph—CH$_2$), 3.1 (2H, m, CH$_2$—C$_6$H$_4$), 4.6–5.2 (1H, m, NH—CH—CO), 6.6–8.0 (16H, m, aromatic-H).

EXAMPLE 19

N-[4-(N-Hydroxyamino)-2(R)-isobutyl-3(RS)-(3-phenyltrimethylene)succinyl]-L-4'-guanidophenylalanine-N-phenylamide Monoacetate By the same methods as used in b–d of Example 8, the following compounds were synthesized from N$^\alpha$-tertbutyloxycarbonyl-4'-[N,N'-bis(benzyloxycarbonyl)guanido]phenylalanine-N-phenylamide.

(a) N-[4-tert-Butoxy-2(R)-isobutyl-3(RS)-(3-phenyltrimethylene)succinyl]-L-4'-[N,N'-bis(benzyloxycarbonyl)guanido]phenylalanine-N-phenylamide White solid (18%), m.p.; 166–169° C., specific rotation $[\alpha]_D = -10.5°$ (c=1.0, CHCl$_3$), Rf value; 0.21 (CHCl$_3$:MeOH=50:1).

$^1$H-NMR(CDCl$_3$) δ ppm; 0.6–0.9 (6H, m, (CH$_3$)CH$_2$CH—CH$_2$), 0.9–1.9 (16H, s+m, (CH$_3$)$_2$CH—CH$_2$+CH$_2$—CH$_2$—CH$_2$—Ph+C(CH$_3$)$_3$), 2.2–2.6 (4H, m, CH—CO×2+Ph—CH$_2$), 3.09 (2H, m, CH$_2$—C$_6$H$_4$), 4.6–5.0 (2H, m, NH—CH—CO+NH), 5.0–5.3 (4H, m, Ph—CH$_2$—O×2), 6.6–7.7 (27H, m, aromatic-H+NH×3).

(b) N-[4-(N-benzyloxyamino)-2(R)-isobutyl-3(RS)-(3-phenyltrimethylene)succinyl]-L-4'-[N,N'-bis(benzyloxycarbonyl)guanido]phenylalanine-N-phenylamide White solid (38%), m.p.; 240° C. (dec.), specific rotation $[\alpha]_D = +3.42°$ (c=1.1, DMF), Rf value; 0.32 (CHCl$_3$:MeOH=20:1).

$^1$H-NMR (DMSO-d$_6$) δ ppm; 0.3–0.95 (6H, m, (CH$_3$)$_2$CH—CH$_2$), 1.0–1.65 (7H, m, (CH$_3$)$_2$CH—CH$_2$+CH$_2$—CH$_2$—CH$_2$—Ph), 1.7–2.4 (4H, m, CH—CO×2+Ph—CH$_2$), 2.6–3.2 (2H, m, CH$_2$—C$_6$H$_4$), 4.5–4.95 (3H, s+m, NH—CH—CO+Ph—CH$_2$—O), 5.0–5.4 (4H, m, Ph—CH$_2$—O×2), 6.8–7.8 (29H, m, aromatic-H).

(c) N-[4-(N-Hydroxyamino)-2(R)-isobutyl-3(RS)-(3-phenyltriraethylene)succinyl]-L-4'-guanidophenylalanine-N-phenylamide Monoacetate White amorphous powder (96%), specific rotation $[\alpha]_D = -11.1°$ (c=1.0, MeOH), Rf value; 0.32 and 0.36 (CHCl$_3$:MeOH:AcOH=5:2:1). Analytical value calculated for C$_{35}$H$_{46}$N$_6$O$_6$. Theoretical value:C, 65; H, 7.17; N, 12.99. Found:C, 65.19; H, 7.18; N, 12.95.

$^1$H-NMR (MeOH-d$_4$) δ ppm; 0.5–1.8 (13H, m, (CH$_3$)$_2$CH—CH$_2$+CH$_2$—CH$_2$—CH$_2$—Ph), 1.92 (3H, s, CH$_3$CO$_2$H), 2.0–2.8 (4H, m, CH—CO×2+Ph—CH$_2$), 2.8–3.3 (2H, m, CH$_2$—C$_6$H$_4$), 4.5–5.2 (1H, m, NH—CH—CO), 6.8–7.8 (14H, m, aromatic-H).

EXAMPLE 20

Assay for Collagenase Inhibitory Activity

Inhibitory activities for collagenase (MMP-1) of the compounds of Examples and comparative compounds were measured by the method of Y. Murawaki et al., [*Journal of Hepatology*, 18, p. 328–334 (1993)]. The latent procollagenase was activated by incubating with mercury aminophenylacetate (2 mM) at 35° C. for 2 hours. The assay was done by using bovine type I collagen labeled with fluorescein as a substrate. The activated collagenase was added to the substrate solution (0.5 mg/ml) in Tris HCl buffer (50 mM, pH 7.5) containing sodium chloride (0.4 M) and calcium chloride (10 mM). The obtained solution was incubated at 35° C. for 2 hours. The enzyme digestion was stopped by the addition of o-phenanthroline (80 mM). The mixture was added with pig spleen elastase solution (25 µg/ml) in the above Tris HCl buffer, and incubated 37° C. for 10 min. The obtained solution was added with 70% ethanol and Tris HCl buffer (170 mM, pH 9.5) containing sodium chloride (0.61 M), whereby the indigested substrate was sedimented by centrifuging at 3000 g for 20 min. The supernatant was taken, and its intensity of fluorescence was determined by the excitation wavelength (495 nm) and the measured wavelength (520 nm), and the inhibitory activity was obtained.

IC$_{50}$ is a concentration of a compound assayed in the digesting enzyme, whereby the splitting of the substrate was decreased to 50% compared with that attained by the enzyme alone. The measurement results are shown in Table 1. Each compound showed equal or stronger inhibitory activity compared with the comparative compound (Table 1). Further, the comparative compounds are N-[4-(N-Hydroxyamino)-2(R)-isobutylsuccinyl]-O-methyl-L-tyrosine-N-methylamide (comparative compound 1, U.S. Pat. No. 4599361), N-[4-(N-Hydroxyamino)-2(R)-isobutyl-3(S)-phenyltrimethylenesuccinyl]-L-tyrosine-N-methylamide (comparative compound 2, EP No. 575844 A2), N-[4-(N-Hydroxyamino)-2(R)-isobutyl-3(S)-thienyltiomethylenesuccinyl]-L-phenylalanine-N-methylamide (comparative compound 3, U.S. Pat. No. 5,412,145) and N-[4-(N-Hydroxyamino)-2(R)-n-propyloxymethylene-3(S)-isopropylthiomethylenesuccinyl]-O-methyl-L-tyrosine-N-methylamide (comparative compound 4, U.S. Pat. No. 5,442,110), which were synthesized by referring to each patent.

TABLE 1

| Inhibitory activities for matrix metalloproeinases (MMPs) (IC$_{50}$ value, M) | | |
|---|---|---|
| Compound | MMP-1 | MMP-3 |
| Example 1 (Isomer B) | 5.1 × 10$^{-9}$ | 5.0 × 10$^{-7}$ |
| Example 2 | 4.2 × 10$^{-9}$ | 2.0 × 10$^{-7}$ |
| Example 9 | 1.7 × 10$^{-8}$ | 4.0 × 10$^{-7}$ |
| Comparative Compound 1 | 4.0 × 10$^{-9}$ | 1.1 × 10$^{-7}$ |
| Example 3 (Isomer B) | 4.0 × 10$^{-10}$ | 5.4 × 10$^{-9}$ |
| Example 7 | 8.0 × 10$^{-9}$ | 1.0 × 10$^{-8}$ |
| Example 8 | 6.0 × 10$^{-9}$ | 6.0 × 10$^{-9}$ |
| Example 10 | 7.0 × 10$^{-9}$ | 1.5 × 10$^{-8}$ |
| Example 11 | 5.8 × 10$^{-9}$ | 9.0 × 10$^{-9}$ |
| Example 12 | 1.0 × 10$^{-8}$ | 1.0 × 10$^{-8}$ |
| Example 13 | 4.0 × 10$^{-9}$ | 1.0 × 10$^{-8}$ |
| Example 14 | 4.0 × 10$^{-9}$ | 1.0 × 10$^{-8}$ |
| Example 15 | 8.0 × 10$^{-9}$ | 5.8 × 10$^{-9}$ |
| Example 17 | 5.0 × 10$^{-9}$ | 5.0 × 10$^{-9}$ |
| Example 18 | 5.0 × 10$^{-7}$ | 6.0 × 10$^{-9}$ |
| Example 19 | 8.0 × 10$^{-9}$ | 1.0 × 10$^{-8}$ |
| Comparative Compound 2 | 1.5 × 10$^{-10}$ | 8.0 × 10$^{-9}$ |
| Example 5 (Isomer A) | 8.0 × 10$^{-9}$ | 8.0 × 10$^{-9}$ |
| Comparative Compound 3 | 4.2 × 10$^{-10}$ | 3.0 × 10$^{-9}$ |
| Example 6 | 2.0 × 10$^{-8}$ | 2.8 × 10$^{-7}$ |
| Comparative Compound 4 | 1.1 × 10$^{-8}$ | 1.0 × 10$^{-7}$ |

EXAMPLE 21

Assay for Stromelysin Inhibitory Activity

Inhibitory activities for stromelysin (MMP-3) of the compounds of Examples and comparative compounds were measured by the method of S. S. Twining et al., [*Anal. Biochem.*, 143, p. 30 (1984)]. The latent prostromelysin was incubated with human plasmin (20 µg/ml) for the activation at 37° C. for 2 hours, and then the incubate was added with diisopropyl fluorophosphate solution (2.8 mg/ml) to stop the reaction. The assay was done by using casein labeled with fluorescein as the substrate. The activated stromelysin was added to a substrate solution (1 mg/ml) in Tris HCl buffer (50 mM, pH 7.8) containing calcium chloride (10 mM). The obtained solution was incubated at 37° C. for 2 hours. The enzyme digestion for the substrate was stopped by adding 5% trichloroacetic acid. The indigested substrate was sedimented by centrifuging at 3000 g for 20 min. The supernatant was taken and added with Tris HCl buffer (0.5 M, pH 8.5), whereby its intensity of fluorescence was determined by the excitation wavelength (495 nm) and the measured wavelength (520 nm), and the inhibitory activity was obtained. $IC_{50}$ is a concentration of a compound assayed in the digesting enzyme, whereby the splitting of the substrate was decreased to 50% compared with that attained by the enzyme alone. The measurement results are shown in Table 1. Each compound having the same stereo-configuration as that of the comparative compound showed equal or stronger inhibitory activity compared with the comparative compound (Table 1).

EXAMPLE 22

Assay for Suppression of TNF-α Production

Human monocyte derived leukemia cell-line U937 [5% bovine fetal serum (Men-eki Seibutsu Ken) was added to RPMI1640 (Nissui Seiyaku) and incubated in a 5% $CO_2$ incubation chamber at 37° C., whereby $1 \times 10^6$ cells/1 ml were placed into each well of a multi-well plate and then incubated in presence of Phorbol 12-myristate 13-acetate ($10^{-7}$ M, Wako Junyaku) overnight and differentiated to macrophage like cells.] was added with Lipopoplysaccaride (0.1 μg/ml, Sigma) derived from E.coli 0127:B8 strain alone or together with a compound in Examples, and incubated in a 5% $CO_2$ incubation chamber at 37° C. for 6 hours. After the incubation, the culture medium was taken and centrifuged at 3000 g for 10 min., whereby the supernatant was diluted with purified water for the measurement using the TNF-α measurement kit (Genzyme) (Table 2).

TABLE 2

Inhibitory activities for TNF-α converting enzyme
Compound $IC_{50}$ value (M)

| Compound | $IC_{50}$ |
|---|---|
| Example 4 | $5.1 \times 10^{-7}$ |
| Example 5 | $5.0 \times 10^{-7}$ |
| Example 8 | $9.8 \times 10^{-8}$ |
| Example 11 | $4.0 \times 10^{-7}$ |
| Example 16 | $7.0 \times 10^{-6}$ |

EXAMPLE 23

Measurement of Solubility in Water

A compound of Examples or a comparative compound was added to distilled water and shaken vigorously at 20±5° C. for 30 seconds at 5 min. interval. After 30 min., it was checked by watching with eye whether the compound was dissolved or not. The measurement results are shown in Table 3. The solubility of each of the comparative compounds are less than 1 mg/ml. On the contrary, those of the compounds in Examples are not less than 30–320 mg/ml of water-solubility (Table 3).

TABLE 3

Solubility in water

| Compound | mg/ml |
|---|---|
| Example 1 (Isomer A) | >240 |
| Example 1 (Isomer B) | >240 |
| Example 2 | >250 |
| Example 9 | >200 |
| Comparative Compound 1 | 1> |
| Example 3 (Isomer A) | >100 |
| Example 3 (Isomer B) | 150 |
| Example 4 | 150 |
| Example 7 | 100 |

TABLE 3-continued

Solubility in water

| Compound | mg/ml |
|---|---|
| Example 8 | 30 |
| Example 15 | 120 |
| Comparative Compound 2 | 1> |
| Example 5 (Isomer A) | >320 |
| Example 5 (Isomer B) | >300 |
| Comparative Compound 3 | 1> |
| Example 6 | >120 |
| Comparative Compound 4 | 1> |

EXAMPLE 24

Acute Toxicity Test

A compound of Examples was dissolved in water for injection at the concentration of 10 mg/ml. The solution was injected in a mouse tail vein in 10 mg/Kg. The behavior of mice was watched for 8 days.

In all the compounds of Examples, there was observed no example of death and of body weight loss.

The next embodiment shows pharmaceutical preparations containing a compound of formula (I) provided by the invention.

EXAMPLE 25

Ointment containing the following ingredients could be prepared by a conventional method.

| Ingredient | Amount |
|---|---|
| A: | |
| White vaseline | 97.8 g |
| Liquid paraffin | 2 g |
| Example 1 compound (isomer B) | 0.2 g |
| Total amount | 100 g |
| B: | |
| White vaseline | 97.8 g |
| Purified lanoline | 2 g |
| Example 1 compound (isomer B) | 0.2 g |
| Total amount | 100 g |
| C: | |
| White vaseline | 99.8 g |
| Example 1 compound (isomer B) | 0.2 g |
| Total amount | 100 g |

EXAMPLE 26

Eye drops containing the following ingredients could be prepared by a conventional method.

| Ingredient | Amount |
|---|---|
| A: | |
| Example 4 compound | 0.1 g |
| Sodium chloride | 0.33 g |

-continued

| Ingredient | Amount |
|---|---|
| Purified sterile water | appropriate |
| Total amount | 100 g |
| B; | |
| Example 4 compound | 0.1 g |
| Sodium chloride | 0.26 g |
| Anhydrous sodium dihydrogenphosphate | 0.56 g |
| Anhydrous sodium hydrogenphosphate | 0.28 g |
| 0.002% Benzalkonium chloride solution | appropriate |
| Total amount | 100 g |
| C; | |
| Example 4 compound | 0.1 g |
| Sodium chloride | 0.33 g |
| Anhydrous sodium sulfite | 0.10 g |
| Purified sterile water | appropriate |
| Total amount | 100 g |
| D; | |
| Example 4 compound | 0.1 g |
| Sodium chloride | 0.33 g |
| Purified sterile water | appropriate |
| Total amount | 100 g |

EXAMPLE 27

Injections containing the following ingredients could be prepared by a conventional method.

| Ingredient | Amount |
|---|---|
| A; | |
| Example 4 compound | 0.2 g |
| Distilled water for injection | appropriate |
| Total amount | 100 g |
| B; | |
| Example 4 compound | 0.2 g |
| Sodium chloride | 0.9 g |
| Distilled water for injection | appropriate |
| Total amount | 100 g |
| C; | |
| Example 4 compound | 0.2 g |
| Anhydrous sodium dihydrogenphosphate | 28 mg |
| Anhydrous sodium hydrogenphosphate | 167 mg |
| Sodium chloride | 0.9 g |
| Distilled water for injection | appropriate |
| Total amount | 100 g |

What is claimed is:

1. Compounds of the general formula (III)

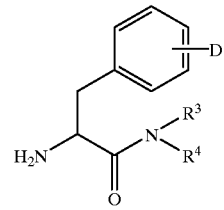

IIII wherein,
$R^3$ is a hydrogen atom, or a $(C_1-C_6)$alkyl, aryl or aryl $(C_1-C_6)$alkylene group,
$R^4$ is a hydrogen atom, or a $(C_1-C_6)$alkyl, aryl, aryl $(C_1-C_6)$alkylene or p-methoxyphenyl group,
D is a hydrogen atom, a hydroxyl, protected phosphoric acid, protected diphosphonomethine, protected dicarboxymethine, nitro, amino, protected guanido, protected guanidomethylene, cyano, aminomethylene or protected amidino group, —Y—C" or C" group, wherein
Y is a $(C_1-C_6)$alkylene group, an oxygen atom, an imino group, or a $(C_1-C_6)$alkyleneimino group,
C" is a sulfonic, phosphonic acid, amidino, $(C_1-C_6)$ acyl, acylimidoyl, diphosphonomethine or dicarboxymethine group, with the provisio that at least one of $R^3$, $R^4$ and D is not a hydrogen atom and that when D is a hydroxyl group and either $R^3$ or $R^4$ is a hydrogen atom, neither $R^3$ nor $R^4$ is an ethyl or an n-propyl group.

2. Compounds of the general formula (IV)

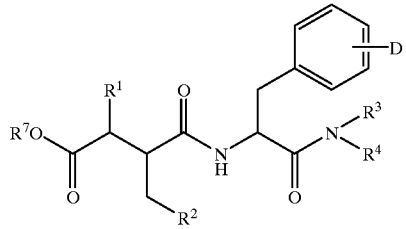

IV wherein,
$R^1$ is a hydrogen atom, or a hydroxyl, aryl$(C_1-C_6)$ alkylene or —A—SO$_n$—B group
wherein A is a $(C_1-C_6)$alkylene group,
B is a $(C_1-C_6)$alkyl, $(C_1-C_6)$acyl, aryl or heterocycle group, and
n is 0, 1 or 2;
$R^2$ is a hydrogen atom, or a $(C_1-C_4)$alkyl, $(C_1-C_6)$ alkyloxy or $(C_1-C_6)$alkylthio group;
$R^3$ is a hydrogen atom, or a $(C_1-C_6)$alkyl, aryl or aryl $(C_1-C_6)$alkylene group;
$R^4$ is a hydrogen atom, or a $(C_1-C_6)$alkyl, aryl, aryl $(C_1-C_6)$alkylene or p-methoxyphenyl group;
$R^7$ is $(C_1-C_6)$alkyl, benzyl, substituted benzyl, phenacyl or 2,2,2-trichloroethyl group;
D is a hydrogen atom, a hydroxyl, protected phosphoric acid, protected diphosphonomethine, protected dicarboxymethine, nitro, amino, protected guanido, protected guanidomethylene, cyano, aminomethylene or protected amidino group, —Y—C" or C" group, wherein Y is a $(C_1-C_6)$alkylene group, an oxygen atom, an imino group, or a $(C_1-C_6)$alkyleneimino group, C" is a sulfonic, phosphonic acid, amidino, $(C_1-C_6)$acyl, acylimidoyl, diphosphonomethine or dicarboxymethine group, with the proviso that when D is a hydroxyl group, $R^2$ is an iso-propyl group and either $R^3$ or $R^4$ is a hydrogen atom, neither $R^3$ nor $R^4$ is a methyl group.

3. Compounds of the general formula (V)

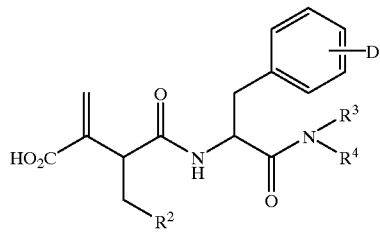

V wherein $R^2$ is a hydrogen atom, or a $(C_1-C_4)$alkyl, $(C_1-C_6)$alkyloxy or $(C_1-C_6)$alkylthio group;

$R^3$ is a hydrogen atom, or a $(C_1-C_6)$alkyl, aryl or aryl $(C_1-C_6)$alkylene group, $R^4$ is a hydrogen atom, or a $(C_1-C_6)$alkyl, aryl, aryl $(C_1-C_6)$alkylene or p-methoxyphenyl group, D is a hydrogen atom, a hydroxyl, protected phosphoric acid, protected diphosphonomethine, protected dicarboxymethine, nitro, amino, protected guanido, protected guanidomethylene, cyano, aminomethylene or protected amidino group, —Y—C" or C" group, wherein Y is a $(C_1-C_6)$alkylene group, an oxygen atom, an imino group, or a $(C_1-C_6)$alkyleneimino group, C" is a sulfonic, phosphonic acid, amidino, acylimidoyl, diphosphonomethine or dicarboxymethine group.

\* \* \* \* \*

UNITED STATES PATENT AND TRADEMARK OFFICE
CERTIFICATE OF CORRECTION

PATENT NO.    : 6,284,914 B1
DATED         : September 4, 2001
INVENTOR(S)   : Junko Yasuda et al.

It is certified that error appears in the above-identified patent and that said Letters Patent is hereby corrected as shown below:

<u>Title page,</u>
Item [75], Inventors: please correct the name of the first inventor from "Junko Fujisawa" to -- Junko Yasuda --.

Signed and Sealed this

Tenth Day of September, 2002

Attest:

Attesting Officer

JAMES E. ROGAN
*Director of the United States Patent and Trademark Office*